United States Patent
Laughlin, II et al.

(10) Patent No.: US 11,571,378 B2
(45) Date of Patent: Feb. 7, 2023

(54) SKIN CARE COMPOSITION AND METHOD OF USING THE SAME

(71) Applicant: The Procter & Gamble Company, Cincinnati, OH (US)

(72) Inventors: Leo Timothy Laughlin, II, Mason, OH (US); Michael Joseph Flagler, Anderson Township, OH (US); Lisa Ann Mullins, West Chester, OH (US); Makio Tamura, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 17/155,357

(22) Filed: Jan. 22, 2021

(65) Prior Publication Data

US 2022/0233424 A1    Jul. 28, 2022

(51) Int. Cl.
*A61K 38/00* (2006.01)
*A61K 8/64* (2006.01)
*A61Q 19/00* (2006.01)

(52) U.S. Cl.
CPC ............... *A61K 8/64* (2013.01); *A61Q 19/00* (2013.01)

(58) Field of Classification Search
CPC ........... A61K 8/64; A61Q 19/00; A61Q 19/08
See application file for complete search history.

(56) References Cited

U.S. PATENT DOCUMENTS

| | | |
|---|---|---|
| 3,755,560 A | 8/1973 | Dickert et al. |
| 4,421,769 A | 12/1983 | Dixon et al. |
| 5,011,681 A | 4/1991 | Ciotti et al. |
| 5,872,112 A | 2/1999 | Blank |
| 5,939,082 A | 8/1999 | Oblong et al. |
| 5,972,359 A | 10/1999 | Sine et al. |
| 6,174,533 B1 | 1/2001 | Sanogueira, Jr. et al. |
| 6,492,326 B1 | 12/2002 | Robinson |
| 6,524,598 B2 | 2/2003 | Sunkel et al. |
| 6,696,049 B2 | 2/2004 | Vatter |
| 8,568,751 B1 * | 10/2013 | Goldsberry ............ A61Q 19/08 424/401 |
| 9,192,558 B2 | 11/2015 | Chen et al. |
| 9,446,265 B2 | 9/2016 | Jansen et al. |
| 9,511,010 B2 | 12/2016 | Van Den Nest et al. |
| 9,597,274 B2 | 3/2017 | Idkowiak-baldys et al. |
| 9,795,552 B2 | 10/2017 | Tanner et al. |
| 9,833,405 B2 | 12/2017 | Xu et al. |
| 10,265,348 B2 | 4/2019 | Soley Astals et al. |
| 10,668,000 B2 | 6/2020 | Peschard et al. |
| 2002/0022040 A1 | 2/2002 | Robinson et al. |
| 2003/0049212 A1 | 3/2003 | Robinson et al. |
| 2004/0175347 A1 | 9/2004 | Bissett |
| 2006/0018860 A1 | 1/2006 | Chen et al. |
| 2006/0275237 A1 | 12/2006 | Bissett |
| 2007/0196344 A1 | 8/2007 | Osborne et al. |
| 2008/0095732 A1 | 4/2008 | Osborne |
| 2008/0181956 A1 | 7/2008 | Ha et al. |
| 2008/0206373 A1 | 8/2008 | Millikin et al. |
| 2009/0111731 A1 | 4/2009 | Imfeld et al. |
| 2010/0092408 A1 | 4/2010 | Breyfogle |
| 2010/0098752 A1 | 4/2010 | Pinsky |
| 2010/0189669 A1 | 7/2010 | Hakozaki |
| 2010/0227011 A1 | 9/2010 | Kuhlman et al. |
| 2010/0239510 A1 | 9/2010 | Ha et al. |
| 2010/0272667 A1 | 10/2010 | Kyte, III et al. |
| 2011/0097286 A1 | 4/2011 | Swanson |
| 2011/0262025 A1 | 10/2011 | Jarrold et al. |
| 2011/0262570 A1 | 10/2011 | Finlay et al. |
| 2011/0300199 A1 | 12/2011 | Garcia et al. |
| 2011/0305737 A1 | 12/2011 | Alexiades-armenakas |
| 2012/0028916 A1 | 2/2012 | Fournial et al. |
| 2012/0076842 A1 | 3/2012 | Fournial et al. |
| 2012/0121675 A1 | 5/2012 | Garcia et al. |
| 2012/0128683 A1 | 5/2012 | Shantha |
| 2012/0148515 A1 | 6/2012 | Hakozaki et al. |
| 2012/0156146 A1 | 6/2012 | Hakozaki et al. |
| 2012/0197016 A1 | 8/2012 | Laughlin, II |
| 2012/0301410 A1 | 11/2012 | Ali |
| 2012/0315235 A1 | 12/2012 | Weisenfluh et al. |
| 2013/0017239 A1 | 1/2013 | Viladot et al. |
| 2013/0022557 A1 | 1/2013 | Swanson et al. |
| 2013/0064876 A1 | 3/2013 | Viladot et al. |
| 2013/0101662 A1 | 4/2013 | Carreno et al. |

(Continued)

FOREIGN PATENT DOCUMENTS

| | | |
|---|---|---|
| CN | 103767971 A | 5/2014 |
| CN | 104688622 A | 6/2015 |

(Continued)

OTHER PUBLICATIONS

English language translation of CN 107375041 A provided by Google patents (Year: 2017).*
All Office Actions; U.S. Appl. No. 17/155,327, filed Jan. 22, 2021.
Generation of a Stable Antioxidant Response Element-Driven Reporter Gene Cell Line and Its Use to Show Redox-Dependent Activation of Nrf2 by Cancer Chemotherapeutic Agents. Cancer Res 2006; 66(22): Nov. 15, 2006; pp. 10983-10994.
He M. et al, "The role of sterol-C4-methyl oxidase in epidermal biology." Biochim Biophys Acta. Mar. 2014; 1841(3), pp. 331-335.
Lopez-Leon, S et al. "Sports genetics: the PPARA gene and athletes' high ability in endurance sports. A systematic review and meta-analysis." Biology of sport vol. 33,1 (2016): pp. 3-6.

(Continued)

*Primary Examiner* — Aradhana Sasan
*Assistant Examiner* — Mercy H Sabila
(74) *Attorney, Agent, or Firm* — Alexandra S. Anoff

(57) ABSTRACT

A skin care composition that includes a combination of palmitoyl dipeptide-7, acetyl tetrapeptide-11, other optional skin ingredients, and a dermatologic ally acceptable carrier. The combination of peptides synergistically improves cellular ATP level and/or upregulates the expression of peroxisome proliferator activated receptor alpha and/or methyl-sterol monooxygenase 1 to help provide improved skin health and appearance.

12 Claims, No Drawings
Specification includes a Sequence Listing.

(56) References Cited

U.S. PATENT DOCUMENTS

| | | |
|---|---|---|
| 2013/0216596 A1 | 8/2013 | Viladot et al. |
| 2013/0302261 A1 | 11/2013 | Courtois et al. |
| 2014/0370098 A1 | 12/2014 | Terrisse et al. |
| 2015/0017269 A1 | 1/2015 | Fournial et al. |
| 2015/0071974 A1 | 3/2015 | Ferrer Montiel et al. |
| 2015/0098989 A1 | 4/2015 | Ferrer Montiel et al. |
| 2015/0140046 A1 | 5/2015 | Ferrer Montiel et al. |
| 2015/0183823 A1 | 7/2015 | Garca et al. |
| 2015/0196464 A1 | 7/2015 | Jansen et al. |
| 2016/0074291 A1 | 3/2016 | Tamura et al. |
| 2016/0074301 A1 | 3/2016 | Tamura et al. |
| 2016/0074309 A1 | 3/2016 | Kessler-becker et al. |
| 2016/0120794 A1 | 5/2016 | Liu et al. |
| 2016/0317419 A1 | 11/2016 | Hakazaki et al. |
| 2017/0319462 A1 | 11/2017 | Marchant et al. |
| 2018/0264245 A1 | 9/2018 | Edwards et al. |
| 2018/0311358 A1 | 11/2018 | Marchant et al. |
| 2018/0332951 A1 | 11/2018 | Jang et al. |
| 2018/0369579 A1 | 12/2018 | Jang et al. |
| 2019/0099362 A1 | 4/2019 | Ringenbach et al. |
| 2019/0153030 A1 | 5/2019 | Peschard et al. |
| 2020/0297654 A1 | 9/2020 | Marchant et al. |
| 2021/0069088 A1 | 3/2021 | Jiang et al. |

FOREIGN PATENT DOCUMENTS

| | | | |
|---|---|---|---|
| CN | 105342927 A | | 2/2016 |
| CN | 105560078 A | | 5/2016 |
| CN | 105640845 A | | 6/2016 |
| CN | 105748319 A | | 7/2016 |
| CN | 107184459 A | | 9/2017 |
| CN | 107375041 A | * | 11/2017 |
| CN | 107802561 A | | 3/2018 |
| CN | 108309919 A | | 7/2018 |
| CN | 108670896 A | | 10/2018 |
| CN | 109330964 A | | 2/2019 |
| CN | 109394612 A | | 3/2019 |
| CN | 109453095 A | | 3/2019 |
| CN | 109464307 A | | 3/2019 |
| CN | 109846804 A | | 6/2019 |
| CN | 109953927 A | | 7/2019 |
| CN | 109984952 A | | 7/2019 |
| CN | 110074990 A | | 8/2019 |
| CN | 110123729 A | | 8/2019 |
| CN | 110179725 A | | 8/2019 |
| CN | 110269831 A | | 9/2019 |
| CN | 110302077 A | | 10/2019 |
| CN | 110302089 A | | 10/2019 |
| CN | 110384629 A | | 10/2019 |
| CN | 110420160 A | | 11/2019 |
| CN | 110522711 A | | 12/2019 |
| CN | 110585055 A | | 12/2019 |
| CN | 110585056 A | | 12/2019 |
| EP | 1790330 A2 | | 5/2007 |
| JP | 2003040724 A | | 2/2003 |
| JP | 2004238354 A | | 8/2004 |
| JP | 2004238355 A | | 8/2004 |
| JP | 2013053147 A | | 3/2013 |
| JP | 2014114289 A | | 6/2014 |
| KR | 20090062226 A | | 6/2009 |
| KR | 101769416 B1 | | 8/2017 |
| KR | 20190116693 A | | 10/2019 |
| WO | 0062743 A2 | | 10/2000 |
| WO | 2012164488 A2 | | 12/2012 |
| WO | 2018236069 A1 | | 12/2018 |

OTHER PUBLICATIONS

Silke Karin Schagen, "Topical Peptide Treatments with Effective Anti-Aging Results", Cosmetics, 2017—mdpi.com, retrieved from https://doi.org/10.3390/cosmetics4020016, May 22, 2017, pp. 1-14.
U.S. Unpublished U.S. Appl. No. 17/155,327, filed Jan. 15, 2021, to Leo Timothy Laughlin et. al.
15965 PCT Search Report and Written Opinion for PCT/US2022/070278 dated May 12, 2022, 11 pages.
Database GNPD [Online] 1 MINTEL; Aug. 13, 2021 (Aug. 8, 2021), anonymous: "Serum", XP055915466, Database accession No. 8935135, the whole document, 5 pages.
Database GNPD [Online] 1 MINTEL; Jun. 21, 2021 (Jun. 21, 2021), anonymous: "Eye Cream", XP055915464, Database accession No. 8749319, the whole document, 5 pages.
Database GNPD [Online] MINTEL; Oct. 23, 2020 (Oct. 23, 2020), anonymous: "Cream", XP055917310, Database accession No. 8209161 the whole document, 5 pages.

* cited by examiner

SKIN CARE COMPOSITION AND METHOD OF USING THE SAME

FIELD

The present disclosure is directed generally to skin care compositions and methods for improving cellular energy levels and renewing the extracellular matrix. More specifically, the present invention is directed to a combination of peptides that synergistically modulate certain genes involved in cellular energy production and extracellular matrix repair.

BACKGROUND

Skin is the first line of defense against environmental insults that would otherwise damage sensitive underlying tissue and organs, and skin plays a key role in a person's physical appearance. The tell-tale signs of skin aging, such as wrinkles and age spots on the skin, are an undesirable reminder of the disappearance of youth. As a result, treating the signs of aging in skin has become a booming business in youth-conscious societies.

Skin is made up of a variety of different cells that function together in a dynamic, complex relationship to maintain the health of the skin. However, as skin cells age or become damaged, they can lose their ability to function at the level needed to maintain young, healthy looking skin. Skin cells can be damaged by a variety of endogenous and exogenous stressors (e.g., ultraviolet radiation, pollution, smoking). In some instances, these stressors can cause the production of reactive oxygen species (ROS), which interfere with normal cellular processes. In response, cells have evolved defenses to combat ROS, but the cell's defenses can be overwhelmed by spikes of stressor-induced ROS, leading to not just acute but also chronic alterations in cellular homeostasis. As ROS accumulate over time, they cause oxidative stress at the cellular level, which can ultimately manifest as visible signs of aging (e.g., fine lines, wrinkles, hyperpigmented spots, thinning skin).

The use of peptides in skin care compositions is generally known. The variety of commercially available peptides and the range of skin care benefits these peptides can provide make them attractive ingredients for skin care compositions. For example, U.S. Pat. No. 9,597,274 describes using peptides derived from growth factors, such as Growth Differentiation Factor 11, for improving the health and/or appearance of skin. In another example, U.S. Pat. No. 10,668,000 describes in skin care compositions that can contain a variety of different peptides that are active in the synthesis of ECM proteins and generally improve the appearance of skin. However, peptides can be expensive, especially those that are known to provide a skin care benefit. As a result, peptides are typically added to skin care compositions in relatively low amounts, and thus it can be important to select peptides that provide good efficacy at low concentrations.

Accordingly, it would be desirable to provide a peptide-containing skin care composition that can improve the health and appearance of human skin, especially skin that exhibits a visible sign of aging. In particular, it would be desirable to provide a peptide-containing skin care composition that improves cellular energy production and/or ECM repair and renewal processes in a skin cell by targeting specific genes involved in these biochemical pathways. It would further be desirable to provide a combination of peptides that provide desirable efficacy at low concentrations.

SUMMARY

Disclosed herein is a skin care composition, comprising: a combination of palmitoyl dipeptide-7 (pal-KT) and acetyl tetrapeptide-11 (ac-PPYL) [SEQ ID NO: 1]; and a dermatologically acceptable carrier. Also disclosed is a method of treating a skin condition comprising applying the novel composition herein to a target portion of skin where treatment is desired. The combination of peptides can improve cellular ATP level and/or upregulate certain genes involved in ECM repair and renewal processes, in some instances synergistically.

DETAILED DESCRIPTION

The use of peptides for improving the health and appearance of skin is generally known. However, it has now been surprisingly discovered that a combination of palmitoyl dipeptide-7 ("pal-KT") and acetyl tetrapeptide-11 (ac-PPYL) [SEQ ID NO: 1] can boost cellular energy production and ECM repair and renewal processes. In particular, select combinations of pal-KT and ac-PPYL [SEQ ID NO: 1] can synergistically modulate the expression of key genes known to be involved in cellular bioenergetics and ECM repair and renewal. Improving cellular energy production and/or ECM repair and renewal is important for improving the health and/or appearance of skin, especially skin that exhibits visible signs of aging.

Reference herein to "embodiment(s)" or the like means that a particular material, feature, structure and/or characteristic described in connection with the embodiment is included in at least one embodiment, optionally a number of embodiments, but it does not mean that all embodiments incorporate the material, feature, structure, and/or characteristic described. Furthermore, materials, features, structures and/or characteristics may be combined in any suitable manner across different embodiments, and materials, features, structures and/or characteristics may be omitted or substituted from what is described. Thus, embodiments and aspects described herein may comprise or be combinable with elements or components of other embodiments and/or aspects despite not being expressly exemplified in combination, unless otherwise stated or an incompatibility is stated.

In all embodiments, all ingredient percentages are based on the weight of the cosmetic composition, unless specifically stated otherwise. All ratios are weight ratios, unless specifically stated otherwise. The number of significant digits conveys neither a limitation on the indicated amounts nor on the accuracy of the measurements. All numerical amounts are understood to be modified by the word "about" unless otherwise specifically indicated. Unless otherwise indicated, all measurements are understood to be made at approximately 25° C. and at ambient conditions, where "ambient conditions" means conditions under about 1 atmosphere of pressure and at about 50% relative humidity. All numeric ranges are inclusive and combinable to form narrower ranges not explicitly disclosed. For example, delineated upper and lower range limits are interchangeable to create further ranges.

The compositions of the present invention can comprise, consist essentially of, or consist of, the essential components as well as optional ingredients described herein. As used herein, "consisting essentially of" means that the composition or component may only include additional ingredients that do not materially alter the basic and novel characteristics of the claimed composition or method. As used in the description and the appended claims, the singular forms "a", "an", and "the" are intended to include the plural forms as well, unless the context clearly indicates otherwise.

SEQUENCE LISTING

A sequence listing that sets forth the amino acid or nucleotide sequences for SEQ ID NO: 1 and the nucleotide sequences for SEQ ID NOS: 2 and 3, which are primary sequences and include conservatively modified variants thereof, is being filed concurrently with the present application as an ASCII text file titled "15965_seq_list_ST25". This ASCII text file was created on Jan. 19, 2021 and is 138 KB in size. In accordance with MPEP § 605.08 and 37 CFR § 1.52(e), the subject matter in the ASCII text file is incorporated herein by reference.

Definitions

"About" modifies a particular value by referring to a range equal to plus or minus twenty percent (+/−20%) or less (e.g., less than 15%, 10%, or even less than 5%) of the stated value.

"Apply" or "application", as used in reference to a composition, means to apply or spread the compositions of the present invention onto a human skin surface such as the epidermis.

"Cosmetic composition" means a composition comprising a cosmetic agent and intended for non-therapeutic (i.e., medical) use. Examples of cosmetic compositions include color cosmetics (e.g., foundations, lipsticks, concealers, and mascaras), skin care compositions (e.g., moisturizers and sunscreens), personal care compositions (e.g., rinse-off and leave on body washes and soaps), hair care compositions (e.g., shampoos and conditioners).

"Derivative," herein, means amide, ether, ester, amino, carboxyl, acetyl, and/or alcohol derivatives of a given compound.

"Effective amount" means an amount of a compound or composition sufficient to significantly induce a positive benefit to keratinous tissue over the course of a treatment period. The positive benefit may be a health, appearance, and/or feel benefit, including, independently or in combination, the benefits disclosed herein. In a specific example, an effective amount of sucrose ester and fatty alcohol is an amount sufficient to increase cellular ATP levels that have been reduced as a result of oxidative stress.

"Skin care" means regulating and/or improving a skin condition (e.g., skin health, appearance, or texture/feel). Some nonlimiting examples of improving a skin condition include improving skin appearance and/or feel by providing a smoother, more even appearance and/or feel; increasing the thickness of one or more layers of the skin; improving the elasticity or resiliency of the skin; improving the firmness of the skin; and reducing the oily, shiny, and/or dull appearance of skin, improving the hydration status or moisturization of the skin, improving the appearance of fine lines and/or wrinkles, improving skin exfoliation or desquamation, plumping the skin, improving skin barrier properties, improve skin tone, reducing the appearance of redness or skin blotches, and/or improving the brightness, radiancy, or translucency of skin.

"Skin care active" means a compound or combination of compounds that, when applied to skin, provide an acute and/or chronic benefit to skin or a type of cell commonly found therein. Skin care actives may regulate and/or improve skin or its associated cells (e.g., improve skin elasticity, hydration, skin barrier function, and/or cell metabolism).

"Skin care composition" means a composition that includes a skin care active and regulates and/or improves skin condition.

"Synergy" and variations thereof mean that the cellular energy production and/or ECM repair effects provided by a combination of palmitoyl depeptide-7 (pal-KT) and acetyl tetrapeptide-11 [SEQ ID NO: 1] is more than the predicted additive effect of these ingredients alone. For example, synergy is demonstrated when upregulation of PPARA [SEQ ID NO: 2] and/or MSMO1 [SEQ ID NO: 3] is increased by a combination of pal-KT and acetyl tetrapeptide-11 [SEQ ID NO: 2] more than the calculated additive effects of these ingredients individually.

"Treatment period," as used herein, means the length of time and/or frequency that a material or composition is applied to a target skin surface.

"Upregulation" and variations thereof mean an increase in gene expression. Conversely, "downregulation" means a decrease in gene expression. Upregulation and downregulation, with respect to a particular gene, can be determined according to the Gene Modulation Assay described in more detail below.

Skin Care Composition

The novel skin care compositions herein are intended for topical application to human skin to improve cellular energy production and/or the health of the ECM. The present skin care compositions contain a safe and effective amount of palmitoyl dipeptide-7 (pal-KT) and acetyl tetrapeptide-11 (ac-PPYL) [SEQ ID NO: 1]. An effective amount of these two ingredients in combination has been shown to upregulate PPARA [SEQ ID NO: 2] and MSMO1 [SEQ ID NO: 3], which is believed to be involved in cellular energy production. See, Lopez-Leon, S et al. "Sports genetics: the PPARA gene and athletes' high ability in endurance sports. A systematic review and meta-analysis." Biology of sport vol. 33,1 (2016): 3-6. An effective amount of pal-KT and ac-PPYL [SEQ ID NO: 1] can also synergistically upregulate MSMO1 (SEQ ID NO: 3), which is believed to be involved in cholesterol synthesis, which is involved in the repair and renewal of the skin barrier. See, He M. et al, "The role of sterol-C4-methyl oxidase in epidermal biology." Biochim Biophys Acta. 2014 March; 1841(3):331-5.

It has been shown that PPARA and MSMO1 are downregulated as a result of dermal aging in skin (i.e., chronological aging and/or photo aging of the dermis). However, in some instances the combination of pal-KT and ac-PPYL [SEQ ID NO: 1] synergistically upregulates these genes and may even exhibit a synergy of factor of 1.2 or more (e.g., 1.3, 1.4, 1.5, 1.6, 1.7, 1.8, or 1.9 or more). The compositions herein may contain a weight ratio of pal-KT to ac-PPYL [SEQ ID NO: 1] of between 10:1 and 1:10 (e.g., 5:1 to 1:10, 5:1 to 1:5, 1:1 to 1:5, or 1:1 to 1:10).

The skin care compositions herein may be cosmetic compositions, pharmaceutical compositions, or cosmeceutical compositions, and may be provided in various product forms, including, but not limited to, solutions, suspensions, lotions, creams, gels, toners, sticks, sprays, aerosols, ointments, cleansing liquid washes and solid bars, pastes, foams, mousses, shaving creams, wipes, strips, patches, electrically-powered patches, hydrogels, film-forming products, facial and skin masks (with and without insoluble sheet), make-up such as foundations, eye liners, and eye shadows, and the like. In some instances, the composition form may follow from the particular dermatologically acceptable carrier chosen. For example, the composition (and carrier) may be provided in the form of an emulsion (e.g., water-in-oil, oil-in-water, or water-in-oil-in water) or an aqueous dispersion.

The compositions herein may be prepared by conventional methods of making topical skin care compositions. Such methods typically involve mixing of the ingredients in one or more steps to a relatively uniform state, with or without heating, cooling, application of vacuum, and the like. The compositions are preferably prepared such as to optimize stability (physical stability, chemical stability, photostability) and/or delivery of the active materials. This optimization may include appropriate pH (e.g., less than 7), exclusion of materials that can complex with the active agent and thus negatively impact stability or delivery (e.g., exclusion of contaminating iron), use of approaches to prevent complex formation (e.g., appropriate dispersing agents or dual compartment packaging), use of appropriate photostability approaches (e.g., incorporation of sunscreen/ sunblock, use of opaque packaging), etc.

Vitamin $B_3$ Compound

The compositions herein may optionally include a safe and effective amount of a vitamin $B_3$ compound. In some instances, the present compositions may contain 0.01% to 10%, by weight, of the vitamin $B_3$ compound, based on the weight or volume of the composition (e.g., 0.1% to 10%, 0.5% to 5%, or even 1% to %).

As used herein, "vitamin $B_3$ compound" means a compound having the formula:

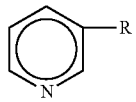

Where: R is $CONH_2$ (i.e., niacinamide), COOH (i.e., nicotinic acid) or $CH_2OH$ (i.e., nicotinyl alcohol); derivatives thereof; and salts of any of the foregoing.

Exemplary derivatives of vitamin $B_3$ compounds include nicotinic acid esters, including non-vasodilating esters of nicotinic acid (e.g., tocopheryl nicotinate, myristyl nicotinate) nicotinamide riboside, nicotinyl amino acids, nicotinyl alcohol esters of carboxylic acids, nicotinic acid N-oxide, and niacinamide N-oxide.

Dipeptide

The compositions herein include a safe and effective amount of the palmitoylated diopeptide, pal-KT (INCI: Palmitoyl Dipeptide-7). In some instances, pal-KT may be present in the present compositions at 0.0001% to 3% (e.g., 0.001% to 2%, 0.01% to 1% or 0.1% to 0.5%). Pal-KT is available as Palestrina® from Sederma (France).

Tetrapeptide

The compositions herein include a safe and effective amount of the acetylated tetrapeptide, ac-PPYL [SEQ ID NO: 2] (INCI: Acetyl Tetrapeptide-11). In some instances, ac-PPYL may be present in the present composition at 0.0001% to 3% (e.g., 0.001% to 2%, 0.01% to 1% or 0.1% to 0.5%). Ac-PPYL is available as SYNIORAGE from BASF Care Creations (New Jersey).

Dermatologically Acceptable Carrier

The compositions herein include a dermatologically acceptable carrier (which may be referred to as a "carrier"). The phrase "dermatologically acceptable carrier" means that the carrier is suitable for topical application to the keratinous tissue, has good aesthetic properties, is compatible with the actives in the composition, and will not cause any unreasonable safety or toxicity concerns. In one embodiment, the carrier is present at a level of from about 50% to about 99%, about 60% to about 98%, about 70% to about 98%, or, alternatively, from about 80% to about 95%, by weight of the composition.

The carrier can be in a wide variety of forms. In some instances, the solubility or dispersibility of the components (e.g., extracts, sunscreen active, additional components) may dictate the form and character of the carrier. Non-limiting examples include simple solutions (e.g., aqueous or anhydrous), dispersions, emulsions, and solid forms (e.g., gels, sticks, flowable solids, or amorphous materials). In some instances, the dermatologically acceptable carrier is in the form of an emulsion that has a continuous aqueous phase (e.g., an oil-in-water or water-in-oil-in-water emulsion) or a continuous oil phase (e.g., water-in-oil or oil-in-water-in-oil emulsion). The oil phase of the emulsion may include silicone oils, non-silicone oils such as hydrocarbon oils, esters, ethers, and mixtures thereof. The aqueous phase may include water and water-soluble ingredients (e.g., water-soluble moisturizing agents, conditioning agents, anti-microbials, humectants and/or other skin care actives). In some instances, the aqueous phase may include components other than water, including but not limited to water-soluble moisturizing agents, conditioning agents, anti-microbials, humectants and/or other water-soluble skin care actives. In some instances, the non-water component of the composition comprises a humectant such as glycerin and/or other polyol(s).

In some instances, the compositions herein are in the form of an oil-in-water ("O/W") emulsion that provides a sensorial feel that is light and non-greasy. Suitable O/W emulsions herein may include a continuous aqueous phase of more than 50% by weight of the composition, and the remainder being the dispersed oil phase. The aqueous phase may include 1% to 99% water, based on the weight of the aqueous phase, along with any water soluble and/or water miscible ingredients. In these instances, the dispersed oil phase will typically be present at less than 30% by weight of composition (e.g., 1% to 20%, 2% to 15%, 3% to 12%, 4% to 10%, or even 5% to 8%) to help avoid some of the undesirable feel effects of oily compositions. The oil phase may include one or more volatile and/or non-volatile oils (e.g., botanical oils, silicone oils, and/or hydrocarbon oils). Some nonlimiting examples of oils that may be suitable for use in the present compositions are disclosed in U.S. Pat. No. 9,446,265 and U.S. Publication No. 2015/0196464.

The carrier may contain one or more dermatologically acceptable diluents. As used herein, "diluent" refers to materials in which the skin care actives herein can be dispersed, dissolved, or otherwise incorporated. Some non-limiting examples of hydrophilic diluents include water, organic hydrophilic diluents such as lower monovalent alcohols (e.g., $C_1$-$C_4$) and low molecular weight glycols and polyols, including propylene glycol, polyethylene glycol (e.g., molecular weight of 200 to 600 g/mole), polypropylene glycol (e.g., molecular weight of 425 to 2025 g/mole), glycerol, butylene glycol, 1,2,4-butanetriol, sorbitol esters, 1,2,6-hexanetriol, ethanol, isopropanol, sorbitol esters, butanediol, ether propanol, ethoxylated ethers, propoxylated ethers and combinations thereof.

Conditioning Agents

The compositions herein may include 0.1% to 50% by weight of a conditioning agent (e.g., 0.5% to 30%, 1% to 20%, or even 2% to 15%). Adding a conditioning agent can help provide the composition with desirable feel properties (e.g., a silky, lubricious feel upon application). Some non-limiting examples of conditioning agents include, hydrocarbon oils and waxes, silicones, fatty acid derivatives, cholesterol, cholesterol derivatives, diglycerides, triglycerides, vegetable oils, vegetable oil derivatives, acetoglyceride esters, alkyl esters, alkenyl esters, lanolin, wax esters, beeswax derivatives, sterols and phospholipids, salts, isomers and derivatives thereof, and combinations thereof. Particularly suitable examples of conditioning agents include volatile or non-volatile silicone fluids such as dimethicone copolyol, dimethylpolysiloxane, diethylpolysiloxane, mixed C1-30 alkyl polysiloxanes, phenyl dimethicone, dimethiconol, dimethicone, dimethiconol, silicone crosspolymers, and combinations thereof. Dimethicone may be especially suitable, since some consumers associate the feel properties provided by certain dimethicone fluids with good moisturization. Other examples of silicone fluids that may be suitable for use as conditioning agents are described in U.S. Pat. No. 5,011,681.

Rheology Modifiers

The compositions herein may include 0.1% to 5% of a rheology modifier (e.g., thickening agent) to provide the composition with suitable rheological and skin feels properties. Some non-limiting examples of thickening agents include crosslinked polyacrylate polymers, polyacrylamide polymers, polysaccharides, gums and mixtures thereof. In a particularly suitable example, the composition may include a superabsorbent polymer thickening agent such as sodium polyacrylate, starch grafted sodium polyacrylate, or a combination of these. Some non-limiting examples of superabsorbent polymer thickeners are described in, for example, U.S. Pat. No. 9,795,552.

Some consumers find compositions that use silicone fluids as conditioning agents to be undesirably greasy or heavy feeling. Thus, it may be desirable to provide a composition that is free of or substantially free of silicone fluid. It may also be desirable to tailor a superabsorbent polymer thickener to provide the composition with a light, airy feel, for example, by adjusting the amount of water in the composition, the water:oil ratio (e.g., 12:1 to 1:1), and/or the ratio of water to thickener or oil to thickener.

Emulsifiers

When the dermatologically acceptable carrier is in the form of an emulsion, it may be desirable to include art emulsifier to provide a stable composition (e.g., does not phase separate). When included, the emulsifier may be present at an amount of 0.1% to 10% (e.g., 1% to 5%, or 2%-4%). Emulsifiers may be nonionic, anionic or cationic. Some non-limiting examples of emulsifiers that may be suitable for use herein are disclosed in U.S. Pat. Nos. 3,755,560; 4,421,769; and McCutcheon's Detergents and Emulsifiers, North American Edition, pages 317-324 (1986).

Other Optional Ingredients

The present composition may optionally include one or more additional ingredients commonly used in cosmetic compositions (e.g., colorants, skin care actives, anti-inflammatory agents, sunscreen agents, emulsifiers, buffers, rheology modifiers, combinations of these and the like), provided that the additional ingredients do not undesirably alter the skin health or appearance benefits provided by the present compositions. The additional ingredients, when incorporated into the composition, should be suitable for use in contact with human skin tissue without undue toxicity, incompatibility, instability, allergic response, and the like. Some nonlimiting examples of additional actives include vitamins, minerals, peptides and peptide derivatives, sugar amines, sunscreens, oil control agents, particulates, flavonoid compounds, hair growth regulators, anti-oxidants and/or anti-oxidant precursors, preservatives, protease inhibitors, tyrosinase inhibitors, anti-inflammatory agents, moisturizing agents, exfoliating agents, skin lightening agents, sunless tanning agents, lubricants, anti-acne actives, anti-cellulite actives, chelating agents, anti-wrinkle actives, anti-atrophy actives, phytosterols and/or plant hormones, N-acyl amino acid compounds, antimicrobials, and antifungals. Other non-limiting examples of additional ingredients and/or skin care actives that may be suitable for use herein are described in U.S. Publication Nos. 2002/0022040; 2003/0049212; 2004/0175347; 2006/0275237; 2007/0196344; 2008/0181956; 2008/0206373; 2010/00092408; 2008/0206373; 2010/0239510; 2010/0189669; 2010/0272667; 2011/0262025; 2011/0097286; US2012/0197016; 2012/0128683; 2012/0148515; 2012/0156146; and 2013/0022557; and U.S. Pat. Nos. 5,939,082; 5,872,112; 6,492,326; 6,696,049; 6,524,598; 5,972,359; and 6,174,533.

When including optional ingredients in the compositions herein, it may be desirable to select ingredients that do not form complexes or otherwise undesirably interact with other ingredients in the composition, especially pH sensitive ingredients like niacinamide, salicylates and peptides. When present, the optional ingredients may be included at amounts of from 0.0001% to 50%; from 0.001% to 20%; or even from 0.01% to 10% (e.g., 50%, 40%, 30%, 20%, 10%, 5%, 4%, 3%, 2%, 1%, 0.5% or 0.1%), by weight of the composition.

Method of Use

The present method includes identifying a target portion of skin where treatment is desired and applying a composition comprising an effective amount of vitamin $B_3$ compound, pal-KT, ac-PPYL [SEQ ID NO: 1] and, optionally, one or more additional skin care actives to the target portion of skin. The target portion of skin may be on a facial skin surface such as the forehead, perioral, chin, periorbital, nose, and/or cheek) or another part of the body (e.g., hands, arms, legs, back, chest). The person or target portion of skin in need of treatment may be one that exhibits a telltale sign of aging skin (e.g., fine lines, wrinkles, hyperpigmented spots). In some instances, a target portion of skin may not exhibit a sign of skin aging, but a user may still wish to treat the portion of skin if it is one that is known to exhibit visible signs of aging (e.g., skin that is exposed to the sun). In this way, the present methods and compositions may be used prophylactically to help delay the visible signs of skin aging.

The composition may be applied to a target portion of skin and, if desired, to the surrounding skin at least once a day, twice a day, or on a more frequent daily basis, during a treatment period. When applied twice daily, the first and second applications are separated by at least 1 to 12 hours. Typically, the composition is applied in the morning and/or in the evening before bed. The treatment period herein is ideally of sufficient time for the pal-KT and ac-PPYL [SEQ ID NO: 1] to improve the appearance of the skin. The treatment period may last for at least 1 week (e.g., about 2 weeks, 4 weeks, 8 weeks, or even 12 weeks). In some instances, the treatment period will extend over multiple months (i.e., 3-12 months). In some instances, the composition may be applied most days of the week (e.g., at least 4, 5 or 6 days a week), at least once a day or even twice a day during a treatment period of at least 2 weeks, 4 weeks, 8 weeks, or 12 weeks.

The step of applying the composition may be accomplished by localized application. In reference to application of the composition, the terms "localized", "local", or "locally" mean that the composition is delivered to the targeted area (e.g., a wrinkle or portion thereof) while minimizing delivery to skin surfaces where treatment is not desired. The composition may be applied and lightly massaged into an area of skin. The form of the composition or the dermatologically acceptable carrier should be selected to facilitate localized application. While certain embodiments herein contemplate applying a composition locally to an area, it will be appreciated that compositions herein can be applied more generally or broadly to one or more skin surfaces. In certain embodiments, the compositions herein may be used as part of a multi-step beauty regimen, wherein the present composition may be applied before and/or after one or more other compositions.

Gene Modulation Assay

This method provides a way to measure the ability of a compound or material to modulate the expression of a target gene such as PPARA [SEQ ID NO: 2] or MSMO1 [SEQ ID NO: 3].
Cells: tert keratinocytes (tKC)
BJ Fibroblasts
Plating: Cells are plated the day before treatment.
  For tert keratinocytes: 100,000 cells/well in 2 ml volume of medium/well for 12-well plates (e.g., Collagen I coated plates, Corning cat #356500), or 50,000 cells/well in 1 ml volume of medium/well for 24-well plates.
  For BJ fibroblasts: 88,000 cells/well in 2 ml volume of medium/well for 12-well plates (e.g., Corning cat #3512), or 44,000 cells/well in 1 ml volume of medium/well for 24-well plates.
Medium: For tert keratinocytes: EpiLife (e.g., Thermo Fisher Scientific cat #MEPI500CA+HKGS (e.g., Thermo Fisher Scientific cat #S-001-5).
  For BJ Fibroblasts: EMEM (e.g., ATCC cat #30-2003)+ 10% FBS (e.g., HyClone cat #SH30071.02).
Treatments are made in media and aliquoted to dose plates. When it is time to treat cells, all plates of cells are removed from the incubator at the same time. Working with one plate at a time, media is removed and treatment is added, as follows:
  Media is decanted from plate of cells.
  Inverted plate is blotted briefly on paper towels.
  Lid is put back onto plate and plate is moved into biosafety cabinet.
  Treatments are transferred from dose plate to plate of cells, one column at a time, using a multichannel pipette.
Once all plates have been treated, they are moved into incubator at 37° C., with 5% $CO_2$ and 90% humidity. About 15-30 min before the end of the treatment period, cells from representative wells of each treatment are observed via microscope, then plates are returned to the incubator. When treatment time is complete, all plates are removed from incubator. Media is decanted from each plate, and plates are blotted on paper towels. 350 ul Qiagen Buffer RLT is added to each well to lyse cells, and lysates are transferred to 2 ml Eppendorf tubes and stored at −20° C. until ready for genomics.

Wafergen Process: Total RNA Purification and qPCR

Cell lysates are thawed at 4° C. and then isolated using the Biomek FxP and the RNAdvance Tissue Isolation kit (Beckman Coulter, p/n A32646). The resulting RNA is quantified using the Nandrop 8000 (Nanodrop, ND-8000). cDNA is generated using 500 ng of Total RNA and Applied Biosystems High Capacity cDNA with Reverse Transcription kit (Applied Biosystems p/n 4368814). cDNA, assays, and dilutions of PrimeTime GeneExpression MasterMix (IDT, p/n 1055771) are plated onto a Wafergen MyDesign SmartChip (TakaraBio, p/n 640036) using the Wafergen Nanodispenser. The chip is then loaded into the SmartChip cycler and qPCR performed using the following PCR conditions:
  Hold stage: 50° C. for 2 minutes (warm up), then 95° C. for 10 minutes.
  PCR stage (40 cycles): 95° C. for 15 seconds, then 60° C. for 1 minute. Export data in .txt file format for analysis.

Hydrogen Peroxide Stressed ATP Assay

Skin Cells (e.g., keratinocytes and fibroblasts) fight reactive oxygen species by using energy to generate enzymes and reducing equivalents (e.g., GSH), which causes a depletion of cellular ATP levels. Lower energy levels leave the cells susceptible to decreased ability to adapt and function normally. Thus, increasing cellular ATP levels may help the cells fight off stress and maintain sufficient energy for normal homeostasis.

Hydrogen peroxide is a well-known surrogate for ROS. When skin cells are treated with high levels (e.g., 200-500 uM) of hydrogen peroxide, a decrease of about 10% in cellular ATP level is observed in non-stressed cells in an hour. Cellular ATP levels can be quantitated with a CELL TITER GLO brand assay kit from Promega, or equivalent, in which a luminescence signal is proportional to the quantity of ATP present.
Summary of Method:
  The assay is performed using expanded tKCs from storage stocks. The cells are expanded over 5 days in culture flasks, trypsinized, seeded and then grown in 96-well plates. After growing for 1 day in 96-well plates, column 1 cells are not treated nor stressed, columns 2-12 of the cells are treated with hydrogen peroxide (300 uM in media), column 2 is not treated with test materials while columns 3-12 are treated with serial dilutions of test materials for 1 hour (37° C., 5% $CO_2$ incubator).
Cell Preparation:
  1. Seed cells at 10,000 cells/well in 100 uL total volume/well in suitable 96-well plates (e.g., CORNING brand white, clear bottom plates, #3903 or equivalent).
  2. Incubate cells for 24 hours at 37° C., 5% $CO_2$, 95% humidity until treatment day. For example, cells can be seeded on Monday and assayed on Tuesday.
Treatment:
  1. Aspirate the media from the cell plates.
  2. Add 100 uL medium to column 1 wells A1-H1.
  3. Add 100 uL medium containing 300 uM hydrogen peroxide to all wells in columns 2-12.
  4. Add vehicle control to column 2 (A2-H2) and 1 uL of serial dilutions of treatments to columns 3-11.
  5. Add 1 ul of 40.9 mM niacinamide to all wells in column 12 making final level of niacinamide 409 uM (positive control).
  6. Place in 37° C., 5% $CO_2$ incubator for 1 hour.
  7. Aspirate media from all wells.
  8. Add 100 uL of CELL TITER GLO brand reagent to each well per manufacturer instructions.
  9. Incubate at room temperature for 5-10 minutes.
  10. Read luminescence on a suitable plate reader.

Luminescence Detection:

Use SYNERGY NEO brand plate reader from BioTek or equivalent.

EXAMPLES

Example 1: Formulations

Table 1 below provides examples of the present skin care compositions. The exemplary compositions are made by blending the A phase components with a suitable mixer (e.g., Tekmar RW20DZM or equivalent) and heating to a temperature of 70-80° C. and maintaining the temperature while stirring. Separately, the B phase components are blended with a suitable mixer and heated to 70-75° C., while maintaining temperature during mixing. Phase B is added to Phase A while mixing well to form an oil-in-water (O/W) emulsion. The emulsion is then milled using a suitable mill (e.g., Tekmar T-25 or equivalent) for 5 minutes. When the emulsion is at 60° C., phase C is added while continuing to mix. At 40° C., the ingredients of phase D and E are added to the emulsion. The emulsion is then milled for 5 minutes to provide a uniform composition.

TABLE 1

| Component | I | II | III | IV | V | VI | VII | VIII | IX |
|---|---|---|---|---|---|---|---|---|---|
| Phase A | | | | | | | | | |
| Water | qs | qs | qs | qs | qs | qs | qs | qs | qs |
| Glycerol | 5.00 | 7.00 | 3.00 | 15.0 | 7.00 | 5.00 | 5.00 | 3.00 | 5.00 |
| Disodium EDTA | 0.10 | 0.05 | 0.10 | 0.10 | 0.05 | 0.05 | 0.05 | 0.05 | 0.10 |
| Phase B | | | | | | | | | |
| Dimethicone 5 cSt | — | — | — | — | — | — | — | 10.0 | 15.0 |
| Dimethicone and Dimethicone Crosspolymer | — | — | — | — | — | — | — | 13.0 | 15.0 |
| Laureth-4 | — | — | — | — | — | — | — | 0.25 | 0.35 |
| Polysorbate 20 | — | — | — | — | — | — | — | 0.15 | 0.25 |
| Tapioca Starch and Polymethylsilsesquioxane | — | — | — | — | — | — | — | 2.50 | 3.50 |
| Avobenzone | — | — | — | 3.00 | — | 3.00 | — | — | — |
| Homosalate | — | — | — | 15.0 | — | 10.0 | — | — | — |
| Octisalate | — | — | — | 5.00 | — | 5.00 | — | — | — |
| Octocrylene | — | — | — | 2.60 | — | 9.00 | — | — | — |
| Isopropyl Isostearate | 5.00 | 2.50 | 1.00 | — | — | — | — | — | — |
| Isohexadecane | 1.00 | 1.50 | 3.00 | — | — | — | — | — | — |
| Cetyl Alcohol | 0.25 | 0.50 | 0.32 | 0.40 | 0.40 | 0.30 | 0.50 | — | — |
| Tocopherol Acetate | — | 0.50 | 0.25 | 1.00 | 0.25 | 0.25 | 0.25 | — | — |
| PEG-100 Stearate | 0.20 | 0.10 | 0.10 | 0.30 | 0.10 | 0.20 | 0.10 | — | — |
| Stearyl Alcohol | 0.50 | 1.50 | 0.40 | 0.60 | 0.50 | 0.40 | 0.60 | — | — |
| Behenyl Alcohol | 0.40 | 1.00 | 0.50 | 0.50 | 0.40 | 0.35 | 0.50 | — | — |
| Ethyl Paraben | 0.20 | 0.15 | 0.20 | 0.25 | — | — | — | — | — |
| Propyl Paraben | 0.10 | 0.15 | 0.10 | 0.15 | — | — | — | — | — |
| Polymethylsilsesquioxane | 1.25 | 2.50 | 1.00 | — | — | — | — | — | — |
| Phase C | | | | | | | | | |
| Titanium Dioxide | — | 0.50 | — | 0.25 | — | — | — | — | — |
| Tapioca Starch and Polymethylsilsesquioxane | — | — | — | — | — | 12.0 | — | — | — |
| Vinyl Dimethicone/Methicone Silsesquioxane Crosspolymer | 1.50 | — | 1.50 | 3.50 | 5.00 | — | 7.50 | — | — |
| Sodium Polyacrylate Starch | — | — | — | — | 1.50 | 1.00 | 1.50 | — | — |
| Hydroxyethyl acrylate/sodium acryloyldimethyltaurate copolymer | 2.00 | 1.50 | 2.50 | 2.00 | — | — | — | 1.25 | 2.00 |
| Phase D | | | | | | | | | |
| Water | 5 | 10 | 10 | 5 | 10 | 10 | 10 | 5 | 10 |
| Pal-KT | 0.00005 | 1 | 0.5 | 0.1 | 0.05 | 0.025 | 0.01 | 0.005 | 0.0005 |
| Ac-PPYL | 0.00005 | 1 | 5 | 1 | 0.1 | 0.005 | 0.05 | 0.0005 | 0.005 |
| Niacinamide | 3.5 | — | 3.5 | — | 4 | 5 | — | — | 2 |
| Dexpanthenol | 0.5 | 0.5 | 0.5 | 1 | 1 | 1.5 | 0.25 | 1 | 0.5 |
| Phase E | | | | | | | | | |
| Benzyl alcohol | 0.25 | 0.40 | 0.25 | 0.50 | — | — | — | — | — |
| Hexanediol and Caprylyl Glycol | — | — | — | — | 0.70 | 0.80 | 0.70 | 0.70 | 1.00 |
| Phenoxyethanol | — | — | — | 0.3 | 0.4 | 0.5 | 0.20 | 0.25 | — |
| Dimethicone/dimethiconol | 0.5 | 1.00 | 2.00 | 1.00 | 2.00 | 2.00 | 1.00 | 1.75 | 1.00 |

Example 2: pal-KT and Ac-PPYL [SEQ ID NO: 1] Synergistically Upregulate PPARA [SEQ ID NO: 2] and MSMO1 [SEQ ID NO: 3]

This example demonstrates the ability of a combination of pal-KT and ac-PPYL [SEQ ID NO: 1] to synergistically upregulate PPARA [SEQ ID NO: 2]. Test compositions and control compositions were prepared as described above in the Gene Modulation Assay and tested accordingly. The pal-KT used in this example is PALESTRINA brand pal-KT from Sederma (France), and the ac-PPYL is SYNIORAGE brand tetrapeptide from BASF Care Creations (New Jersey). The results of the test are summarized below in Table 2. P+A refers to the combination of pal-KT (P), and ac-PPYL (A) [SEQ ID NO: 1].

Synergy Factor is calculated as:

$$\frac{\text{Observed response for the combination of ingredients}}{\text{Sum of the individual ingredient responses}}$$

A synergy factor greater than 1.00 with p-value ≤0.05 indicates a statistically significant synergistic effect. Preferred synergy factors are 1.3 or greater.

TABLE 2

| Peptide amount (ppm) | | | Fold change vs. control | | | | | |
|---|---|---|---|---|---|---|---|---|
| Pal-KT | Ac-PPYL | Biomarker | Pal-KT | Ac-PPYL | P + A (expected) | P + A (observed) | Synergy factor | P-value |
| 15 | 40.5 | MSMO1 | 5.63 | 0.560 | 9.62 | 3.15 | 3.06 | 4.46E−14 |
| 15 | 13.5 | MSMO1 | 5.63 | 0.510 | 5.84 | 2.87 | 2.04 | 1.14E−07 |
| 15 | 1 | MSMO1 | 5.63 | 0.496 | 5.25 | 2.79 | 1.88 | 1.71E−06 |
| 15 | 0.0135 | MSMO1 | 5.63 | 0.377 | 4.26 | 2.12 | 2.01 | 1.86E−07 |
| 7.5 | 40.5 | MSMO1 | 4.69 | 0.560 | 7.49 | 2.62 | 2.86 | 3.61E−12 |
| 7.5 | 13.5 | MSMO1 | 4.69 | 0.510 | 5.01 | 2.39 | 2.10 | 1.31E−07 |
| 7.5 | 1 | MSMO1 | 4.69 | 0.496 | 3.41 | 2.32 | 1.47 | 2.28E−03 |
| 7.5 | 0.0135 | MSMO1 | 4.69 | 0.377 | 2.58 | 1.77 | 1.46 | 8.57E−03 |
| 1 | 40.5 | MSMO1 | 4.32 | 0.560 | 6.24 | 2.42 | 2.58 | 2.63E−09 |
| 1 | 13.5 | MSMO1 | 4.32 | 0.510 | 2.27 | 2.20 | 1.03 | 8.11E−01 |
| 1 | 1 | MSMO1 | 4.32 | 0.496 | 2.50 | 2.14 | 1.17 | 2.15E−01 |
| 1 | 0.0135 | MSMO1 | 4.32 | 0.377 | 1.84 | 1.63 | 1.13 | 3.54E−01 |
| 15 | 40.5 | PPARA | 1.59 | 0.71 | 2.09 | 1.13 | 1.85 | 1.33E−03 |
| 15 | 13.5 | PPARA | 1.59 | 0.67 | 1.79 | 1.07 | 1.67 | 6.02E−03 |
| 15 | 1 | PPARA | 1.59 | 0.69 | 2.54 | 1.09 | 2.33 | 1.23E−05 |
| 15 | 0.0135 | PPARA | 1.59 | 0.70 | 1.60 | 1.11 | 1.44 | 4.98E−02 |
| 7.5 | 40.5 | PPARA | 1.43 | 0.71 | 0.94 | 1.02 | 0.93 | 6.96E−01 |
| 7.5 | 13.5 | PPARA | 1.43 | 0.67 | 1.35 | 0.96 | 1.40 | 7.97E−02 |
| 7.5 | 1 | PPARA | 1.43 | 0.69 | 1.18 | 0.98 | 1.21 | 2.97E−01 |
| 7.5 | 0.0135 | PPARA | 1.43 | 0.70 | 1.15 | 1.00 | 1.15 | 5.04E−01 |
| 1 | 40.5 | PPARA | 1.26 | 0.71 | 1.09 | 0.90 | 1.22 | 3.61E−01 |
| 1 | 13.5 | PPARA | 1.26 | 0.67 | 0.81 | 0.85 | 0.95 | 7.93E−01 |
| 1 | 1 | PPARA | 1.26 | 0.69 | 0.86 | 0.86 | 1.00 | 9.79E−01 |
| 1 | 0.0135 | PPARA | 1.26 | 0.70 | 0.63 | 0.88 | 0.72 | 9.12E−02 |

As can be seen in Table 2, not all combinations of pal-KT and ac-PPYL [SEQ ID NO: 1] yield the desired synergistic effect Test sample combinations containing 1 ppm pal-KT at a ratio of pal-KT to tetrapeptide of 1:13.5 to 100:1.35 did not exhibit a synergy factor of 1.3 or greater for upregulating MSMO1 [SEQ ID NO: 3]. Test sample combinations containing 7.5 ppm pal-KT only exhibited the desired synergy to upregulate PPARA [SEQ ID NO: 2] at a ratio of about 1:2, even though other combinations exhibited a lesser ability to synergistically upregulate PPARA [SEQ ID NO: 2]. Only one of the test samples containing 1 ppm were able to synergistically upregulate PPARA [SEQ ID NO: 2] and none of the test samples exhibited a synergy factor of 1.3 or greater. Thus, the data suggest that both the concentration of peptide and the ratio of the peptide can be important for upregulating PPARA [SEQ ID NO: 2] and MSMO1 [SEQ ID NO: 3].

Example 3: pal-KT and ac-PPYL [SEQ ID NO: 3] Improve Cellular Bioenergetics

This example demonstrates the ability of pal-KT and ac-PPYL [SEQ ID NO: 3] to combat ROS-induced ATP depletion. Test cells exposed to hydrogen peroxide, a well-known reactive oxygen species, will generally exhibit reduced ATP levels. Test agents that can restore ATP levels depleted by exposure to the ROS are desirable. Test agents that can synergistically restore ATP levels and exhibit a synergy factor of 1.3 or greater are preferred. The peptides were tested according to the Hydrogen Peroxide Stressed ATP assay above. The results of the test are summarized below in Table 3. A synergy factor greater than 1.00 with p-value ≤0.05 indicates a statistically significant synergistic effect. Preferred synergy factors are 1.3 or greater.

TABLE 3

| ROS-induced ATP restoration | | | | |
|---|---|---|---|---|
| Ratio of pal-KT to ac-PPYL | Luminescence P + A (measured) | Luminescence P + A (calculated) | Synergy factor | p-value |
| 100:1 | 18655 | 19547 | 0.95 | 0.4508 |
| 10:1 | 18271.33 | 19529 | 0.94 | 0.0810 |
| 1:1 | 16946.33 | 10547 | 1.61 | 0.0004 |
| 1:10 | 13446 | 9390 | 1.43 | 0.0076 |
| 1:100 | 12044 | 12156.33 | 0.99 | 0.7825 |

As can be seen in Table 3, not all combinations of pal-KT and ac-PPYL [SEQ ID NO: 1] can synergistically restore ROS-depleted ATP levels in a cell. Indeed, only combinations containing pal-KT and ac-PPYL at a ratio of between about 10:1 and 1:10 were able to synergistically increase ATP production. In this example, test samples with a ratio of pal-KT to ac-PPYL [SEQ ID NO: 1] of about 1:1 appear to exhibit the highest synergy factor.

Example 4: Dipeptide Specificity

This example demonstrates the importance of selecting a specific dipeptide to provide the desired synergistic upregulation of PPARA [SEQ ID NO: 2] and/or MSMO1 [SEQ ID NO: 3]. In this test, the amino acids from pal-KT were rearranged to form a new dipeptide, pal-TK. Test compositions and control compositions were prepared as described above in the Gene Modulation Assay and tested accordingly. The results of the test are summarized in Table 4 below. Fold change factor is calculated as.

$$\frac{\text{fold change of } pal-KT + ac-PPYL}{\text{fold change of } pal-TK + ac-PPYL}$$

A fold change factor of greater than 1 is desired, and a fold change factor of 1.3 or greater is preferred.

Surprisingly, pal-KT was able to upregulate PPARA [SEQ ID NO: 2] and MSMO1 [SEQ ID NO: 3] significantly better than pal-TK and exhibited a fold change factor of greater than 1.3 for upregulating both PPARA [SEQ ID NO: 2] and MSMO1 [SEQ ID NO: 3]

TABLE 4

Specificity of pal-KT to pal-TK

| Biomarker | Fold change vs. control (all peptides at 1 ppm) | | Fold change factor | p-value |
|---|---|---|---|---|
| | pal-KT + ac-PPYL | pal-TK + ac-PPYL | | |
| PPARA | 1.56 | 1.04 | 1.50 | 2.54E–05 |
| MSMO1 | 2.34 | 1.32 | 1.78 | 4.06E–07 |

Surprisingly, as can be seen in Table 4, a dipeptide with the same amino acids as pal-KT, but arranged in a different order, does not provide the desired synergistic effect. These data suggest that the specific peptide sequence is important for providing the desired synergy.

Example Combinations

A. A skin care composition, comprising:
a) a combination of palmitoyl dipeptide-7 (pal-KT) and acetyl tetrapeptide-11 (ac-PPYL) [SEQ ID NO: 1], wherein the combination of pal-KT and ac-PPYL [SEQ ID NO: 1] upregulates at least one of PPARA (SEQ ID NO: 2) and MSMO1 (SEQ ID NO: 3); and
b) a dermatologically acceptable carrier.
B. The composition of paragraph A, wherein the combination of pal-KT and ac-PPYL [SEQ ID NO: 1] synergistically upregulates at least one of PPARA (SEQ ID NO: 2) and MSMO1 (SEQ ID NO: 3).
C. The composition of paragraph A or B, wherein the combination of pal-KT and ac-PPYL [SEQ ID NO: 1] exhibits a synergy factor of at least 1.3.
D. The composition of any preceding paragraph, wherein the pal-KT is present at 0.00005% to 5%.
E. The composition of any preceding paragraph, wherein the ac-PPYL [SEQ ID NO: 1] is present at 0.00005% to 5%.
F. The composition of any preceding paragraph, wherein the pal-KT and ac-PPYL [SEQ ID NO: 1] are present at a ratio of between 10:1 and 1:10.
G. The composition of any preceding paragraph, further comprising at least one additional ingredient selected from vitamins, minerals, peptides, sugar amines, sunscreen agents, oil control agents, flavonoid compounds, anti-oxidants, protease inhibitors, tyrosinase inhibitors, anti-inflammatory agents, moisturizing agents, exfoliating agents, skin lightening agents, anti-acne agents, anti-wrinkle agents, phytosterols, N-acyl amino acid compounds, antimicrobials, antifungals, pH adjustors, thickening agents, preservatives, and combinations thereof.
H. The composition of paragraph G, wherein the additional ingredient comprises a vitamin B3 compound, a vitamin A compound, a vitamin E compound, a saccharide, or a botanical extract.
I. A method of cosmetically treating skin, comprising:
a) identifying a target portion of skin where treatment is desired; and
b) applying the skin care composition of any preceding paragraph to the target portion of skin over the course of a treatment period, the skin care composition comprising a combination of palmitoyl dipeptide-7 (pal-KT) and acetyl tetrapeptide-11 (ac-PPYL) [SEQ ID NO: 1]) and a dermatologically acceptable carrier.
J. The method of paragraph I, wherein the combination of pal-KT and ac-PPYL [SEQ ID NO: 1] upregulates at least one of PPARA [SEQ ID NO: 2] and MSMO1 [SEQ ID NO: 3], preferably the combination of pal-KT and ac-PPYL [SEQ ID NO: 1] synergistically upregulates at least one of PPARA [SEQ ID NO: 2] and MSMO1 [SEQ ID NO: 3].
K. The method of paragraph I, wherein the combination of pal-KT and ac-PPYL [SEQ ID NO: 1] improves cellular ATP level, preferably synergistically improves cellular ATP level, according to the Hydrogen Peroxide Stressed ATP assay.
L. The method of paragraph I, wherein the treatment period is at least 2 weeks.
M. The method of paragraph, wherein the method improves a visible sign of skin aging.
N. A method of synergistically upregulating at least one of PPARA [SEQ ID NO: 2] and MSMO1 [SEQ ID NO: 3] in a skin cell, comprising: contacting a skin cell with an effective amount of pal-KT and ac-PPYL [SEQ ID NO: 1] in combination, wherein the effective amount of pal-KT and ac-PPYL [SEQ ID NO: 1] upregulates at least one of PPARA [SEQ ID NO: 2] and MSMO1 [SEQ ID NO: 3].

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A skin care composition, comprising:
    a) a combination of palmitoyl dipeptide-7 (pal-KT) and acetyl tetrapeptide-11 (ac-PPYL) [SEQ ID NO: 1]; and
    b) a dermatologically acceptable carrier;
    wherein the combination of pal-KT and ac-PPYL [SEQ ID NO: 1] synergistically upregulates at least one of PPARA (SEQ ID NO: 2) and MSMO1 (SEQ ID NO: 3) and exhibits a synergy factor of at least 1.3;
    wherein the pal-KT and ac-PPYL [SEQ ID NO: 1] are present at a ratio of between about 10:1 and 1:10.

2. The composition of claim 1, wherein the combination of pal-KT and ac-PPYL [SEQ ID NO: 1] improves cellular ATP level, according to the Hydrogen Peroxide Stressed ATP assay.

3. The composition of claim 2, wherein the combination synergistically improves cellular ATP level.

4. The composition of claim 3, wherein the combination exhibits a synergy factor of at least 1.3.

5. The composition of claim 1, wherein the pal-KT is present at about 0.00005% to about 5%.

6. The composition of claim 1, wherein the ac-PPYL [SEQ ID NO: 1] is present at about 0.00005% to about 5%.

7. A method of cosmetically treating skin, comprising:
    a) identifying a target portion of skin where treatment is desired; and
    b) applying the skin care composition of claim 1 to the target portion of skin over the course of a treatment period.

8. The method of claim 7, wherein the combination of pal-KT and ac-PPYL [SEQ ID NO: 1] synergistically improves cellular ATP level, according to the Hydrogen Peroxide Stressed ATP assay.

9. The method of claim 8, wherein the combination exhibits a synergy factor of at least 1.3.

10. The method of claim 7, wherein the pal-KT is present at about 0.00005% to about 5%.

11. The method of claim 7, wherein the ac-PPYL [SEQ ID NO: 1] is present at about 0.00005% to about 5%.

12. The method of claim 7, wherein the treatment period is at least 2 weeks.

* * * * *

SEQUENCE LISTING

```
<160> NUMBER OF SEQ ID NOS: 3

<210> SEQ ID NO 1
<211> LENGTH: 4
<212> TYPE: PRT
<213> ORGANISM: Artificial Sequence
<220> FEATURE:
<223> OTHER INFORMATION: Description of artificial sequence: acetyl
      tetrapeptide-11 (ac-PPYL)

<400> SEQUENCE: 1

Pro Pro Tyr Leu
1

<210> SEQ ID NO 2
<211> LENGTH: 93231
<212> TYPE: DNA
<213> ORGANISM: Homo sapiens

<400> SEQUENCE: 2
gtggacgcgg cggccccgcg gcggggcag cgggcggcgg gggcggaggc ggccgctagc      60
gccctgcccg gcgccgcctc cttcggcgtt cgccccacgg accggcaggc ggcggaccgc     120
ggcccaggtg cccgggggcg ggcggcggg cgggcgggaa cgcgcgcggg ggtccgcggt     180
ccgggcttcc caggtcccgg gacccgagg gcggcggacg ggggagggc aggggctggg     240 cggcgcatgc gcggggcccg gggtctcggg gtctccgggt cccggggacc cggggccccg     300
gggtgcgcgg ctggggacct gagggcgagg agcgaggaca cacaccgagg actcttgcga     360
gggatctcgg ggcccagctc ggcctccctc ctagcgctgg gggcctgccc ggaacccgag     420
tccgcggctg tccctggggt ttggcgctgc gcggaggtcg ggtctgggga ccgcagcgac     480
tctgggtctt cgggttgtcc cctcggaggg aggggcccacg ggcggggaca tcgggacttg     540
ccctttcctc ggcgcagcgg agctgggggcg tcgccgactc agaaggtgct ttccgagacc     600
tccagggatc tccgaggcga ggaaacccgg gccccggaca gaccgaccct gggtgggtgc     660
gcccggcttc tgccgtcgga cggagacgcg cgtgtttgtt cctccagctg cgaccacctt     720
tgaggaacgg ttcccacttt gtgccccaac gcggcggggc gaccccggac aggctgcgct     780
gggccgggtg gcttctctgc ggaagccgcg ccacgtcgct cccggtcggg gccgctgagg     840
gtcgggcgcc caggtctttc cggagtcccg ggctgcgcgg cccgcgtggt gcgggtgaag     900
ctggaggggc gcggggtggt gccagtggaa gtcaggaggg tcggccctgc cccctcacgc     960 acccccaaccg ggcacaactg cacgcctgtg cttttctgaa gtctttttta aaagttaaaa    1020
gagaggaagt gtgctccaag tgtcaggatt ctttccaaga aaaacccaca gttgtccaat    1080
ggcctgggct tcgtgggacc tccggggctg cacgcccacg tcagcctcag ccgacccctg    1140
ccaggaaacc agggaggccc ctcctctccc agcctccttg ggataagggt gccttgggga    1200
actgggtcag ggcaaggaca cgggattttc ctgggaagga ccctgcgaca cccgtgtcgt    1260
tgcggggcag ggtcagcatg actttcctct tccaaggtga agagttgggg ggcatccaga    1320
```

```
gaacaaccgt aatcacttcc tccttcacct tcttactgcc aggctgaagc tcagggccct    1380
gtctgctctg tggactcaac agtttgtggc aagacaagct cagaactgag aagctgtcac    1440
cacaggtaaa tagaaggttt aatttactgt ttccagatgg aaatatttaa gtgttttcag    1500
tgtttacttc tgttgcacta cagaccagca atctgggggt tattactttg tgatgcaagg    1560
ttagatacgt tttcagactg aaagtaaaat acatgtgcat ggattcattt tttttttttt    1620
tttttttttt tgagacggag tctcgctctg ccgcccaggc tggagtgcag tggcctaatc    1680
tcagatcaca gcaacctctg ccactgggt tcaagcgatt ctcttgcctc agcctcccga     1740
gtagctggga ttacaggcgc ctgccaccat gcccagctaa tttttgtagt tttagtagag    1800
gcggggtttc accatcttgg ccaggctgat cttgaactcc tgacctcatg atccacctgt    1860
tcctcccaaa gtgctgggat tacagacgtg agccaccgtg cctggcctag gattcacttt    1920
gaagttctga gttattgtgt gacttttgct aggaacttca ttgcttcgtg gcaggcatgt    1980
tttgtataat ttaaaacttg atgacattaa ctttgagaaa cgtgagtgct tactagaccc    2040
ttgggatgtc cacactgact ggtaccgagt agtgtactgt tctgagctg ttttcatttt     2100 gatttgaata ttaagcagat ggcttcttga gatagacccg tgccagaaca tgccagggat    2160
aggctgaaga aacgggccag atgatacaaa tttgtgtggt caccatccat gagagaccag    2220
ggacactggg gctgatgatg acctctgcaa ctctgaagca aaagtaaact aattggcaag    2280
ttgggtgcgg tggctcactc ctgtaatccc agcactttgg aagctgggt gggcagatcg     2340 cttgaggcca ggagttcgag accagcctgg ccaacatggt gaaaccttgt ctctacaaaa    2400
aaatagaaat attgcctggg catggtggcg gacatctgta atcccagcta ctcaagaaac    2460
tgaggcagga gaatcgcttg agcctgggag gtgaaggttt tagtgaactg agattgtgcc    2520
actgcactgc agcctgggcg ccagggcgag actccgtctc aaaaataaat aaataaaata    2580
aaattaatta actaattgac attagaaaaa aatgtttttt ctttcttttc ccacatcctt    2640
tttttttttt tttttttttt tgtgacagag ttttgctctt gtcacccagg ctggagtgca    2700
gtggcatgat cttggctcac cgcaacgtcc acctcacgga ttcgaacaat actcctgcct    2760
cagcctcccg agtagctggg attacaggca ctcaccacca cacccggcta attttttgtat   2820 ttttagtaga ggtgggtttc accatgttgg ctgggctggt ctcaaactcc tgacctcagg    2880
tgaaccgcct gccttggcct cccaaagggc tgaggttaca ggtgcgagcc accgcgccgg    2940
gcccttttcc gacatcttaa acgtaaagta ggagacgtgt cataatcatc gaatactgca    3000
gtggttttca ttagctcctg tttgtcaaac ttatgaacag agttttaaaa attgtgtatc    3060
agccgggtgc ggtggctcac acctgtaatc tttgggaggc tgaggtgggc agatgacaag    3120
atcaggagtt tgagaccagc ctggccaata tggtgaaacc ctgtctctac taaaaataca    3180
aaaattagct gggcatggtg gcgggtgcct atggtcccag ctactcagga ggctgaagca    3240
ggagaatctc ttgaacccgg gaggtggagg ttgcagtgag ctgagatggc accacagcac    3300
cccagcctgg gtgacagagc aagactccgt ttccaaaaaa aaaaaattgt atatgagaga    3360
gacagaacta gacagagaag aaggagaaaa tgtgtcttct ttatacacta ttttgtaact    3420
tgctttatcg agtaggttat gaaaaatctt cctatgtgaa aaacatttct gcatcatttg    3480
aaatgtctat ataatatccc attgtgttta gatacaataa tatttagcca atctctttat    3540
gtgtatatat ttaatacagt cattctataa atattgactg agtagctgct gtgggctact    3600
gtccgcagtg ctgaacaaga caagcatgaa tccatgaaac tgattttcat accagaatat    3660
aaaaaagaaa cttaaagata atcctcatca tggtaaaaga tgaagaacct attttttgccg   3720
```

| | |
|---|---|
| ggacatctta ctctttagta attggtggcc agtgttcttt tcttgcatg ctgttttgga | 3780 |
| gagtctgttt tttaaataaa tatttaagta gcctgggcgc agtggctcac gcctatggtt | 3840 |
| tcagcacttt gtgaggccga aggggatgga ttgcttgagc ccagggcttc aagaccagcc | 3900 |
| tgggcaacct ggcgaaaccc tgcatctact aaaaatacaa aaattagcca ggtatagtgg | 3960 |
| cgtgtgcctg tggccccatc tacttgggag gctgaggtgg gaggatccct tgagcctgag | 4020 |
| aagtggaggt tgcagtgact gagatggcac cactacactc cagcctgggt gacagagtga | 4080 |
| gacctggtct caaaaaataa ataaatattt atgtaatcat ctttaagcag tgttttaat | 4140 |
| tttatttatt tatttattta ttttgagac agggtctcac tgtgtcacct aggctagagc | 4200 |
| acagctgcat gatcacggcc tattgcagcc tcgacctccc tgggctcagg tgatcctccc | 4260 |
| acctcagcct cccaagcagc taggaccaca ggcacacgcc accaggcctg actcatttt | 4320 |
| gtattttttg cagagacggg gtcttgctat gttgttcaga cctgtctcaa actcctgggc | 4380 |
| tcaagccatc ctcctgcctc ggcctcccat agtgctggga ctaagccatg aaccactgca | 4440 |
| cccggcataa gtggtctttc tttaaaaaaa aaaaaaaaa aaaaaaaaa aaaaaaaaa | 4500 |
| aaccacatta attaaaatat gtatttgctt attataaata tatttgaaac atgccaattt | 4560 |
| ttcttctctt tttttgctct attggtttct gtgtgtggat ggatatattt ttaatggcaa | 4620 |
| ataggatgag tgtctttact tccaagtagt cagtgttttt ctttaatgtt tgtactaatt | 4680 |
| ttgtcacatt gcagttagag gttgtggcct gtctaatttc tgcttttttg gaacttgaga | 4740 |
| gtctctgttt ttatttgttt ttggtagcct ggcatagagt ccattttct tttcttttct | 4800 |
| tttttgaga cggagtttag ctcttgttgc ccagactggc gtgcagtggc gcaatctcag | 4860 |
| ctcactgcaa cctccgcctc ctgggttcaa gcgattctcc tgcctcagtc tccccagtag | 4920 |
| ctgggattac aggtgcccac caccacacct ggctattttt tgtattttta gtagagacgg | 4980 |
| ggttttgcca tgttggccag gctggtctcg aactcctgat ctcaggtgat ccacccgcct | 5040 |
| cggcctccca aagtgctggg attacaggtg tgagccactg cgcccagctg tagatacttt | 5100 |
| ttaaaaggt atagtttctg attatggggt agaaatgtgc tatgtctgtc atttcagcct | 5160 |
| tatgaattgc ccagaataag ctagatcacc tttaaggcca tgtggttagg gaaacttggg | 5220 |
| cacagaattt acattttcaa cttggtgata agatgggttt aaggtaagaa tcaaatagga | 5280 |
| gaaagcctta gctgttccag cggcccatgt ttaaaagaat gtgcttcttt ttccaagtat | 5340 |
| ttctgccgct tgcatgcact gagcttcttt ggaaggagc accatgcagg catattttcc | 5400 |
| agacaggacc ggatttgctc gttactcaga ggtgtgtgca ttctttgctt ttaggatatt | 5460 |
| taattagcat cttttaatag tgatattacg gtgtcttaaa agtttatgca tttgaaaaga | 5520 |
| aaagaactta ctccttgcca ggtctcaacc tatcatggtt atctttgcag ctgagctgcg | 5580 |
| ttggttttga ggctcacata tggtaaaagt ggttggaaat ctggaaatat gctgtgtat | 5640 |
| ctgcaaagca gcttgatata gtggaaaagg tattaggtca ttaatcatga gatttggatt | 5700 |
| ctagccccctt agctgctgcc tgccaggcct ggagaccttt gttctcttct ttaaactgct | 5760 |
| gctttctcat cagaaaatga agttcctctc cataccacct ctctgaaggg ctgtgaagct | 5820 |
| cgaagtggca gcttaaaaaa ctgcccatct caggaggtgt cttaagaagg aggacatacc | 5880 |
| gctggctcct gcctttctca cttagccagg tctgatacct gtgttgtttt cactgtggcc | 5940 |
| attttaggat ttttcaaagg ctttcagaaa gcaacatgct accgtacccc ttatacacca | 6000 |
| aaactggttt tcattttgga atataaaagt gagatttctc caccagtaca ataaagttgt | 6060 |

```
tacaagtggt tcctatgtgt ttgttttttgt ttttgagaca gagtctcact ctgtcaccca    6120
ggctgcagtg cagtggcaca atcttggctc actgcaacct ccgcctcccg ggttcaagca    6180
attctcccac ctcagcctcc taagtagctg ggactacagg cacccgccac cacgcccagc    6240
taatttttgt attttttagta gagatggagt ttcaccatgt tggccaggct ggttttgaac    6300
ttctgacctc aggtgatcca cctgcttcag cctcccaaag tcttaggatt acaggcgtga    6360
gccaccacac ccggcctcct gtgtgttttg aaggtgattg tgacctcagg ttttggcagg    6420
gctataccttt gtgtttgctc ttactccaac tccatggcat acctggacca ggcctcttca    6480
tcttgaagag ggatctgctg aaatgcaggc ccagtgaatc tccccatgcc tggacacagt    6540
tccgtcaagc caggacccgg tgctgcctgc acccctgttt ctgttagtct gactgtcctc    6600
gctgagtcta actccttgag ggcagagagg atgtcttatt tatttctgcc ccgctagccg    6660
tgtaaactga gtaggtactt gtaaatgttc attgaataag tacctgatta atagaattta    6720
attcaagaag aatgtattga tgggcctgtg tggtcaccac agtactgaga tgtaggtggg    6780
agctggctga agggggaggc acctaaacag gagtgcagac agcggcacct acggatgatg    6840
gcccgctcca tcccaccgca gcgaaattgt cccagacctc tgcagcttcc cccacaccta    6900
gactgagaga gagctcttct tccttctgta gggagcaggg gttttcctcca gatgtccaat    6960
atgtacctcc cattacagcg gtgttaggaa ggtgagggct gccgctgaaa gggtcccctt    7020
cataatcatc actagatttg gggtatatta tggattaaat agaatttta taagatgacc    7080
tgaggatcta tttaaataaa atcctctttc tttctgcaag atcatggatt taaattcaac    7140
acaactgact tcatagggaa ggggtatggt gaaaggaag tgaggtgggc agcactgata    7200
tttaacaagg tgagggtcct tctcctgctc tgactgtcac attaaaatat tcccaggaga    7260
aattggagaa aactcagatg aaatatcgtc tgtgttccag gaggcaggac tcatcggaat    7320
gcttttatt tgctccattt taagagattt gcagataaag aggagtgaag atttctattc    7380
agatttactt gctttatatt ttaacttata gaccacaagc caactttcga aagagcatca    7440
ttttgaatag taagagttag gaaggcaaat acagaaggac taatggcttc caagattatg    7500
agcttcatag gaatggtttg agatgaggct atagtaaagc agaatattga agttccccca    7560
ccccctttca ttttttcattt ttcatttttta agagtgagcg aggccaggcg tggaggctca    7620
cacctgtaat cccagcactt tgggaggccg aggtgggcag atcacaaggt caggagtttg    7680
agaccagcct ggccatcatg gtgaaaccct gtctctacta aatgtacaaa aattagccag    7740
gcttggtatc aggtgcctgt aatcccagct actcaggagg ctgaggcagg aaaattgctt    7800
gaacccagga gtcggaggtt gcagtgagct gagatcgcac cactgcacat ctcagaaaaa    7860
aaaagagtga ggccccaagt tttttttgcat ttgtttgtaa ctgaatacgt ctgaagttat    7920
gtgataacca cgccaaggtg acaaattgcc aagtttcagt aaaagagacc cagttattta    7980
gaggttgaca cgtggatatg tcccttttcta agaagttcgt ggtcagcttt acatgagtat    8040
ttaaatgcgt gtttataatt cagcaatatg gcttgtaaaa tacagattgc caatcaagtg    8100
acatgcaaat cttgatgatc tgaaacaagt tttcttctgt tatctatgga agaaatggta    8160
atagggatat ttaagtggga tgaattttt gaagcatttt caggcagttt ccacatggaa    8220
acaaaataac attgagtggg ctgctaacat gaggaacata ttgccctctg cctaggatta    8280
tgagtaaatt tgataaattc tagactgcag tctcattta gctcattta tgaggcagct    8340
tgacaactgg gatagtgtct cttttttttg tcggggtgt tgaggctgga gtctcgctct    8400
gctgcccagg ctggagtgca ctggcgtgat ctcggctcac tgcaacctct gcctccgggg    8460
```

```
ttccagtggt tctcctacct cagcctcctg agaagctggg attgtaggca tgtgccacca    8520
cgcccggcta attttttgtat ttttttagtgg agacgggctt tcaccatgtt ggccaggctg   8580
ggtctcaaac tcctgacctg aagtgatctg cccgcctcag ccaccctaag tactgggatt    8640
acaggcatga gccaccacac ctggcttctg ttctatctgt gcattgggga tgaaattaac    8700
acaaatgatg tttaaagaaa aaatgctca gagaagttag aaatgtgctt taaattggaa    8760
tcatctctta gtatgtaaaa gttttttgta atagaaacaa gcagggcagt atttgacctg   8820
ttgacagtgt ccttggactt tacaatttgt gaagcagcgt attttgcttg agttgtacga    8880
ttgtcgtttt ttcccccca ctttgacaac tgttacagaa cctgtcacca gatacaggca     8940
agggaggttg ggcttcccat ctctgcacgg cttccctgtg attcacaagc aagcaatcag   9000
aagtgcacaa agtttagaa cgcgattttc attctcttct ttccttagaa aaactcgctt    9060
tgttagcctt ttccagaaag gaaggcactc aattgttgta atactcaaat cataaaaga    9120
agcctagtct agtctattca gcaaggtgtt ctgaaagagg gaattttta agttcaatta    9180
tgcgaagatc ttgaaggtgg gactcaaagg agagggctat cctgggaaga aggctttgga    9240
aaatgagagg catgaagggg agagggtatt taaatgtgtt tgaagccaag gatccttgag    9300
agaaaaagct ggcactaaca gcgttcaaag aacttgcgtg acaagtgatg actaatgaca    9360
ctgagggtgg gttgtgggtg cctagtgaat tcctccgaag ccaagagaga ggtttccaga    9420
cccagggaag aaggtgtgta cacccagaag tagtgtaggg acagagattc cgatcacaag    9480
ctgtgactgg aagacgccga ccaccactgc agcagcctga aaaccacagt cttgaaccgc    9540
cagcgaaggg ctgggaagtg cggatccagg gctggtgcac tgaacccaga ggagcaggct    9600
cccattccca gctaagggtg gcagctggcg gggatctttc cagcagaaag ctgtaagtgg   9660
aagctttcaa ttcagagcag tagcaatgcc ttcaaagtcc caggcttcac gtgggaacag   9720
agaatgtgaa gagtatttag caggatgcca atataagaaa tctatattgg tgttcgtttg   9780
tttgttttg agatggagtc tcgctctgtc acccaggccg gagtgcagtg gtgcgatctc   9840
agctcactgc aatctctgcc tcctgggttc aagcgattct cctgcctcag cctcctacat    9900
agctggtact acaggcacgc gccaccatgc ctggctaaat tgttgtattt ttagtagaga    9960
tggggtttca ccacgttggc caggctggtc tcaaactccc ggcctcatga tccgccctct   10020
gcagcctccc aaagtgctgg gattacaggc gtgagccacc gcacctggcc caatattgtt    10080
tgtttattta tttcttgaca ggatctcact ctgtcaccag gctggagtgc agtggtgtga    10140
tctcagctca ctgcaacctc cacctctctg gctcaagcaa tcctccctcc tcagcctcct   10200
gagcagctgg gactacaggt gcacccacc acacccaact agattttgtg ttttttgtag   10260
agatggggtt tagccatgtt cagctagtct caaactcctg ggctcaagtg atctgtccgc    10320
cttggcctcc caagtgttg ggattacagg tgtgattcat gatgtccagc ccagtatttt     10380
tctttcactc tggaaaccaa aaattattgg ctttttttcc tgttgcattc cctttactta    10440
gatgaatcta gcaaggttgg ctgttagtgt ctaggtcaga agtctaagtg aaagtgaata    10500
tttaaccaca ctcaagcaca gctgatgatc tttaatacta atagaggtat aagacttaaa    10560
agaaacaaga acccagaggg aaaatatggc catggactca gagaaaacca cggcagcttc    10620
catggactca taaaaagagc tcaaaaccta ggaagtggat ggagactctt tttggaatga    10680
atgaattcaa atgtgggctt tcttagtaga ttaaatcatt ttctagaagg aatttcgaaa    10740
ggatgtgtgc ccaattatgg tatcaggtct gttgtagact cttcaaggag gaagcctctg    10800
```

```
aaagacaaga aggaacaatt aaaaattaga attcaggtga gtggatcacg aggtcaagag    10860
atcgagacca gcctggccaa catggtgaaa ccccgtctct actaaaaata caaaatttag    10920
ctgggcatgg tatggctgta gtcccagcta ctcgggaggc tgaggcagga gaatcacttg    10980
aacccgggag gcggaggctg cagtgaacca agattgtgcc actgcactcc agcctggcaa    11040
cagcgagact ccatctcaaa aataataagt aaataaataa ataaataaaa attagaactc    11100
agaaaaggaa ttaatttctt ctgagagaga aaaagatgag attctagcct aaggtgtaac    11160
acatccatcc accaggtatc attttttatac acgtgaagtt aaatcaccaa aggaccaggt    11220
gagcagatgt ggactttccg actgtgtgtg tgcgacttcc tcagagccct cagtggcgtt    11280
cccttttccg cgctagcgtt tggtccctgc gcttttctgg atgcccccac ccctctggc     11340 tccacgaggc cccctgtacg tcaccatcac ctttgtgagc ttgaaacctg tcacccaccc    11400
gccttccaga tgtcacctgg gccctcccgg aggccctcgc cctcagtgtg tctgattctg    11460
agctgtcctg cgttttcccc tcccctcacc ctggcgaccc ttttcggtct cagttgccag    11520
cctcctgcta gggctgggtg ggggacatca aaggcaggac aaggtgtagg gtcctcaccc    11580
accacttagc agctctcaga tgcagacaga ttttcagct ggcctgtggc tcagtttccc    11640
tcagctacaa gaggggtgca tgctagggtt tctctggatt gctgcacctg gcaggtagtg    11700
tgagcttggt aggtgcttcc ttgcttatca ttgcctctcc catcttaatg ttgtcccatc    11760
catccaatgt ttatgggatg agaggttgat aggagggcat ggccctgaca ttccagggac    11820
tgaccgacac gctgtctaca caaacccctt ctggttcttc tcgtgcactg ggcgtgccgg    11880
agacacactc ccttaccctc ataccccgcc gcacccctgt gacctctacc tttgagacct    11940
cagcttaaac tcactcttag ggaaggctcc ctgaaccacc tgctggggtt gtatgctgat    12000
gcaggtactt gtaacacctg gtgcttttcc tttcgtgcac tcaggcagtg tttattcaag    12060
tgatggcttg gtgacagtgg ctctccctga accccgtga ggccagagtc cttggctcat     12120
cactcatggt tgaacccgga gcctcttgct ggtaggtgct tcaggactgg ctctgggagc    12180
ctgtggctcc tgccgggtac ccaccggttg agatacctca agttttaaat gccacctcct    12240
tcctgaagcc ttccttgctg ctcccccaaa ctagaggcag gagttttgtc cttcagataa    12300
cctatggcat ttgagtcact ctgatttgat gaattctgcc ttcacttgag cagctattag    12360
gggcatatgt cagtcattca ttcctcagtt catgtattta ttcagcaaat atttactgag    12420
cacgtactgc gtgccaggca ctgtcctgct gtggaaaaca gcaggcatga ttccctgcca    12480
ctaccaacca ctgcatcgca taactggcag actcccagct tcaaggagag gcacggaggg    12540
aaactgagag cagcctgcag aggggaaaga gcggggacag agggtcacgg aggtcgcagg    12600
ggcgtgtgtg cagcacctgc cagtgaacgg aatgtgcggc tccagatgtc gttgtcttta    12660
aacttcggaa tttcctttca ctaaagaacc aagtccaggg ggaggaaaga gtgaatacaa    12720
attatccaag aaactcaaga gctcatttta gttctcctga ttatgatctt aaaggcatta    12780
agcgctcaag ttaaactcct tgtgacccac ataggttagc agaatttaaa tcctaggtga    12840
ttattaactc taatcataca tctaatgacc tatattgaag atacactgcc tgcttagttg    12900
tggcttcagc ctttgctccg tcactgatag ttctagcctg aaaagcaaat gagccctcat    12960
gctcacgatt tcaccacagt cacataagcg ggaagagcag gctcctggct gtggcgagct    13020
tgactccatt tggtttgata gaaatgagag gtagatgatt ccctagacaa atgcaggcct    13080
ttctcgaagc ccctttccca ggacgacgtg acatgagtgg tctgtgcctt ccagggcagc    13140
cacgtcatgc tttgcccagc cagggcggtg gggagggaga cagccacatc ctgcccgggg    13200
```

```
ctcctgggcc ccgctgcatc aagtgaaagc agggctggct ccctgatgtc cttggagaag      13260
tcgcccacac tgctttcccc catgggagtg acaaggatgt gtcccgccag ccttccacga      13320
cggacccccc actctctatt aattcccaag aaaccaggcc atggaggtgg gtttgagggt      13380
ttgtattggt gttttttaaa gtcaggttga ccgagtgcgg tggctcacgc ttgtaatccc      13440
agcactttgg gaggctgagg cgggcggatc acatgaggtc aggagttcaa gaccagcctg      13500
gccaacatgg tgaaaccttg tctctactaa aactacaaaa aaaattacct gggcgtggtg      13560
gtgggcgcct gtaatcccag ctactcagga ggctgaggca ggagaaaccc ttgaactagg      13620
gaggctgcag tgagccgaga tcgcgccact ccagcctggg tgacaagagt gagattctgc      13680
ctcaaaataa ataaagtcgg gtttattaag atataattta catacagtaa ttttttttttt     13740 ttttgagaca gagtttcact cttgttgccc aggctggagt gcaatggcac gatctcagct      13800
cactgcaacc tccgcttcca gggttcaagc cattctactg cctcagcctc ctgagtagct      13860
gagattacag gtgtccacca ccatgccttg ctaattttg tatttttagt agagacaggt       13920
tttcgctatg ttggccaagc tggtcttgaa ctcctgacct caggtgatcc gccagcctcg      13980
gcctcccaaa gtgctgggat tacaggcatg agccactgca cccggccagt acatgctttc      14040
ttgatttgtc tgtttcccac ctgtctcccc tccctagaat ggcagctcca tgacgacaga      14100
ggtgtttctc tgttttctcc atggctgcac cctcagctgc tagaaggtgg cccagcatag      14160
gaggtattta atgaagcctt cctctccact taaatctaca cccttgtgct tattaaaagg      14220
tgacagtttt ctgtttgaaa attttattag tgttttaatg agaaagttat tatttgggta      14280
atgcctgaat atgaggaaaa cattaagggt agaaatgtaa ttgttttcct atttcattca      14340
gtctatggat tttattgaag attacagaat tacttctttg tagctatgga agtaaaaaaa      14400
taataagacg agtagctatt tcaaaacgta gggctgataa atttgggatg gtttgagaac      14460
gttaagttgg ggaactccat ттcтттттттт acatttttat ттатттттcat tgttttatt      14520

atttatttga acagagttt cgctctgttg cccaggctag agtgcaatgc catgatctcg       14580
gctcactgca acctctgcct ccggggtata agtgattctc ccatatcagc ctcccgagga      14640
gctgggacta caggcgcctg ccaccacacc tggctaattt ттgтaтттттт agtagagatg    14700 ggatttggcc atgtcagcca ggctggcctc aaactcctga ccgcaggtga tccgcctgcc      14760
cttggcctcc caagtgctgg gattacagg tgtgagccac cgcgcccagc cagggaactg      14820 cattctgac agtggctcag tagттттggaa gttaactggc aaaggtggac agaatcttta      14880
aacatatgtg gaggaattgg agagtttaca agaтагтgaa gaactgccag gccatggtct      14940
ggagaagatg gaaacttgat gtttgggcc attgtgtccc tggggtgttg gccaatttat      15000
gaaagaagca gttaagagcc тgaгтggcac ttttgagggg ctagaaggga agaccctggt      15060
aaacatccca aactttggat tgggacccaa aaaagctcca tcccaggagt acaggtgacc      15120

tggaaacgga tcagcgtaat cgaggactga agtccagttc tagctacgcc cagtccttga      15180
gactggatta aggtgatctc agattgcaag gacctcaaat gcctggcaga agcaagtgaa      15240

tatccttctg gaggaacaga gcctcatcct aggcctctaa ттаттттттаа ggacaattt     15300

tcaaatgcag gcttt cctcc ctttgcacag ttcccttatg cataaatttc agtcagtggc      15360
cagctgcagt ggctcatgca tgtaatccca gcgctttggg aggccaaggc gggtgaattg      15420
cttgagtctg ggagttggag accggcctgg gcaacataga ccccatctc tatttttaaa      15480

aataaaatat taatTATcac tgcttagtta aatTATagtg gtctcccaac aatacagatc      15540
```

```
agatcccagc tcccatggta tatacactgt gagtgctgta taaagtacaa gctctgccgc    15600
cagttctcca gcctacaaat cacagtatag ataacagatg tgcatgatga tcactggcca    15660
attgcgtcac ttctctcaaa gtcagtctgt gattggtccc tgagcatctg tcggtcagtt    15720
tcatgcacag actgcaaagc atatggtttt gtctactctt tgtctctcag tgataaaccc    15780
acatggcatt ttgtaaaagt ggatacatca ggccaggtgt ggtggctcat gcctgtaatc    15840
ccagcacttt gggaggctga ggcaggtgga tcatttgggg tcaggagttt gagaccagcc    15900
tggccaacat ggtgaaaccc catctctact aaaaatacaa aaattagctg gatgtggtgg    15960
caggcgcctg taatcccagt tactggggag gctgaggcag gagaattgct tgaacccagg    16020
aggcagagct tgcagtgagc cgagatcatg ccactgcact ctagcctggg tgacagagca    16080
agactaccat ctcaaaaaaa aaaaaacaaa aacagtaat caagcatgaa aattatgaaa     16140
tgctcagaga taaatgcgc gaggcctgta cactgtaatc tacaaaacac tgctgagaga     16200
aattttaaaa gacctaaata aatggcaagt tataacatgc tcttgaatca gaagactcag    16260
tatcttagga tggcgacttt tcccaaaatg atctacagat tcaaagcaat cggaatcaga    16320
cctcagcatg cctacttgta gaatttgata acctgattct aaagtttata tggaaatgca    16380
aggaacccag agttgctaaa ataactttga aaagaacaa cacagttgaa ggacttagac     16440
tacatgattt caagaattat tataaagcta cagtaatcaa gacagtatgg tattgatatg    16500
aaaatagacc attagatgaa tggaacagaa tagcaagtcc agaaatagat ccacacatat    16560
atggtcaatt gattttcagc aaagtgccaa gtcatttaag tggggaaaag ataatctttt    16620
caacaaatga taccggaaca actggatagc catatgcaaa agaacctcaa ccttcagctc    16680
acagcactac aaactcataa ttattatcat tatattatac tattatgtaa taatagtata    16740
tatcatgtta catattatat tatgtaatat atattatatg atactgttat gtcatatat     16800 tattattgaa atgggtcata gatctaattg taagagttaa aaccatccag gtacagtggc    16860
tcatgcctgt catcttgcac tttgagaggc caaggcgggt ggatcacttg ccccaggag     16920 ttacaagacc atcctgggca acatagcgaa acaccgtctc tacaaaaaaa tgaaaaaatt    16980
agttgagcat gatgacactc acctgtagtc ccagctgcac agtagtctga ggtggagga     17040 tcacctgagc ccagagaggt caaggttgca gtgagccatg attgcaccac tgcactccag    17100
actgggtgac agagagaccg tgtgttaaaa aaagagttaa aactataaaa ccttcagaag    17160
aaaacatatg agaaaattct agtgatttgg ggtttggcaa agattccttg aacatgatt     17220 aaaaagcatt aactaggcca ggtatgctgg cttacacctg tcattccaat gctttggggg    17280
accgaggtga gaggatagct tgaggccagg agtccgagag cagcctgggc aacataacaa    17340
gagtgggtct ttaccaaaaa aaaaaataa aaagcctgtg ccaggcacag tggcacatgt    17400
ctgtagtcct agctactcac gaagctgagg caggaggatc acttgagccc aggagttgaa    17460
gcttgcagtg aattatgacc atgccactgc actccagcct gggccacaga gtaagactaa    17520
gactcagtct cttaaagaag aaagcgaccg ggcgcagtgg ctcacgcctg taatcccagc    17580
actttgggag gctgaagcag gtggatcaca aggcaggag atgaagacca tcctggctaa    17640
cacggtgaaa ccccatctct actaaaaata caaaaatta gccggacgtg gtggtaggcg     17700
cctgtagtcc tagctactcg ggaggctgag gcaggagaat ggcgtgaacc tgggaggcgg    17760
agcttgcagt gagccaagat cgtaccactg cactccagcc tggacaacag agcgagactc    17820
catctcaaaa aaaaaaaaa aaaaaaaaa aagaagaaa gcataaacta taaagaaaa        17880 aattaataaa ttagtcatcc tcaaaattag aaactttac tcatcagaaa acacttaata     17940
```

```
aaatgaaaag tcaagccata gacttagaga aaatatttac aaaacatata tctgacaaag    18000
gacttggata tggattatat aaagaactat tgtaattcaa taagatgtca aacaacccaa    18060
ttaaaaatgg gtgaaagatg aactaactct tcaacaatgg gcatgtcatt tgaatggatg    18120
gtaagcaagc acatgaaaag atgttcatgt gcctttccct cattagtcac tagggaaatg    18180
caagttcata gacatctctc ttcgtagaaa gatatcacta cacacccaca agagtggctg    18240
taattaagca gtctgaccaa gtatgcgtaa gaatgtggaa taagaactct catacactgc    18300
tgatgggaat gtaaaatgat agccactttg gaaaacattt tggcaaataa taccacttac    18360
attattatcg aaaatattgt ataccctgaaa gaactcaaag tgaaaaagct atatactgtc    18420
tgcttccaag gctacacatt atgggaaagg caaaactatg aagacagtaa aaagatgcgc    18480
cagtggttgc caggggctca tggggaggga aagaggaatg aataggtgga acacagggca    18540
tgtttagggc agtgaaacta ttctgtatgg taccgtaacg atgaatacat gttattaggc    18600
atttgtcaat acccataaaa tgtacaacac aaagagtgaa aatgaaaact gtgggcttca    18660
gttagcaata atatgtcaac attggctcat cagtggcaac aaatgtacct caccaatgca    18720
agatgtttgt tgttgtttg tttgttttgt gacggagggg gtgcagtggc gcaatctcgg    18780
ctcactgcaa gctccgcctc ccgggttcac gccaatctcc tgcttcagcc tccggagtag    18840
ctgggactac aggcgcccgc caccacgccc ggctaatttt ttgtattttt agtagagacg    18900
gggtttcacc atgctagcca ggatggtctt gatctcctgc tgtcgtgatc tgcccgcctc    18960
ggcctcccaa agtgctggga ttacaggcat gagccatcac gcccggccac caatgcaaga    19020
tgttaataac agggaaactg tggtgggagt gaggtggtat atgagacctc tctgtacttt    19080
ccactcaatt tttctgtaag cccaaaactt ctctaaataa gaaagtttat taattaaaag    19140
ttacttttat agtgtatcta tatctaggaa taaatctgaa aaagatatat aagatctcta    19200
ctcagaaaac tgattatgtt attaagagag cttaaatata gcccaaataa atagatggat    19260
atactatgtt catggaaggg acagctcagt attaggaagg tgtcagtcat cttaagaaaa    19320
gcctcatgtg tcacacaagg gatactgaca tctgacacca agcacatgta ggcatcctga    19380
ctacgtttac ttgaatgatg tggacttac agagctgact atagacagtt caaatggcct    19440
gaaaactgtt caatgcactc cctcccaggc tgtcatggga tgcacttcag gaactttact    19500
ttttaacaag aaaattcagt tttcctctta aacagctggc ttctgttcca ttagcattct    19560
tgtcacttta agttgcattc atctttgttt tttttttta gaaaacatt tgttctgcaa    19620 ccagtcttgt cctttaaata cttgtactgt atacaggctc ttttcatag gtccattact    19680 taaaatgatg taagtgtgtt tttggtggca gggggtggg agttgtttgt tttgttttgt    19740
tgagacacgg tcttactctg tcacccaggc tggagtgcag tggtgtgatc ttggctcact    19800
cctggcctca gtgatccac ccacctcagc ctcctaagta gctgggacca caggtgtgta    19860
ccaccacacc cagctaattt ttttttttt tttttttt ttttgtaggg acggggtttt    19920
gtcatatcac ccaggctggt ctcaaactcc tggactcaag ggatcagcct gtctcagcct    19980
cccaaagtgc tgggattaca ggtgtgagcc actgcaccgg tcctgatttg agttttttgta    20040 agacagggaa caatgttcag aatttagcac caatgtcaga ctcattctgt aaatttttat    20100
tgaacgtctg cctggtgtag gagaggaaga tgacagacaa gaattcttcc tccaagagtt    20160
acaggtcagt tgagcagaaa aggcatacat caataccccac aatgagagtt gtcgtgattc    20220
agaggaggga caaagtcctt cccctggagg gatcctgagc actttggaga ggaaaggcat    20280
```

```
ctgtactgcc ccccaaatgt gtagaatggg atgcattcct ggcagaaaga agtaggataa    20340
agtacagagg ccagggctgg gtgcagtggt tcacgcctgt aatcccagca ctttgggagg    20400
ccgagacagc agatcacctg aggtcaggag ttcgagacca gcctggtcaa catggcaaaa    20460
ccctctctct actaaaaata caaaaattag ccaggcacaa tggcaggtac ctgtaatccc    20520
agctacttgg gaggctgagg caggagaatt gcttgagccc aggaggcaga gatcgcagtg    20580
agccaagact gcgccactgc actccagcct gggcaacaga gcaagactct gtctcataaa    20640 aaagaaaaa  aaaaaagtac agagtccagg aagcctgggg tggggctggc agatgccgag    20700
tcatctattt tggccagagt tcaaggcttg ctaggggaca tgaagagaag attcgtgcat    20760
tctagttcaa actccaccag atatttgagc tccttctctg taccaggcat tgttctaaga    20820
tacgtaagtg aacaaaaccc atgacaccct cgtctatgag agctgatcct ctggcaggga    20880
cagacaggtc atgagtggag tgatggagca gctggcctgg tgacttagcc gccttcaggt    20940
acagtaggag gagcaagccc aggacaggtg agtgggtcaa gggtgccaga aggggtgagg    21000
gcaccaggaa gctggtccag tttggcttcc ctgaggtggt gaccaggacc tagcatctga    21060
ggaagggctg gaagcaggtg agagcaggtg gagcagacat caggatggga gcatcctgac    21120 agggaggggca gcagggtggg ctcatgagag gaacagccag gaagtgtgac tcgagcagtg    21180
tcctggagag gaggaggagg agaaagaggt caggaggtcc caggggagag gcaggaccag    21240
tctcgtggag gtcggggccg ttgtgaggac tctggtttgt gttgtgtgtg aaaggccatg    21300
ggatggggac cagcgagggc ttcttagggg actggatatg ctctgatcta gctgctaaaa    21360 agccccccttg ggcagcttgc agggcccggg cagaagctat aggtggttct gaggtttgca    21420
gaggggcctg aaggggtggg gcccggccaa gcaaggtggc taagtgggaa aggctccacc    21480
gcgttgggtg taggaagacc ttgaccttag ctccagccca gccactgagc agccgtgtcg    21540
ccttgggtga tacctgtccc tggtcggttt ccctacctgt gaatctgggt acttggaagc    21600
catgctcgag aagagcccat ccccaggagg tgatcaggggt tctccttcag gtgaggaacc    21660
tggcagccgt gtgtgagaac cttagaaaag ggagagggaa gaggctgtgg caggaagtga    21720
ggagggagtt agtgataccc tgggcaggat gccatgagct gggatggaaa ccacaggatg    21780
aatgcaagta attaaaaaaa aaaaaaaaa  aaaaacagca ttgggccggg cagtggctca    21840
cgcctgtaat cccagcattt tgggaggccg aggtaggtgg atcacctgaa gtcaggagtt    21900
ggagaccagc ctagccaaca tggtgaaact gaaaatgcaa aaattagcca ggcatggtgg    21960
cgtgtgacta tagttccagc tactcaggag gctgagacag gagaatcact tgaacctggg    22020
aggtggatgt tgctgtgagc tgagatcgtg ccactgcatt gcagcctcgg tgagagagca    22080
aggccccatc tcaaaaaaga aaaaacaga ctttccgacc aaacgatcga caaaccagac    22140
tgtccaaaca gccataagcc gtaactttgt gcggaggtaa aagaccgagg tcacatcggg    22200
acctgttgga ttcaaggcat gttgacagct gtttccaggc ttcagataga gcctccagct    22260
ggcagggtgg ccacagggct tgttgagtag gaagcctcgt tgctttgaca ggttacttgg    22320
ccccatgagg gacaatccca tagtcagtta cccagaaacg tgactgtctc cttgaaatcc    22380
tcagcatggg gtcttatgaa taaacccttta ctagatttcc tgttctgtct tattttatg    22440 cagagcttta ctttatagca gaaaattcca ttttttaccct taaatggctt gcttctgctc    22500
ccttagtgtt cttgtcactt taagttgcat tcatctttgt ccctttagaa aaggatttgt    22560
cctgcaacca gctcttgcag aaggtacttg gtttattgtt aaccgatgtt tgctaaatgt    22620
ttgaattatg ttgagttgct taaagtcatg ctatcgggta gatgttgtgg ctgttctttt    22680
```

```
cactctctta tttggggatt tacaaaacag ttatgttttt agttttcttt tatttgttgt   22740
gttgaatagg aatgtagctc tgggaacctc tagttccaaa taagaaagcc ttggacacat   22800
ttccagttgg caagctggca aaatgaaggg cgtacaagtt gttagagagg ctgggagcct   22860
atttaagcac ccagcttcag gatgggacat gggatatacc tcgagttaga ggttcttatt   22920
aactgtggat tcttctatgc agatatctgt cacaatataa gttactataa gtcagtacta   22980
aggcagctgc tacattctgt ttgccaaggg gaagaagaaa gcttggaaat ggtattcctt   23040
aaaaatgtca gtatcataaa agacaaagaa aagctgcgga aatgtttcag attaaaagag   23100
agaagacaat aaaatgtaat acctgactct gaacagcatc cagtactgaa ggaggaaaaa   23160
tgctatcaag gacattattg ggtcaattaa caaaatttga atacgaatca tagattgaac   23220
tgtatctgtt aaattaacag aagcgaagtg ttctgtggtg tgtaggagca cactgccatt   23280
cttagcaaac gtgtagttta gtatttagga gaaagggcca tgaggcatgc aactcaccct   23340
caaatacaca cacacataca catatataca tacataccta taaagaaaga aattatgggc   23400
taggtgcagt ggctcatgcc tgtaatccca gcactttggg aggccgaggt gggtggattg   23460
tgaggtcagg agatcgagac cctctctact aaaatacaaa gaattagctg gcgtggtgg    23520 tgcacgtctg tagtcccagc tactcgggag gctgaggcag gagaattgct tgaacccagg   23580
aggcagaggt tacagtgagc cgagattgca ccactgcact gcagcctggc aacagagcaa   23640
gactctgtct tgaaagaagg aagaaagaga gagagagaga gagagagaga gagggagaaa   23700
gaaagagaga gagaaagaaa gaaagaagga aggaaggaag gaaggaagga aattatgata   23760
aagcagatgg ttaagttggt aactaccagt gaatatgggt aaagttagga tgttctttac   23820
tctgttttgg gggtgcaact tttctataag tgaaagtact tccaaataaa aagttaaaag   23880
gcaagcaaat aaataaaaga gacagtttct atgttatata tcctagctat gtttaccatg   23940
tctggattct gaaagctgca gagcagaaaa cctgaagaac agatcacctg ttcttaaaat   24000
accactgttg gccagacata gtaactcact cctgtaatcc cagcactttg ggaagccgag   24060
gtgggaggat cacctgagct caggagtttg agaacagcct gggaaacata gtgagaccct   24120
gtctctacaa aaatttaaaa aattatccag gcatcatggt tcgtgcctgt agtcctagct   24180
actcaggagg ctgaggtagg aggattgctt gagcctggga gttcgaggct gcagtgaacc   24240
atgatcacac taaagcactc tagcctgggc aacagagcaa gaccctgtat caaaaaaaca   24300
atcaaacaaa aaatcactcc taattttcct cccttttagt acttttaaaa attaacttaa   24360 aacattttt ggataattgt agttttttt acttttttt ttttgagaca gagtctcatt     24420
ctgtcaccca ggctggagtg tactggtgca atctcaggtg actgcaacct ctgtctcctg   24480
gattcaagtg attctcctgc ctcagcctcc tgagtagctg ggttcatagg cgtgcaccac   24540
acctggctcg ttttatatt tttagtagag atggggtttc accttgttgg ccaggctggt   24600
ctcagattcc tgacttcaag tgatctgccc gccttggcct cacgtgcagt tttaggaaat   24660
aatacagaga tcccccagcac tctttccagt tttccccaag ggtaacatct tgcaaagtga   24720
gaggacgata tcacagtcag gatactgaca ttgataccat caagatacat aatgtttcca   24780
tcaccaatca gtggtcatgg tgccttttat agccaaaccc acttctctcc taccttccca   24840
tccctttttt aattttgcca gtcattaatc tgttgcccat ttctgtcatt ttatgaatgt   24900
cacataggcc gggcgcggtg gctcacgcct gtaatcccag cactttggga ggccgaggca   24960
ggcggatcac gaggtcagga gatcgagacc atcctggcta acatggtgaa accccatctc   25020
```

```
tactaaaaaa tacaaaaaat tagccaagcg tggtggcggg cgcctgtagt cccagctact   25080
cgggaggctg aggcaggaga atggtgtgga cccgggagac ggagcttgta gtgagctgaa   25140
atcacaccac tgcactccag actgggtgac aaagcgagac tccatcttaa aaaaaaaaaa   25200
aaaagaatgt cacataatga atcatatggc atataaccgt ttgagactca gggtaattct   25260
catgagactc atccagcttg ttggtgcatc aacagtttat tcctttttat tgctgagtaa   25320
tttccatggt atggaggaac catgGtttaa ctattcaccc attggaggac atctaggttg   25380
tttccagctt ggagttatta tgaataaagc tgctgtgaac atttgtgtac aggtttcttg   25440
gttttctggt ttgttttaaa cagttctagc caggcacggt ggctcacacc tgtaatccta   25500
acacttggaa ggctgaggta ggaggactgc ttgatcctag gaggcagagg ttgcaaggag   25560
ccgaaattgt gccactgtac tccagcctgg gcaacatagc aagaccctgt cattcatagg   25620
taggtggatg gatggatgga cggacggaca gatagatagg tagaaatgta aattacaggg   25680
ctacgctcag tggctcatgc ctgtaatctc agcactttgg gaggcgaagg cgggcggatc   25740
accagaggtc agcagtttga gaccagcctg gccaacatgg caaaacccca tctctactaa   25800
aaatacaaaa attagccaag catgctggca tgtgcctgca atcccagcta ctttggaggc   25860
tgaggcagga gaatcacttg aacccaggag gcggaggtta caatgagcca agatcatgcc   25920
actgcactcc agcctgggcc acagagtgag actccgtatc agtactttct ttttattgtt   25980
tttctgttat tatagtttaa gttcattgtt attagattat atactctgta tggcttcaat   26040
tcttttaaat ttgttgaggt ttgtttaatg gtcaaagaca tggtctgtct aggtgaatgt   26100
tccatgggct tttagggaaa aaagtatatt ctagtgttgt tgaatggtgt cttagtccat   26160
tcaagctgct ataacaaaat accgtaaact gggtgattta taaacaacag aaatttttct   26220
ctcacagttc tggaggctgg gaagttcaag atcaaagtgc cagcagattc agtgtcatgt   26280
gaggacgtgc ttcctgcttc atagataaga ggtacataca cgtttaggag catcgtgtct   26340
tcctggtgga tgaattctgt tatcattagg tgatcctttg agcacttttg aaaagaatct   26400
gttggccggg cgcagtggct cacgcctgta atcccaggac tttgggggc caaggcgggc   26460 agatcacgag gttaggagat tgagaccatc ctggctaaca cagtgaaacc ctgtctctac   26520
tacaaataca aaaaattag ccgggcatgg tggcaggcgc ctgtagtccc agctactcag   26580
gaggctgagg caggagaatg gcgtgaacac aggaggcaga gcttgcagtg agccaagatc   26640
acgccactgc actccagcct gggcaacaaa gtgagaccct gtctcaaaaa ataaaataaa   26700
ataaaataaa aataatctgt ttaatagcct actagtgttc ttcctttact attttattga   26760
gcattaatta atcccaacat tatgtctatg tcaggactga tgacaatatt tggtatataaa   26820 atttgatagt ctcagaggct gaggcaggag aatgcttgaa tccaggaggc agaggttgca   26880
gtgagctgag accgtgccac tgcactccag cctgggcaac agaacaagac tccatctcaa   26940
aaaaaaaaaa aaaaaaatcg atagtatcat atcctccagg attcaaagtg aacttcaaac   27000
agtcttatgt agtctaaatt ttggaatgca tcccagtatt gagttgcagc agggatttga   27060 gttttttgtga agagagagag gtatatcaga atcttgggca taaactaagg agccatgtca   27120
gaacctcagg tgtatgccaa tgagatagat cagaacctca gcatgtacc cgatgagaca   27180 gatcagaacc tcaggcgtgt acccggtgag acaggtcaga acctcaagcg tgtacctgtt   27240
gagacaggtc agaacctcag gcgtgtagcc agtgagacag gtcagaacct caggtgtgta   27300
cccagtgaga cagatgagaa cctcaggtgt gtaaccagtg atatatatca gaatcttggg   27360
tatttaccca agaggtata gcagagtctc aggtatatac tcaagaaggc atatcttgag   27420
```

```
gctttaagta tctagctaag gatttatatc aggatctcag gtttatacccc agggaggtat    27480 agcagaattt ggggtataga tctaaggagg tctatcagtc tagagcatat agccaaggaa    27540
ctatatcaga acctcaggca cctacccaaa gaggcatttt aggactcgta aggaggggt     27600 agatttcaaa agtgtagtct aacagtttat ctactttgaa atttaaaaca atattaaagg    27660
aaaacatgaa atatttctat ctgtcagaag gtgacatgag tttttaaacaa ttaagaaata   27720 tactggctgt ggccttgtaa ccaaattatt atgcctatag aaattacaga ctccattttc    27780
caggatagaa taacagggac tgacttacct tctcatctga gataacaaaa cctccataca   27840
aatacatgaa acaatgttct tcaagatgct ggacatcagg cagtgaaggg cactgatggt    27900
tgtaagacaa ggtgagaggt gtggcttgag agagtttcca ggttgcagtg cagggagagg    27960
ggaaactgag gcagatcttg gcagacttcc tcagttgaca aaatagagct gagagtccag    28020
ggagaccatg gtgtatagat tatccaaagc aaagtatgag aggtgcaagc catatacaga    28080
gggactccag agatctacca aagtacttct tggtgcatcc atatgagcaa aactacttga    28140
ggccaggaaa agaaccatct gagaggatta aaggaacag tgcccagtac ttgtgccagc    28200
caggaatggt gcctgatact cacgcagggc caggaacagt gcaggatgt gagtgtttgt     28260 taggagaggg aggtatatca gaatcttggg cataaagaca agaaaccata tcagaacatc    28320
aggtgtgtac caatgagata gatcagaatc tcggtgtat acacagtgag atagatcaga     28380
atctcagatg tgtacacagt gaagcagatc agaatctcag atgtatacac agtgagatag    28440
attggaatct caggtatgta cccagtgagt ccaagagcat ggtgctggca tccggtgagg    28500
gccttcctgc tggatcgtga catgaagcaa ggcaaagagc ctgtcagctc agggctctct    28560
tcctcttctt ataaagtcac cagtcctatc atggggggccc caccctgatg atcttataat   28620
cctaattacc tcccaaaggc taccttcaaa tgctatcaac atatgaattt ggaaactaag    28680
tttccagcac atgaaatttg ggggatacat tcaaagtata gcaaatatta catcataacc     28740
agtaggattc atcccaggaa atgccaaatg gcttgataat caaaaattaa tgtaactcat    28800
cgtattaaca ggatgaaaaa gaaaaaccat gtgatcatct tagtagatgc agaaaagcag    28860
ttgattaaat cccacattca tttctaactt aaaaaaacaa ctggatttg acagaggtgc     28920 aaaggcaatt tggtagagaa aggacagtct tttcaataaa tggtgctggt gcaatggtta    28980
tccatatgcc caaaatgaac tttgacccat gcctcatgcc atacacaaaa attaactcaa    29040
aatagatcag agatctgaag gtaaaattta aaactataaa acttctagaa gaaaacacag    29100
gagaaaaatc tttgtgacct tggtctaggc aaagatttca tagatatgac accgagaaca    29160
caatctatga aagaaaaaaa tcaataaatt gaacttcatc aaaatgaaac ttttactgtt    29220
caaaagacag ttttaggaga atgaaaacac aagttacaca ttgggaagaa atattcgaaa    29280
agcatttgcc tgataaaggt attgtagctg gaagacagaa aaaattctca aaactcacct    29340
agaagaaaat aacccagttt taaaaatggg caagagatct gaacaaacac attgtcaaag    29400
aagatagatg aatagcaagt aagcatgtga aaaattctca atgttatcag tcatcagagc    29460
aatgcagatg aaacctacag tccccatgct aatgttctac aacttacaca gtggtggtat    29520
gataccacta catgcccatt tgaatggcca aaattagaaa ggttgaccat accaaacatt    29580
agccatgatg tgcaggaact agaactctca tctttgctga caggaaggta aaatgataca    29640
aacacattga aaaacaggtt ggcagttgct ttttttttt tttgagatgg agtcttgctc     29700
tcccaggctg gagtacagtg gcgcgatctc agctcactgc aacctctgcc tcccaatgaa    29760
```

```
ttagaaaaat aataataaag gtaacaatag cagtaataat aatagaaata atgatagttt    29820
ctttaataaa aatgctgttt aggcccagac tgaaaggctt taagtaacca ctcccccact    29880
gaagttagag ttaagaaaga atattaattt tccttgtgtg aaacattaat cttatctagc    29940
ctccatgtat tttgtaagtt ctgtaaattc ctgttttccc tgcacagctg caagttcaca    30000
aggcagataa gcttaagctg caaaacatgt ttttcttaag atgtaaggca tgtcacaaga    30060
atatcacaag atgataacgg cctttattct cacttctgta tgcctgcttc ctgcctcaca    30120
tatttcctgc ctcaagatgc gtaaaggta cttgccttct ttgtttggtg ctctgacttt     30180
ctggatgcaa gtccactgag ccagtgtaca ccttaaataa atcctcctga accccatcaa    30240
tcgctccagt tctctgattt cccactacat tttctggggg ctcgtccggg attggagatg    30300
gcagattttc tgtctccctt gcctgtggaa ctggagcccg ggtcgaggga gacctgggac    30360 cttggtgcc aatgggagga ctttagcccg gaaaggagat tggctctcct gcatcccggt     30420
gtccttccta gacagcacaa cggaacctat aaagggttg caggacggtt ccagcagggg     30480
ctggggatgg tgagagtagc tcactgattc agatgacagg gttttgccat gttgcccaga    30540
cccagagggg ctgggacag tgagagtagc tcactgattc agatgaaact tacaccttag     30600
ccgatgcagg acacgagagt ggctcactaa gttggtcagg aaagaaactg aaaatgggaa    30660
gagtggcttc ctgccttgac taaggatcgg gaactgggag cggggaggtg tgtgaaagag    30720
atggttccgg gagggccgtg atgtggggag acacagatct cttagcacgg actgtgtgct    30780
ctgaggcgag tgtgtgattg accagaacca gggcatcaca tacagctgac aggagctgcc    30840
ccacagctgc agcaggctgt ggcaggaata aggtactctc ctagctaagc agcacctgaa    30900
acttccgtaa taggacccag tctggtcagt ctggaacgaa agtgagagtg agtgtgcatc    30960
acaaagggcg ggatgggagg aaaagcatcg aaacccactc ctctggggtg catgttaaag    31020
aattttaaga aaggttttgc tggagattat ggaattaagt tgtccccccc aaagattgag    31080
ggttctgtgt gaagtggaat ggccttcttt taatgtcggg tggccagccg agggtacaat    31140 aaataggaa atgattggtc atatatttag ggtagtgact ggggttggag gacaccctgg    31200
gcatccagat cagttcccat acatcaattc ctggatgatc acagtctaga catgccccaa    31260
atggttacag ccttgtctgg caacttactg taagactcta gtgacctgag ccgaacctaa    31320
ggcagttaga gggcccccctt caccagacac ctcaggtgga aagaaaaagc cacaggaaaa    31380
ttaggaaaga cctgttctac ttcactggga tcaagtgatt ctcctgcctc agcctcctga    31440
gtagctggga gtacgggtgt gcaccaccac gcctggctaa ttttttttaaa ttttattttt     31500 agtagagacg gggttttgcc acattggcca ggctggtctt gaactcctga cctcagacag    31560
tctgcctgcc ttggcctccc aaagtgctgg gattacaggt gtgaaccacc atgcccagcc    31620
agcagtttct tataaagtta aaccaatgcc taccatgaga tctggcaatc ccactcctaa    31680
gtatttggcc aagaaaaaag aaagcatata ttccatacag agtctagtcc tgaatgtcta    31740
tagctgcttt atttataata gctcagactt ggaaaccatt cagatgccat taataggtga    31800
atatattctc aaactgtggt tatccataca atggagtatt actttgcaat caaaaggaat    31860
ggcctatgaa tacccataac aacatggatg aatgctgaaa taattgtgct gagtaaaaga    31920
agacaggaaa aataagtata atacatactg cttgattcta tttgtataaa actagaaagt    31980
acaaactaat ctgtaatgac aggaagcaga ccagtgacag tgggcatgga ggggcaagag    32040
ggagagatta gatgggcaca ggagagcttt gaggatgatg ggtctgcgta ctgtctcggc    32100
tatgatagtg gtttcacagg ttgatacata cggcaaaaaa taccaaattt gtacacttta    32160
```

```
aatatgtaca gattattgta tgccagttac atgtccataa agctttcttt tgttgttttg   32220 ttttttatttt attttttgag acagagtctc gctccatcgt ccaggctgga gtgcaatggc   32280
accgtctcag agcactgtaa cctccgcctc ccggggttcaa gcgattctca tgcctcagcc   32340
tcccaagtag ctgagactac aggcatacgc caccatgccc agctaatttt tctattttta   32400
gtaaagacag ggtttcgcca tgattgccag gctggtcttg aactcctgac ctcaggtgat   32460
ccacccacct cggcctccca aagtgttggg attataggca tgagccacag caccgggccc   32520
ataaagctgt cttttaaatg aaaaaaagtt gtcttgaaat aagcattaga actgtggctt   32580
tggctctgaa atcctcatct gaggacccac actcgggtgc cccaatgtgg cggtgcttac   32640
agaaatgact ccatctgcta aatgagtaaa tgggtaattc tccactgaac acacactcgt   32700
ttagcagcat aagcagcaag agttcaggta atcctcacat tgcaatttgt cattagttta   32760
aacttccagt ctttgtttta aaacacatt agaataatac tacattttcc ctcatctcta   32820
aacttgactg aagactccaa gagagagtaa tattcatcaa gaggatcatc tactcaacac   32880
agataaactg ggaaagaaaa ataacttgtg agtaattcag aatctggatt atcaggtcag   32940
gctcaatggc tcacgccagt agtcccagca ctttgcgggg cccaggaggg cagatcactt   33000
gagttcagga gtttgagacc agcctgggca acatggcgaa accctgtcta tacaaaaaat   33060
agaaaaatta gccaggcatg gtggcatgtg cctgtagtcc cagttacccg ggaggctgag   33120
gtgggaggat cacttgagcc tgggaggtcg atattgcagt gagctgtaat tgcaccatgc   33180
actccagcct gggtgaaaga aggaaactct gtgtccaaaa caaaacaaaa caaaacaaaa   33240
aaagctaaat tatcaaatgt ctagatcgtt gatggttgga agtaaagttg agaaatgttc   33300
acactgggag atgacacaca gtaaaccaca cagagggttc taacgtggtt gttagaagca   33360
gaaactagag gcttgctgcc tgaggtcaaa ccccggtccc ggtggttctg tgccccagcg   33420
catgttgtgg tagcctctct gtacttcagt ttcctcatct gtaaagtaaa cataatgata   33480
atgcctgcct catggggttg ctgttaccag gaagtgagtt aatgcacatt aggttcttat   33540
ttatgacagt gcctggcata ggataagggc tcaaaaagtg ttagctggaa ctactatcat   33600
tatcaacatc tctaatttat tgcagggttg gatctgaaaa atggctgatg atgatttgat   33660
gatgacttca tttttataaa acaataatat tgcagtgcaa attaaacaca agcaacctgc   33720
aacacgccac tgcaagttgg atgtctagaa aaggtgccat gagttacctt ctaaaacatc   33780
ataagaaacc atgttcacca ataattacca taataggaga gaagtaccaa gtaccatggg   33840
gagacagagt ccagaatctc agagagagac acagttacct tttagttaca ctaatgggga   33900
aaacaggagc tttgctaccc ttgcacctga tggagggctt ctctgaatat agggctatgg   33960
ggtcagaagc cagtttcctc ccatatttag aaggtttcca actgttatct ttcacttccc   34020
atgttgctgt tggaaaatcc aaaagtattc tatttggcca ggcacagtgg ctcacacctg   34080
taatcccagc aatttgggag gccgagatta cctgaggtcg gaagttcaag accagcctgg   34140
ccaatatggc aaaacctctt ctctacaaaa aatacaaaaa ttagccaggc gtggtggcgc   34200
acgcctgtag taccagctat tcgggaggct gaggcacgag aattgcttta acctgggagg   34260
tggaggttgc agtgagctga gattgtgtca ctgcactcca gcctacgcga cagagcaaga   34320
ctccgtctca aaaacaaaa aaagtattct gttggatcgt ttgtgtgcga cgtgtttttc   34380
cctctcagaa agctcgtagg gtcttctctt tgtctccagc atggtctgga atttcccagt   34440
gagtgaccat ctgtgtgtgt gtattcatcc attccatgga gtccctgctg ggcccttgca   34500
```

```
atctggaaat tcatgcccat catttctgag aagttatcct gaacgtactg gttggtggtt    34560
tcctgtgctc catgttcttg cttcctgctc ttcggagctc ctgttatttg gttgagtttt    34620
gtctcctgga ctggtcctct cttacttctc ttgcttctcc catgttccat ctgttttcac    34680
tctactttct gtgagatcag gcccttttatc ttccaaccct tctattaggt ttgcaattga   34740
gtttgtaatt ccctagaaaa gttcttattc tctgaatatc ccttttgata gcatactctt    34800 ccttttttcat gagtgcagtg tttctgcatg gctctcatca gaacatgcta gtgtctccca   34860
tttctcataa ctttctagag tgaggaccat ttgaacttgg agtgccctca ttttaaaact    34920
ctgtggttga ccttgttccc ctcttttgct gctgcttttc accagacttt gaagaagcag    34980
aagtacattc agaacttgtc tgctctggca aaagacaata ctgttggctt aatctaaaaa    35040
ttgaagaaga aagctcaagg agagaagttt aaaaatatac cacctctggc tgggcgcggt    35100
ggctcacatc tgtaattcca gcactttggg aggctgaggc aggtggatca cctgaggtca    35160
ggagttcaag accagcctgg ccaacatggt gaaaccccgt ctctactaaa aatacaaaaa    35220
ttagccaggt atggtggcag ccgcctgtaa ttccagctac tcgggaggct gaggcaggag    35280
aatcacttga acccaggagg cagaggttgt ggtgagccaa gatcacgcca ctacactaca    35340
gcctgggtga caaagtgaga ctccgtctcc aaaaaaaaaa aaaaaaaaaa aatatatata    35400
tatatatata tatatatata tatatatata tatatatata cacacacact aaccttcagc    35460
atataggact attgcagaag ggattatctt tctacttggt tggttcctct tggtcttgag    35520
caaattttga cttccctgag ttggcccta aaagttaaag ggaaagggcc ttttctcttt     35580
cctttaaaac caatatggca tatttgctga gaacttagat accacaggat tggcagtgta    35640
gacttacatt catagaccgg atgccatcag ccaaccttga gtaatttgca gcacactgca    35700 tcatttatt taagtaatgc gaagtccttg acatgtctca gacattgtct tggttacttg    35760
taaggtctca cataaatcta attttcctct ttctctgccc tttctggttc agctcagttt    35820
attcaagggt gtatttgtgc aacacacttg aataaggtgt ggtcccgcct ttgtagatgt    35880
tatagtttgg gaagaccagc cgggcagaga aagagcatg attcaaggat gaaggcgtgg     35940
gctgggggcc gagggagcaa ggattcccag taacgaggga ggaaggagca gcaccatgtg    36000
cccattactc tatagacatc tcgaaccacc tggccatgta gctgtcatta acctaaattt    36060
acagttattg aaactgaggt tcagccaggc gtagtggctc acgcctgaac acaggaggcg    36120
gaggttgcag tgagccgaga tcacgccact gcactccagg ctaggtgaga gagcgagact    36180
ctgtctcaaa aaaataaat aaataaaaga aagaacaaa actgaggttc aaagaaatgt      36240
acagtgctcc cccccttatc caaagaggat acactccaag cccccacagt ggatacctga    36300
agcctcagat agtatcaagc cctatatatg ctatgttttt tccctgtata tgcataccta    36360
tgataaagtt tataaattag gcacagtagg agactaacaa caatgataat aaaatggaac    36420
aattataaca tacactgtaa caaaagggtc tcttcctctc tctctcagaa tatcttattg    36480
tactgtactg ggggtaacta aaaccaagga aagtgaaacc atggataagg gatatctact    36540
gtataaggtg gagtttcaa ggtcatagca ctgccttccc ctgaggttgg ccttgcagcc     36600
tctctaggca ctgctgctgc tgctaagaac ccctgtgagg tgaacactgt aagcatcatc    36660
attgcttctc agaagaggag acctggctta cagaggtcaa gcctcaggta ccttaaacac    36720
cattttaaaa ctgaactcat ggccaggtgc attggctcat gcctgtaatc ccttctctcc    36780
atgctcaaaa cctgccctcc ttgtctttat attccaaatt tcgtgggtgc cacctcctct    36840
gcccagtgac ttaagccaga gcatacattc atcctagact ctgtcccagg tccctggtcc    36900
```

```
aggcagctgc cagttgtcag gatcagctct ttatctcgca gtcctcctgc ctcttgtgtc   36960
attacccagg gctgtcacca tcttttcttg ggacagttac aacagcccg taaggagttg    37020 tgctgcttct agtcttgttc cctttgaatc tggattcctt cttgccatca agacaatcct   37080
gatacaaatc tgatcacgtc acacttccct tcaatagtct tccatggctc cttattgttt   37140
taggatgaaa tccaaactcc taaacatggg gattaacaat gtgccatgat tggcactgct   37200
ggcctctcct acctctgcag actcacctct tgccacttct cccttgaggt agatcaaaaa   37260
tggtcacaag ttctttgagg ctcttcccat caagaggtag agtttatttc cccacctctt   37320
ggatctggct tgccttgtga cttgctttga cccacagaac gtaacagaaa ggacactgcc   37380
taacttacaa atgaggtcta ccttaagagg ctttgcagat tccacattca acctcttgga   37440
atgctgccac catctgagaa gcctgaggtg gcctctgtga ggatgaaaga cttcatggtg   37500
agaaatacct agcgaacagc ctggcaccag ctaccaggca tgtgactgag gccatccagc   37560
catagctgag ccacaaaatg accacagcta tgtgaattat cccaggtcag accagtagaa   37620
gagccacctg gctgagctca gcccaatttg ctgacccata gaattgtgaa caaataaaat   37680
ggttgtagtt ataagccatt aagtttcaga gtttgttaca cggtaacatg taactgatac   37740
aactcttgga gccagttgtt cagccattct caaccactta ttcaatgatg ttttgggcca   37800
tatatgcaga tatgctgttc cttttccctt gaaatggccc ttaccctcct ttctgttggg   37860
ttttcctatg gaatatccag tcagccttta ggattcatct tgggtgtccc ttcctgtatg   37920
taggctccct ggccctccag gattccccca gtaacagccc tcatcatgct gcctttgcaa   37980
ccatttgttt atttgtacct ctcacctgct agttgggcaa gttactcact tctctcaacc   38040
tctgcatttt tcttctttat aaatgggacc aataatacct accctgccct ggcgtggata   38100
gattaaagaa aaaaaataca tgcagctgcc attgagggcc tggcccacgt gtgatgttca   38160
ataatattat ttctccttgt tttccttccc gtgccagtgc cacacccccc tgtcccagtg   38220
cactggggct gtggatccct tcaaagctga gattgcctgt ctgtggtctc cagcgttaag   38280
cacagtcatt agctcaggtg cgtactcatg tgttccacga gttcaagcct cagccctgta   38340
aagtttgcct gccgtgtatc tgatatattt ctgctaaaac ccattaggcc tttcttgctc   38400
tgaaatgtca tcgttagttg tgtgtcactt cagttttgta actggccagg ccactgcgcc   38460
caggctgctt cctcgtcatc tggctgctaa atgcttcaac cttacctgcc ttgctatgcg   38520
tcccatcctg tatcaggtca gagctcttga gtggtgaata caaatttcat ttcagttgac   38580
ttttgattct tgtggcaggc ctctcggcct actctaattt gattgcaacg gacacaaaat   38640
gtgtccaaac ttgcagcttt tcttctctta ttttgatatc accatccaca aaggtaagat   38700
attttaaagc aataactaca aactttctga aaattatgaa gaagtgctgg gttttaaatg   38760
gaagtcatat agtgtgaact ttgtgtaaag tccgtaggga gttttcttgg aaatggctgg   38820
gaacattctt tttgcacctt tgaagataaa ggtaggtgga ggagctcaca gctcttgtgc   38880
catgttgggc ttgtcactct tgtttatgtg ccaaattctt ttgattacaa aattttaagt   38940
ttaatgcttt aggtattgtt gggcaagatc tagatgtatc tagttaaatg taggtgatat   39000
gcaaactatt tatgatgtat ttgatttaaa ttcattaaga tagagtgtct ttaccaccat   39060
tatagtctgg tcctttttcct tctgttttaa atgtgtttcc attggcattt tctaaactga   39120
ctttgttagc gtgttaatca tttggcactg gtaatgatta atcttttctt tctttctatt   39180
tttttctttt tttttttttg agacagagtc ttgctctgtc accaggctgg agtgcagtgg   39240
```

```
cgcagtctca gctcactgca acctccgcct cccaggttca agtgattctc ctgcctcagc    39300
ctcccaagta gctagggact acaggcacgt gccaccacgc ccagctaatt tttgtatttt    39360
taatagagat ggggttttcac catgttggcc aggatggtct cagcctcttg acctcgtgat   39420
ccgcccacct cggcctccca aagtgctggg attacaggca tgagcgactg cgcccagccg    39480
tgttcatcta tttctgtgaa ccgatgctag gtgaaggtac agagggcttt ctagcttctg    39540
ggtttgttta ttctgaaatg ttattttaaa tcttagccca acaaattgag cgaaaagact    39600
tctagatgtt aaatatgata ttcaaaaaat ataaagacaa ggtgataaat tagaattggt    39660
gggaaagaga aaaatctgtc ttctgatggt cacctgcccc agcaacacta ctcgtttgag    39720
aagacttcca tcctttaccc tcaaagtgtt ccatgaggtt ggatcagaca tcatttagca    39780
aagaaagatg taaatagatt tctgtagggt ggcattatta agcatattaa gtggttacaa    39840
tacagtaaat tagagggagt agtacagaag cataagcagt caaaaaagtg aaagtctaac    39900
gttcgtaatt attgttctgg aggcttttgt atcacatata agttccaggc tgggtatgat    39960
ggctcacacc agtaatccca acactagag gccaagccgc gtggatcgct tgagcccagg     40020
agttcgagac caggctgggc aacatagtga aacctatctc tacaaaaata caaaaattag    40080
ctggggggtgg tggcagcgcc tgtagtccaa accacttggg agcctgaggt gagaggatca   40140
cctgggcccg ggagatcaag gctgcggtga gccatgatct tgccattgca ctccagcctg    40200
agtgacagag agagactctg tctcaaaaat aaaaaagttt tgagtgtgaa aattcaagct    40260
caattccatt tgttggttgt cttgagtgtc tgatcacata gaatataaag atgttttgat    40320
agttgggaca gtattcagct acctgctatt taatacatta tttcagaaaa tatttacaaa    40380
gggggctggg cacagtggct catgcctgta atcccagcac tttgggaggc cgaggtgggc    40440
ggattacctg aggtcaggtg ttcaaaacca gcctggccaa acatggtgaa accacatctc    40500
tactaaatat acaaaaaatt agccgggcgt ggtggtgtgt gcctgtagtc ccagctactc    40560
aggaggctga ggcacgagaa tcgcttgaac ccggggaggcg tggggttgca gtgagccgag   40620
attgcacaac tgcactccag cctgggtgac agagtgagac tgcatctata aaaacaacaa    40680
caaaaaagaa aatatttgca aaggaccttc tgggtccaag aacctcatgt ccaatacaag    40740
ggtgcacacg tgggtgagac acggcagctg ctctccagaa gcccacagtg gaggggtttc    40800
ccttcggtct ccttttattc caagcaagtg gcaaaactac tttactctta atacaaacca    40860
cttcctttta tcacaggacg cttcccaagc tctgcaactg ttgctcctga ggaagggagt    40920
ggaactgata atctgttcct ccctattgtg ttcagtatgg tttttttttt ttttttcctt    40980
ttgctggctt tgttttcctg tccctgtgat gattaaaatt cactctgcaa attagatcac    41040
ctttcccacg cagagtccct ttgacttctg ttctagatat ccattacatt tttgtagtct    41100
tcggacacac tgtgtgtgcc gctttgccct ctgggtgaca gcaggctgtg gctgcggcga    41160
cagagctgag gtgaattctc acagaccatc actgggttac tcctggagta agtaattccc    41220
aagagctcct tctgtgcaga tcgttagaaa tagatattga ggccaggcgc ggtggctcat    41280
gcctgtaatc ccagcacttt gggaggctga ggcgggcaga tcacgaggtc aagagatcaa    41340
gaccatcctg gccaacatgg tgaaaccttg tctctactaa aaatacaaaa gtagccgggc    41400
gtggtggcgc acgcccgtag tcccagctac tcaggaggct gaggcaggag aatcacttga    41460
acccgtgaaa cggaagttgc ggtgagccga gatcacgcca ctgtactcca gcctggtgac    41520
agagtgagac tccatctcaa aaaaagaga aagaaagaaa tagacattga acacctgcta    41580
cacagcaggg attgtgctag aagtatggat gcaaagatta ggtgaatatg ttccctagcc    41640
```

```
tcacaaagca tacagtctag taggagagac agacacgtaa aaagtttcaa cagcacagat   41700
aatcagggct acaccagaat tgggcccaag atgctgcagg aatctatagg tgaatgggtt   41760
tcatgaagga agagcttctt ctcccattta taactcattt tagcctaatc ttccaaacag   41820
tcacgcatct aagagcaggt gatgcagaaa atacccctcgt gttagttatg aattaccgtt   41880
ggaatccttc cagtgtttgc acctgccctg tgctcgggta acataaaaca gtgatataat   41940
ttgatgtcta cttcctcttg tatttgtctg tttttaagtg ttctacaatt ttcatatact   42000
ctgtttcatc gttctcaaag gaatattttg attgataaat gtttagttag taagacctaa   42060
aaactgaatc tcagtagttt gagcttatga tatacaagat gcagctctaa catttaaatt   42120
ggaagggaaa tgtcaaaaag atacctgcac tcttgtttgt tgcaacactg tttacaatag   42180
ctaagatttg gaagcaacct aagtgtccat caccagacaa atagataaag gaatgtgat   42240 atatatacac aatggagtac tattcagcca taaaaagaa tgagatcctg tcatttacaa   42300
caacatgggt ggaactggag atcattatgt taagtgaaat aatccaggca cagaaagaca   42360
aacttcacat gttctcactt atttgtgggc tctaaaaatc aaatcacttg aactcagaga   42420
gattagaagg atggttacca gaggctggga agggtggtga ggggttgggg gcagtgaaga   42480
tggttaacag gtacaaaaaa ctagaaagaa tgaataagac ccactaggtt ttttgttgtt   42540
ttgttgttgt tgttgttttg agacagagtc tcactctgtc acccaggctg gagtgcagtg   42600
gcatgatctc ggctcactgc aacctccacc tcctgggttc aagcgatcct cctgcctcag   42660
cctcccaaat agctgggatt atgggcacgc gccaccacac ctggctaatg tttgtatttt   42720
tagtagggac cgggtttcac caggttgaac aggctggtct caaactcctg acctcaagtg   42780
atccactcgc cttggcctcc caaatgctca gattacaggc gtgagccacc gcacctggcc   42840
actgtttgat agcataatag ggcgactata gtcaataata acttaatggt atatttttaa   42900
ataacttaaa gagtataatt ggattgttgt aactgaaagg atcaatgctt gagggcacag   42960
ctaccccatt ccccatgacg tgtttagttc acattacatg cctatgtcaa agcatctcat   43020
gtaccccata aatatataca ctgagtatat accacaaata ttttaaataa ttttttaaaat   43080 aaaaaaataa attgtaaggg aaagaaaatt atgaatttag aaatgtaaaa ggtctcaggt   43140
aaggaaggaa tgagaggatc atgcagaacc tcccatcatt gctgggactg aacagaagc   43200 cctaccttt cccaacaccc tatccacctg tccctcacct ctcagctttt gtgagactct   43260
gtctgtgcta tgaaactgaa gatctaattc agtgctgttt gcattgtctt gcctcctgga   43320
ccagaggttg cagttgttga gaaagggat ggttggttat gccttgatcc ccccagagc   43380 atttggggca taggacacgg gaactggcca gcctggttca ctcttctcga ttagctggac   43440
agcggcatgt catgtgggta ataggaaggg gtggggactg ccccgggata ttctgctcct   43500
gatcagaagc gccagtgatg tggggggagc cccagcacca gagcatgctg ggagggcgtg   43560
cagggtgggg caggtgcccg tttggcctct gctgtctatc tggggatgc atccaaaggc   43620 aactgttcct tatctgctct tgttgggagc aaggaagggc caatttgttc aatgatccgt   43680
atacagccag tccctctggc cagagttcaa gacagtattg cctcactcta tatagagatt   43740
gtatcttggt tagctcttca ttcatagcaa gaccaatgtt tctgtaaatt aatcctggta   43800
ttgtttaaaa gcaactaaaa atgatgaaat tgtaaaactt tgaaactccc tgaatataac   43860
gacaagcaaa ctaacattgt tttattggtc gatgctcctg gccagaagag agaatattag   43920
cagggataaa aggcataggc cacatgcatt ttccaccccca gtgctgagaa cacgatgggc   43980
```

```
gaaaaaggga ggtggccaca gcccatccat cacacagtct ctgcccatct acttgctttt    44040 tcctttttt ttttttttt ttttgtgaca gagtctcgct tgtcaccca gactggaggg      44100 cagtggtgca atctcagctc attgcaactt ctacctccca ggttcaagcg attctcctgc    44160
ctcagcctcc cgagtagctg ggattacagg cacctgccac caagcccagc taatttgttt    44220
gtatttttag tagagacggg gtttcaccat gttggccagg ctggttttga actcctgacc    44280
ttaagtgatc agcccacctc agcctcccaa agtgctggga ttacaggtgc gagccaccac    44340
gcctggcccc agctacctgt tttctttctt tttttttttt tttttctttt ttttgagaca    44400
aagtcttgct cttgtccccc aggctggagt gcaattgcat gatctcagct cactgcaacc    44460
tccacctcct gggttcaagc gattctcttg cctcagtctc ctgagtagct gggattacag    44520
gcgcctacca ccacgcccgg ctaattttg tattttagt agagacgggg tttcaccctg     44580
ttggccaggc tggtttcgaa ctcctgacct taagtgatct gcccgcctca gcctcccaaa    44640
gtgctgggat tacaggtgtg agccaccatg cccggcccca gctacttgct ttctattggg    44700
atgaacctca tggttaatac agttagttag tgactgcaac ttttgaactt tttgttcata    44760
gtgaaaaata ttttaagtaa tgcttacccc attatgtttc ttgtcatttg aaaaaaaatc    44820
tcccttcaga cagaatgcag aataaaatac tacagaaaat ctgtacagag tcccagcctg    44880
acttatgcta gtaggttaca gagaaagaaa gtcttctaaa ccctatgaaa ggttaacagt    44940
tctcttattt ttccctgtgt gctatttgat gatttccctg tgaactttga tgattttattg    45000 ccagaattcc aaacataata tgtgaatttc acaaaaatgg atgaaatgta tctatttttc    45060
attggtagaa gaagccaaaa catcccttcc tcaccgcact aaaagctgtt gtttacatga    45120
agcaaacctc aaatgtgaac atatttttac gcaaatgcat ttaatgggtg aatatttgct    45180
ttgggacggt attctttact ctatctggag agtctggcgt tccgtaatca ccatgtgatg    45240
acggctgccc tgacagtggc tggtagcagc acatacccccc gagcctctcc gtggtgtgcg    45300
ccgtgggcac catgtgacca ttttcagaaa ggaagacagt tctggaagct aaaggtcacc    45360
tagtcagcct cgttgggtga ttgatgactc agctgggttc agggaggtgg acccgaggca    45420
gagcctctag aaggcagcgg tgggcagggc ggttcaggca ggtggcacct gggcaaaggt    45480
gcagacgtgg aatcctgaaa gcaattctca gcgctgctgc gtttccagga ggtagaagaa    45540
cagtgacaag tgcacagtcg ggtagggaca aatgtggaag ggctgggaac agtgtgttca    45600
ggagactggg cttcaatctg gaggtctcag gaagtggttt aggatgtttc agcgagagca    45660
tgatacagac taaccaggaa agaaccgctg cttttgtcact tatacccta tggaaatgcc       45720 gttcgctttg ctagttgaaa tagcctacca ttgtctggga ctcacccagt tagatttgtt    45780
tggactccac aaagtattct tgaccataca atcatggtcg aggaccccct acatgagctg    45840
ccttcatggc tacagggaga gcacaccaaa gtggatgtca cacccagcac acatgccacc    45900
ggcttggccc tgcgccccgc agcctgagcc acactggctg cctgttcctg gaatgtgcca    45960
acatgtttca gtcctggagc cttttgcactt ggtgttctct tcgctggaac attctccccc    46020
aagacattta cacagcttgc cccctcattc cctgaggtta tctcctgccc cctaatcagt    46080
gaggccttcc ctggcctcac cccggacact ccacacgtgc attcatttcg ttgttcacca    46140
tctgtgtccc agttacaagg gaggctccct gagagcaggg atctgatttt tgttagttgt    46200
tgttgttgct gttttgaggt ggagtcttgc tttgtcgccc aggctggtgt gcagtggtgc    46260
gacctcagct caccgcaacc tccgcctccc atgttcaagc ggttctcctg cctcaacctc    46320
ctgagtagct gggattacag gtgcctgcca ccatgcccag ctaatttttg tattttagt    46380
```

```
agagacagag tttcatcatg ttggtcaagc tgccctccaa ctcctgacct cgtgatctgc   46440
ccacctgggc ctcccaaagt gctgggatta caggcatgag ccactgcacc cgaccctgtt   46500
ttttgtttgg ttttggtttt ggtttggttt tggttttttt ttgagacacg gtctcactct   46560
gtcgccccgg ctagagtgtg gtggcaccat ctcggctcac tgcaacctcc acctcccagg   46620
ttcaagtgat tctcctgcct cagcctcctg agtagctggg attacaggca catgccacca   46680
cacccagcta attttgtat ttttagtaga gatggggttt tgccatgttg gccagtctgg   46740
tctcaaactc ctgacctcaa gtgatccgcc cgcctcggcc tcccaaagtg ctgggattac   46800
aggtgtgagc cactgtgccc ggcccaggga tctgttttg tctccgctgt gtccccagca   46860
cctcaaacat attgtacgga gctgcgacag ctgcgcagtc agtgatgact gagagattcc   46920
tggccccgtg ggctatggct ccttcaacag tttgttgttt aaaggttctt cactttctca   46980
gcgtgctgat caagagacaa gcctggagga gaggctcagt ggtgctcctg tgtagatgat   47040
gaattcaggt gtatcttgga tggtaaatga cgttgcattt aaaaccaagc aagtggccag   47100
gcgcagtggc tcacacctgt gatcaaagca ctttagaagg ccgaggcggg cggatcacct   47160
gaagtcagga gtttgagacc agcctggcca gcatggtaaa acccgtctc tactaataat   47220 acaaaaaaac tagctgggcg tggtggcggg cacctgtaat cccaaccact cagaaggctg   47280
aggcaggaga attgcttgaa cccgggaggt ggaggttgca gtgagctgag atcgcaccac   47340
tgtactccag cctgggcgac aagagcaaga ctctatctca aaataaaaa aaattaaaaa   47400 ttaaaattta aaattaaaac aaacagccgg acgcagtggc tcactcctgt aatcgcagca   47460
ctttgcgagg ctgaggcgag cggaatacga gctcaggaga tcgagaccac cctggctaac   47520
acagtgaaac ccgtctctac taaaaaaaaa aaaatacaaa aaattagcca ggcgtggtgg   47580
caggcgcctg tagtcccagc tactcaggag actgaggcag gagaatggtg tgaacccggg   47640
aggcggagct tgcagtgagc cgagattgtg cccctgcact ccagcctggg caacagactg   47700
agactctgtc tcaaaaaaaa aaaaaaaga ataaataaat aaataataaa aataaaaac   47760 aaacaagtga acgttgttat acgtcagtct taccaattgt tcctcttcc tcccagtagc   47820 ttggagctcg gcggcacaac cagcaccatc tggtcgcgat ggtggacacg gaaagcccac   47880
tctgccccct ctccccactc gaggccggcg atctagagag cccgttatct gaagagttcc   47940
tgcaagaaat gggaaacatc caagagattt cgcaatccat cggcgaggat agttctggaa   48000
gctttggctt tacggaatac cagtatttag gaagctgtcc tggctcagat ggctcggtca   48060
tcacgggtaa gtgtgccgtt tcctagaaag ttttatttag aaatgtttct tcctccaaga   48120
aaactgttct ctctttttt ttttttttt tttgagacgg agtctcgctc tgtcgcccag   48180
gctggagtgc aatggctcga tctcggctca ctgcaggctc cacctcctgg gttcacacca   48240
ttctcctgcc tcagcctccc gagtagctgg gactacaggt gcccgccacc acgcccagct   48300 aattttgta ttttaatag agacggggtt tcactgtgtt agccaggatg gtctccatct   48360
cctgacctca tgatctgccc gcctcggcct cctaaagtgc tgggattata ggcgtgagcc   48420
accgcgcccg gccgaaaact gttctcttta gctggaaaag aagtcacact tttttgcaaa   48480
gaaagcttca gacgtggtaa agcatgacct ccagtgcccc tgggccctgg aaggcgcgtg   48540
tcacggctca cggtgccccc tcttgtgaaa gccatgcaca catcaaacag tgcttgagat   48600
tcagtcacgg ggaacagcta aagtacacag accctaaccc cagcaagccc gcggggggca   48660
gctagacatt tttaagagga gacgtgtgca agggtctgca tagaggtact gttggtaaga   48720
```

```
gggaaggatg ggaaacaagc tgtacatgcg tcaaagggaa acagataaat tgggatgcat    48780
ttatacagtg gtatatactt catagcaatt taaaagaaca gactaggcta ggcgcggtgg    48840
ctcacgccta taatcccagc actttggaag gccgaggcaa gtggatcact tgaggtcagg    48900
agcttgagac cagcctgacc aacatggtga ggccccatct atacaaaaaa aatttaaaat    48960 taaaaaaat tagccaggca tggtggtgca tgcatgtggt cctagctact caggatgctg    49020
agggaggagg accacttgag cccaggagct cgaggctgcc atgagctatg actgccactg    49080
cactccagcc tgggtgacag tgagaccctg tctttaaaaa aaatttttt taagcaacat    49140 tgaatgaaaa taaacaagct taatgaatat ttttatgatc caattaatgt aaaatctttt    49200 atttttatt ttttgagaca gagttttgct cttgttgccc aggctggagt gcagtggtat    49260
gatctcagcc cactacaacg tccatcttcc gagctcaagc agttctcctg cctcagcctc    49320
cctagtagct aggattacag gcacccgtca ccatgccggg ctaattttg tatttttagt     49380 agagatgggg tttcaccgtg ttggccaggc tggtctcaaa ctcctgacgt caggtggtcc    49440
gcctgcctca gcctcccaaa gtgcagggat acaggcatg agccactgca cccggcccaa     49500 ttaaatctt taacactaaa caatctagta catcactggt ggaaacagac atacacctat     49560 tgcaagggc atctcagctt taaggactca gtcacctcct gagcaagatg gagggagaac     49620
tggggagggg tcccatgggg actgtaattc tctctaggtt gtatatttt aaaagacttc     49680 agcagtgtga taaacctggg tggtgtgtac atgggtatta cagtcatgtt gcttaatgac    49740
agggacaggt tgtgagaaat gcatccttag gtgatttcat cattgtgtga aagtcataga    49800
gtacacttaa acccagatgg tagagcctgc tgcacaccga ggctctgcgg tgcagcctgt    49860
tgctccaagg cacgcacctg tacagcgtgt tactgtactg aacggcgtag gcccctgtga    49920
cacaatggta agtatttgtg cgtctaaaca taccaaaaca tatagtagaa aaggttacag    49980
caaaaataca gtattatcat cttatgggac catgatacca cagttgaact tatggtctat    50040
tgttgaccaa aatgtcactg tgcagtgtgt gactatacag aaataagctc agagaaatta    50100
agtaacttgg ctgggcgcag tggctcacgc ctgtaatccc aacactttgg gaggctgagg    50160
caggcggatc acccgaggtc aggagttcaa gaccagtctg gccaacatgg caaaccccca    50220
tctctactaa agaatacaaa acattagctg ggagtggtgg caggtgcctg taatcccagc    50280
tactctactc aggaggctga ggcagggaga attgcttgaa cccaggaggc agaggttgca    50340
gtgagcagag atcatgccac tgtactctag cttgggcgac agggtgagac tccatctcaa    50400
aaaaaagttg gggcgtggtg gctcatgcct gtaatcccag cactttggga ggctgaggcg    50460
ggcggatcac ttgaggtcag gagttaaaga ccagcctggt caacatggtg aaaccccatc    50520
tctactgaaa atacaaaaat tagccaagca tggtggtaca cacctgtaat gcctgggcaa    50580
cagagcaaga ttccgtctca aaaaaaaaaa aaaaaaagt aagtaacctg ccacggttca    50640
tacagccaga aagacacaga gccgggcctg gaccccgcct tcagcttgc tctagagggc     50700 tattctctgc atgctggcat gatcgcgcct tgtaaaaggt ggcagtgttc tcagcttagt    50760
caatcaggaa ttgcaagagg caagtgagcc cctgaggact ctgggggcc tttgtgaccg     50820 agcagctttg ggagtgaccc tgacagacct ttacaggtgg tgcaagtttt gactcccttt    50880
ctcctggcgc gttaagcaga ggataagcgc tgtgaaggaa gtgaaggtgt agggagatca    50940
tggcccccag agcagtgggg aaggggacag ggaggctgga ggagagcaag gaaaaggctc    51000
cgtgtcaggt ggcgccttga gtggcctggg taggttgtct tgcagtgaac ccgggttaat    51060
ggccttgaca atgaccgcat tgtttcctga gcactgcagg ctgcccacac acctcacacc    51120
```

-continued

```
tcggcttgcc taagcccaga gcagccttgt gaggtcgttg ttatgtttat ttaaggaagg    51180
aggaaaggag gcaggtccca ggacatcctg acgtgctgga gatcaccagc ccagaaccca    51240
gctcttaacc ccacaatgtg ggaccttct tcacccatca cagacacacc ccatgctggt    51300
tcaccgtttt cctataatga ctatttgtgc tatttattag aaaaatcttt tccttatgga    51360
tttgaaaaga tttatcttgc ttttgttttt cttttttgcc tttctttttt aaggcaggca    51420
ggctcccgca gccccacccc cagggtgaaa aatatagttc attgtctagt aaagagttc     51480 agagatacac ttttttcttt gggtaagata tactctagag cttgttctga aatatggaat    51540
ttgtgtgagc tgcgggagtg ggtgggtgtg tggctctagc tctggaaagt tctttcctgg    51600
cagtggccag gagggctgcc cagcccctc ctgcctcctc tggcagctta aacacaggac     51660
cccttattct gtgctctctc ctgacccctg gtcctcatgc aggagggaac cctgctcttc    51720
tagggtcctt ttctaaaagt agtgtctttt aggtcattgt caagaactat aatctaaaat    51780 gtattttaa ctcatctgga aattctgaca gaggtaaggc ttgagaattt cctgcatact     51840
agccttgtgg tctatataat ccattaaaag ccacatttaa cccaattcca cagactgaac    51900
tgtgcttccc atctaaataa attaaaagca ggccgggcac ggtggtcacg tgtgtaatcc    51960
cagcactttg ggaggtcgag gcgggtggat cacctgaggt caggagttcg agaccaacct    52020
ggccaacatg gtgaacctc atctctacta aaaataaaaa aaattagctg ggcgtggagg     52080
cgtgcacctc ttaagcttaa ggacatattt cttatgatcc aattaatgta aaatatttta    52140 tttttatt atttttgag acagagtttc actcttgctg cccaggctgg agtgcagtgg       52200
tgcgatcttg gcctgtaatc ccggctactc aggaggctga ggcaggacag tcgcttgaat    52260
ccaggaggcg gaggttgcag tgagccaaga tcacaccact gcactccagc ctgggcaaca    52320
gagtgagact ctgtctttaa ataaataaat aaataaatag cgagggttca gggcaggaga    52380
aaaagggttc caaatttgtt ctgaaccaat tccaaggaac tttatggcac aaagaaaaaa    52440
aaggggaact tacaaaaagt gaccacactg aagcgtcctg gtcacccatc cctggttttg    52500
accaccagcc tttaaagtgg caagcgggtg ataacccatt tcttatttcc ccctcagcat    52560
ttcctcactg ttattcatac atgtggtcat ttgtactcat ctcacaattg ttaaaacctc    52620 tttcctcct tccaggtttt actgaactgt tactgcgaag tctgagagat gaggtcattt     52680
aagattattt cttatttgta aattagatcg ttcatatttg tacctaatct gatcttttgg    52740
gtaatattcc tagttatgta gactggtctc tcagaagagc cggatattaa atgcagtact    52800
ttaaacttta cacccaggag accggatggg tgaggctggt tcactcggcc aaagtaccat    52860
tttatctctg cttttcttc ccggctttat tgccataatt gacatacaat aaactgcatg     52920
tatttaaagt gtacaatctg ttgggtgtac acacacacgc atctgtgaaa ccatcatcac    52980
actcaaaata gtgatgtaga aattttgctc cttagttcga ctaaatctgg gttcttgtgt    53040
catgaccagg aaaaattagg cacgtggaca cgttgaaggg tgaggagagc agtattgggc    53100
gaaaaggaaa aagaaaaaa actctcagca aagctagagg ggatcctgcc aatgagttcc     53160
cagctcacag actgattagc aggccaccac acatgagctg gaggccaggc tcctcccgct    53220
gcgcaaggtg agaacttccc gtggctccac cccattctcc caatgcccag gtgggtcccc    53280
gtcccttgcg ggcctgtcca gacaagggaa ccctgggcag gttccctcat ctacacaaaa    53340
gcacctgagg taaacacttg tggggcaggt tgcagattct ctgggacgc ccccttctc     53400 tgcctcctgc atctatcagt agtgcctctg tctgtcaccc ctaaagttta cttgtgctgt    53460
```

```
ttctaattcc tctttcccca gccccgtgcc tccctgcctc cctcccccag taaaccatga    53520
atccactttc tatcattcta ggttgcttta tatttcctag aattttatat aaatggaatc    53580
atacagcacg tactctttct aggctggctt ctttcactct gcagaatggc tgtgagactc    53640
atctgcattg cagcaagcat caatagttca ttcttcatcc atcatgtgga catagcacag    53700
tttgctgatt cacgcacctg ttgatgagca tttaggttgt ttctagctta tggctattac    53760
aaataaagct gctatgaaca ttcacgtaca agtctctgta caaccctctg ctttcatttc    53820
ttttgaataa ataacctagga gtatgacggc tggaacagat ggcaggtgtt tgtgtaactt    53880
tttaagaaac tgccaaaatc ttttccagca tttcagaaaa atcttagaaa atgctatact    53940
atgttatatt cccactggca gtatatgggg gagttccagt tcctccatac cctcatcaac    54000
atgaggcatg atcagtcttt ttaatttaa ccatgtcagt aggtgtgtga tggtctctca    54060
ctgtggtgat ttttatttgc acttccctgg tgattttgag catcttttcg tatgcttatt    54120
tgccatatat cttctttggt gatatttctg ttcaaagcct ttgctcattt tttaattgag    54180
ttgcttttct actattcact attgaacact atttatatat tttgaataca atactttat    54240 cagacatgtg atctacaaat attttcccca gtgtgtggtt tgtctttctt ttctttctac    54300
tgatagtatc ttaaaaaaaa aaagaaaaa agattgtttt gtttgttttg ttttgttttt    54360
gagatagggt ctcaatctat tgcccaggct agagtgcagt ggtgcgatca tggcttactg    54420
cagccttgac ctcttgggct caggaaaccc tccgacctca gcctcccaag tagctgggac    54480
cacaggtgtg taccaccatg cttggctaat tttttttttt tagatacaga gactcgttat    54540
gttgccaggg gtggtcttga actcctggac tcaagcgacc ctcccacttc ggcctcccaa    54600
agtgctggga ttacaggtgt gagccatcat gcccgaccag ttcttaattt tgatgaagtc    54660
caatttatca atgtccttt tttatggata cttcatttat ttatttattt gagagagggt    54720
ctcaccctga gcccaggctg gagttcagtg gcatgatctc agctcactgc agcctcaacc    54780
tcccaggccc aggtaatcct cctacttcag cctcccaagt agctgagact acaggtacct    54840
gccaccatgc ccgggtaagt ttttttgtatt tatttgtaga gacggggttt cgccatgttg    54900
cccaggttgg tctcaaactc ctgggctcaa gtgatctgcc catctcagcc tcccaaagtg    54960
ttgggattac aggcgtgagc caccatgccc agccatatat atatatatat atatatatat    55020
atatatatat tttttttttt tttttttttt tttttttttg agacagagtc tcactctgtt    55080
gcccaggctg gagtgcagtg gtgcaatctt agctcactgc aacctccttc tctgaggttc    55140
aagtaattct catgcctcag cctctttagt agctgggatt acaggcatgt gctaccaggc    55200
ccggctaatt accagcctta tattttgaa ctctgtttaa aacatttagg tgcataaaca    55260
ttcaggcttg ttatattctg ttgatgaact gaaccttta ttattatgaa attgctgttg    55320
taatccgtgg taaaattatt tgttctgaac actactttgt ctgttattga tgtagccact    55380
gcagctttct tttgattggt gttaacatgg tatatctttt cccattcttt ttcttttaac    55440
tggtttgtgt cttatacta tggtttgatt taaatctatt atctcacaat ttgttctctt    55500
tggtacatct ttgttttgtt ccctttttcct ctttttatgc cttctgttga attaattgag    55560
tcttttttgt tttgtttcat ttaattttgt ttttgagac ggagtctctc tctgtctcca    55620
ggctggagtg caatggcgct atctcggctc actgcaacct ctgcctcctg gttcaagca    55680 attctcctgc ctcatcctcc tgagtagcta ggatcagagg catgcaccac cacgcccggc    55740
taatttgtgt gtgtgtgtgt gtgtgtattt ttactagaga cggggtttcac tatgttggtc    55800 aggctggtct caaactcgtg accttgtgat ctgcctgcct tggcctccca aaatgctggg    55860
```

```
attataggcg tgagccaccg cacccagcct aattgagtca ttttttaagat tccactttat  55920 ctcctttgtt ggcttattat ttataacacc ttctggtgtt attttagtag ttgcttttagg  55980 gtttatagtg tatctctcta atgtctccca gtctaccttc cagtggtatc attctatctt  56040
acagatatta taagaacttt atgacagtat actttcattt ttcccttcat gcatttgtgg  56100
taatgtttca cataatttta tttatttacc tacattataa atattacaat atgttattgt  56160
tttacataga cagccggtta tcttttttaag atagtagtaa gaaaaatttt ttacatttac  56220
ccacataatt acctttttcta gtgctatata cctttgtata aatccagatt tccatctgct  56280
atcattttcc ttctgcctga aagacttcct gtgatattat ctataatatg gctctactgg  56340
taacgaatta ctagcttttg tatgtctgaa aaagtcttca tataaccttc attctagaaa  56400
gtatgtgatt caaagggccg ggcacagtgg ttcacgcctg taatccgagc actttgggag  56460
gccgaggcgg gtggatcacc tgaggtcagg agttcaagac cagcctgacc aataaggtga  56520
aaccctgtct ttactaaaaa tacaaaaatt agctgggcat ggtggctcat gcctatagtc  56580
cctgctactt gggaggctga dacaggagaa ttgcttgaac ccaggaggca gaggttgcag  56640
tgagccaaga tcacgccact gcacaccagc ctgggtgaca gagcaagact ccatcccct  56700 gcaaaaaaaa agaaaaagaa aaagaaaaaa gtatgtgatt ctacattggc aattttttttt  56760 ttttttttt ttttgagaca gagtctcgct ctatcaccca ggctggaggg cggtggtgcc  56820
atcttggctc actgcacgct ccgcctccca ggttcacacc attctcctgc cccagcctcc  56880
caagtagctg agattacagg cacccaccac cacacccggc taattttttt gtatttttta  56940
gtagagatgg ggtttcacca tgttagccag gatggtctca atctcctgac ctcatgatcc  57000
gcccacctcg gcctcccaaa gtgctgggat tacaggcatg agccaccgag cctggccact  57060
ttttttcttt aaatgctttt aagatgttcc tactatcttc ttgttttaaa ttaattaatt  57120
tattattatt attattatta ttattattat tatttttttt ttttttttt ttttagaga  57180 cagggtcttg cgctgatgcc gaggctggag tgtgctagtg ccatcgtagc tcactgcagt  57240
ctcaaacacc tggtctcaag caatcgtcct gcctcagcct cctgaggaac taggactaga  57300
ggtatatact accatgccca gccaatttta aaaattttt gtagaggtgg agactcgcta  57360
tgttgaccag gctcctctcg aactcctggc ctcaagcaat cctcctacct ctgcctcccg  57420
aagtgttggg attacaggga ttacaagtgt gagccactgt gccagtcccc actgtcttct  57480
ggcttgcatc gtttctaaaa gaaacttggt gtcatcctta ttttttgttc tctacatgtt  57540
atatgtcctc tttatctggt tgctttaact ttatttatta atttagttt aatttttaat  57600 tgacaaataa taattgtatt tttatggggc acaatgtgat gttttggtct atgtttacat  57660 tgtgaatgt gtaaatcaag ctagtgaaca tatccaccac ctcacacact taccattttt  57720
tgtgtgtggt gagaacatgt aaaggctgct ccttgaggcc aggcccaatc ccagcacttt  57780
gggaggccga ggcgagtgga tcacttgagg tcaggagttc aagactagcc tggccaacat  57840
ggtgaaaccc cgtccctact aaaaacacaa aaatcagcca ggcgcggtgg tacacgccta  57900
tagtcctagc tacttgggag gctgaggcag gagaatcact tgaacccaag aggcagaggc  57960
tgcagtgagc caagatcatg ctactgcact ccagcctggg caacagagca agactccatc  58020
tcaaaaaaaa aaaaaaaaag tctattcctt gagcaatttt gaaatacaca atacatcatt  58080
gttaattatg gtcaccatag tgggtagtag atcactaaat cttattcttc ctgtctaact  58140 aaaactttt tccttttgac caacatctcc ccattccctc cctcaacctc agcccctgat  58200
```

```
aaccaccatt ccactctcta ctgctatgag tttgaccttt ttagatttca catatgagat    58260
cacatggtat ttgtctttct gtgcctggct tcttttactt agcataatac cttccagatt    58320
tacccatgtt gttgcaaatg gaatttcctt cttttttaag gctgaatagt attcgtgtgt    58380
gtgtgtgtgt gcgtgtgtgt gtgtgtgtgt atcacatttt ctttatctct tcgttcatta    58440
atgatcattt aggatgattc cacatcaggc tactgtgtat agtgctgcag taaacatgga    58500
agtgtagaca tctcttcagc atactgcttc caatctcttt ggatataaac ccagaagtgg    58560
gattgctgga tcatatgtag tgctattttt gttttttga ggaacctcca tacttatttt    58620
gcataatgct attctaattc acaatactac caacagtgga catgggttct tttttctcta    58680
catgcttgcc aaccacttgt tatctttat ctttttatat atctggctgc ttctaaattt    58740
ttttctttct taccaattct gaaccatttg atggtttctt cctttatgct ccttgtgctt    58800
gaggttcatt gagcatctgg gatcagtgca cttattgttt tcatcaaatt cagaagatta    58860
ggccattatt tcttcaaact ttttttgtcgt tctctgtcta cctttgagag ctccaattat    58920
acatacatta ggccacttga agttgtcatt acagttcact aatgctaagt tctttttta    58980 agtcttgttt ctgtgtttca ttttggacac tttctattgc tacatcttca aatttactaa    59040
tttttccttc tgcaatatct aatctgctcc taatcctatc cagtgtattt tccatattag    59100
atattgtagt tttcataact agaagcatga tttggttctg ttttcaccca tgtatctata    59160
taacatgtcc agtctttcac tcagcttctt aaacatttag aatatggtca gaataacttt    59220
ttttgctgtt ttgttttaga dacagggtct cactttgtta ctcaggctgg agcgcagtgg    59280
catgatcaca gctcactgca gccccaacct cctcgtctca aggaatcctc ccacctcagc    59340
ctcctatgta gctgggacca caggtacaca ccaccacacc tggctaattt ttaaattttt    59400
tgaagagacg ggtctcactt tgttgcccag actggtctca aactcctggg ttcaaacaat    59460
cctccagcct tggcctccca acgtgttggg attacaggca tgagccactg tacccagccc    59520
agaataactt tttaaaaatg tcttgaggcc gaggttggga aataatctga ggtcgggagt    59580
tcgagaccag cctgaccaac atggagaaac cccgtctcta caaaaatac aaaattagcc    59640 aggcacagtg gcacatgcct gtaatcccag ctacttggga ggctgaggca ggagaattgc    59700
ttgaacccgg gaggcagagg ttgtggtgag ccgagatcac accattggac tccagcctgg    59760
gcaacaagag cgaaactcca tctcaaaaaa aaaaaaaaa aaaactctta gccacaattt    59820
ctatcatctg tgtcacttct gagtcccttt ctattcagtt attttctcc ttgtcatggg    59880 tcatattttt ctgattcttc atgtgtcctg taattttctt ttctttttt ttttggagat    59940 ggagtcttac tctctcaccc aggctgtagt gcgatggcac aatcttggct cactgcaacc    60000
tccacctcct gggttcaagt gattctcctg cctcagcctc ccaggtagct gggattacag    60060
gtgctcacca ccatgcccag ataattttt gtattttag cagagacggg gtttcaccat    60120
gatggccaag ctggttttga actcttgacc tcaagtgatc cgcccacctc ggcctcccaa    60180
agtgctagga ttacaggcat gagccaccgt gcctggccag ttgttctcat tggatgtcat    60240
atgttgggaa cttattggg tgatggatat ttttgatttc ctataaatat tcttgaactt    60300
tgttctggga tgcaattaag ttacttggaa aatctttgat cctttcaggt cctgtttctc    60360
agcttcatta gatgggacta tcacagtgtt tgttttagag ataactttgc cccactgctg    60420
aggcaaaacc actttgagct tcacctgatg ccccatgact tcagtgatct tccactgtgg    60480
gaggcgagag caggactata tccagctcca tgtgggcccc aggcagcgtt cactatcatc    60540
atttcaggtt gctactgaag tatccctttt tcaggctctc agctggcaga gcaaatacat    60600
```

```
atatgtatac atactaacct atgtctatac aggaatctat cggtatttct gtctgtggcc   60660
atctgtagct gtatgaagcc aaacatgagt gtgtgctgat gtctccagcc ctcatctgtt   60720
accagatgga tcgttctagc ctcctccact tgcctacctg tcaattcacc attccttgag   60780
ttcatggttc attttcagta tacctgcaca gtggtatcag aactgttaac ccacaccctg   60840
tgggaaaaaa actccatcag ctagagcaca gtgtttacag ccagatcctt ttgcctttag   60900
tcttacagat tccaatcatt ccaaattatt cggtgcagcg cctttccgca cctgcaccca   60960
cttttttccc tgagattgtt tcctacattc gtagcacagt tagattgttt tgttacattc   61020
tgcatttcac cctgggatcc tccaacctcc taagttattt ttgtttattt tgcacacatt   61080
aggttcaatc tgaactataa agttctgtgg gttttcacaa atgcgtagtg tcatgtatcc   61140
accactacat tttccttctc tctctttctt gctttctcgc cttcttgtct tgctctgtca   61200
cccaggctgg agtgcagtgg cacaatctcg gctcactaca acctccgtct cctgggttca   61260
agccattctg ctgcctcagc ttcccgagta gctgggacta caggcacgca ccaccaccc    61320 tggctaactt tttgtatttt tacaaaatac aaaagacgat gtttcactat gtgggccagg   61380
ctggtctcga actcctgacc ttgtgatcca cctacctcgg cctcccaaag tgttgggatt   61440
acaggcgtga gccaccacac ccggtctctc tccttccttt cctttcctct cctttccttt   61500
tctttctttc tctttccctc tcctctcttc tcctctcctc tcctttgatg gaggtctcac   61560
tgtgacaccc aggctggagt acagtggcag cataatctca gctcactgta gcctcagcct   61620
cccagggctc aggtgatcct cccacctcag cctcccaagt agctgggatt acaggtgcac   61680
accgctgagc ccagcaaatt tttgtatttt ttgtaaagat agggtttcac catgttgccc   61740
aggctggtct caaactcctg agctcaagtt atctgccagc ctcggcctcc caaagtgctg   61800
ggatgacagg catgagctac cgtgcccaga ccactgttag attttcatat gaatagtttc   61860
accacatcaa aaaccccat gcttcaccta ttcaaccctg cctctcccac ccccagccag   61920
ctcagaaatg gttctttta ccattgctat aattttgcct tttccagaac gccatgaatt   61980
tgaaatcata tagtatgtag cctttcaga ctgacttctt tcatagcaat atgcatttaa   62040
gagtcatcca tgtctttcca tggcttgata tctcatttct tttacactg aatgagttcc    62100 cactgtctgt ttgtaccaca gtttgtatat ctattcacct atctaagggc atcttggttg   62160
cttccaattt ttggcaatta ataaagctgg ccatgcacag tggctcacac ctgtaatccc   62220
agcattttgg gaggccaagg cgggcagatc acttgaggtc aggagtttga ccagcctg    62280 gccaacatgg tgaaacgctg tctctactaa aaatacaaaa attagccggg cgtggtaatg   62340
ggcacctgta atcccagcta cttggaaggc tgaggcagga gaatcacttg aacctggagg   62400
cagaggttgc agtgagctga gatcgtgcca ctccactcca gcctgggtga cagagtgaga   62460
ctctgtccca aaagaaaaa gaataaactg ctgtatacat gtgtaggttt tgtgtggaca   62520
gaagttttca aatcagttgg acaaataccct aagagtgtga ttccatcata cagtaaaact   62580
gctttgcttt gtcagaaact gccagaatgt cctccaaggg ggctgtctca tgttgcattc   62640
ccaccagcaa tgaatggggg ttcctgttgc tccacatcct caccagattt gatgatgtca   62700
gttttgtgga ttttagtcat cctagtaggt gtgtggtgac accacattgt tgttctcatt   62760
ctcagtgccc cgatgacata tcatgctgag cattgtttca tatgcttact tgccatctgt   62820
atatcgtcct tgctgaagtg actgttcaga tgttcagatc ttttgcccat tttcttctt    62880 tttttttttt ttttcctttt tgatacggag tcttgctctg tcgccaggct ggagtgcagt   62940
```

```
ggcacaatct cagctcacta caacctttgc ctcccgggtc caagcgattc ccctgcctca   63000
gcctcccaag tagctgggac tacaggcacg caccaccatg gcaagctaac ttttcttt    63060 tttttctt  tctttttttt ttgagatgaa gtctcgctct gtcacccagg ctggagtgca   63120
ttggtgcgat cttggctcac tgcaagctcc gcctcctggg ttcacgccat tctcctgcct   63180
cagcctcccg agtagctggg actacaggcg cccccaccac gcccggctaa ttttttttgtg  63240 tttttagtag agacggagtt tcaccgtgtt agccaggatg gtcttgatgt cctgacctcg   63300
tgatccgctt gctccggcct cccaaagtgc tgggattaca ggcgtgagcc accacgccta   63360
gcccccattt ttcaattgag ttgtttgttt taagacctct ttgtatatta ccacatgtgt   63420
attgaaaata ttttctccca gtctgtggct tgtctttaat tttcttagca atgtcttttg   63480
cagagcagaa ggtttcatta gctttcatag attccaactt atattttctc tttcatggat   63540
tgtgcatttg gtgttgccca cacagatttt tatactgtat tctggtgcca tttactgagt   63600
taacaattgc ggaagaactg gaagaaagga agcaaacaaa acgagttctg cgtggcactg   63660
tcagtgcggg ggcatgggga gtcctgcagg gtgaggtatg ggcggtatgg caaggcgcgg   63720
gcccatagat gtgcaggtct ggagatgtgt gcagcggaga tgtgcgggcc cgagatgtgc   63780
gggtccgatg tgtgggtccg gagatgtgcg cgtacccaga ggtgcagatc ggaaatgtgg   63840
gggtccggag gaaatgtgcg gatcaggaga agtgccagtc ccgagatgtg cggatcggag   63900
atgtggaggg ctaggagatg cgtgggtccg gagatgcgca gatcaggaga tgggcgaatc   63960
ggagatgcgc gggtccggaa atgtgcagag cggagatgtg tggatcagga gatgttgggg   64020
ggtcaggaga tgcgggggtc cagagatgtg ggggtccgga gatgtgcggg tctggagatg   64080
tgcagagcag agcaaagatg agctgatcgg agatgcccag gtccggggat ccacgggtcc   64140
ggagacgcgc gggtccggag atgcgtgggt ccagagatgt gcgggtccaa agatgtgcaa   64200
atctgaagat gtgtggatgg gagatgtgca ggtccggaga tgcgcggggc ggagatgtgt   64260
ggatcggaga tgctcagatc gaagatgtgg gaatgaggag atgtgcgggg cgggatgtgt   64320
ggatgggaga cgcgcgggcc cggagatatg cggggcggag atgtgcgggt ccagggatgt   64380
gtgatctgag gtgtgtgggt ccggagctcg gggtcagctc agcagcagtg agagcgagca   64440
tgctggcttt gggagcacag cacaatggca gctgtaggag tgcaagaggg tgtgacccag   64500
aggcagggcc cggccccgca tgggtgttct gaggtttatg cctcagcact agaagcctcg   64560
tatgcgaaat cacatcctca tagacccggt tcagacacag gatagtgatg cctggactat   64620
tcatccgtct ctcctctttt tccccagaca cgctttcacc agcttcgagc ccctcctcgg   64680
tgacttatcc tgtggtcccc ggcagcgtgg acgagtctcc cagtggagca ttgaacatcg   64740
aatgtagaat ctgcggggac aaggcctcag gctatcatta cggagtccac gcgtgtgaag   64800
gctgcaaggt agagggagc tggaacaggg cctggtggcc gccaccatca actacttatg    64860 gtcacttta tagcaaatgg cagtcattac tgagagattg cagaaagtcc cggataagaa    64920
actgacttca ggccaggcgc ggtatctcat gcctataatt ccagcacttt gggagaccga   64980
gatgggtgga tcacctgaga tcaggagttc gataccagcc tggccaacat gatgaaaccc   65040
tgtctctact aaaaatacca aaaaaaatta gccaggcgtg gtggtgggcg cctgtaagcc   65100
cagctactcg agaggcaaag acaggagaat tgcttgaacc caggagccag aggttgcagt   65160
gagccaagat tgcgccactg cactccagcc tgggcaacaa gagtgagact ccatcttaaa   65220 aaaaagaaa  gaaaaaaga  aaaagaaaaa gaaactgacc tcagtgatag attagcctct   65280
ctttatagca cagaacccct gagagcgtaa gccctgttgt gaactgcgta tttgaggaat   65340
```

```
ctagcttgta cgcccttat gagaatctaa tacttgatgt tccaaggtgg aacactttca    65400
tcctgaaact atccctcccc accccatct gtggaaaaat tgtcttccat gaaaccggtc    65460
cctggtggca aaaggttgg ggattgctgc tttagagagt ctaggacaaa tggttcctct    65520
gtgctttgta aatacttaga gaagtgcatt ctttaaaaga aaataagtca cattggaccg    65580
ggtgcagtgg ctcacgccta atctcagc actttgggag gccgaggcgg ctggatcacc     65640
tgaggtcagg agttcaagac cagcctggcc aacatggtga aaccctgtct ctactaaaaa    65700
tacaaaaatt agccaggtgt ggtggtgggt gcctgtaatc ccagctactt gggaggctga    65760
agcaggagaa ttgcttgaac tcaggaggcg gaggttgcag tgagctgaga tcgagccatt    65820
tcactccagc ctaggcgaca agagtaaaac ttcatctcaa aaaaaaaaa aagagagaaa    65880 agaaaataag ccacattaag aacatcactt cattcgaata caagacagag agctgttacc    65940
gttgatctct ggagcctccc tgaaggccag gtgggcagg tgttctcatg ctcctgccag     66000
ggaaattggc catcagagac acagagtatc ttgcttaggg tcccacagcc cccagcagca    66060
gggactggaa ccagagactg gctgctcctg ctccccagca gttccttcct gcacatcagg    66120
ggcttctcca cctgattcaa cgacaggaa cccctgtgc atcttcatcc tcctgctggc       66180
tcagcctgcc ctaaacagat gtgacctggg ccaggagtgc atgaaggcag gccctgttgt    66240
cctgcatgct gccagctgga ctggtggccc ttccgtgttt gtcagcgtgg tgatgaggag   66300
agctcctgta gcagcgtccc tttagggttg cacagacgtg ctcaagtctg cgccttatg    66360 tacgtgatat gtgggagatc atcatctgaa tgtttggttt gaatcagaaa tcccttctca    66420
cggtgcacgc tgcaggtgtt cactaacttg gaaaatgcca ccgcctttct ggcacaatgt    66480
accatcttgg aacaccagca ttctgccctg agccaggcct ggcctcagag gcctgggcca    66540
cagggagaac ctcacagcca ggacactgtg gcactctgct gtctagaagc ctgtctcccc    66600
acccttccca ttctaacccc atgcgttcct cagcctcccc actgtgcaag cctaggtaag    66660
gacattatga agacgtcagc ctgcctctca cattccctg cacactgctg tccctctccc      66720
gcgggccaag cagacccact gtggcaaaaa tatagaagaa tgacttaaaa gcaaagagaa    66780
aaaagaaccc aaagcaaaaa tgaactcctt cgcatgtttt ctaaccatat cctttgaaa     66840 aagctcctta taaagtggcc ttttccttag ggccatgatt aattattcat ttagttttgt    66900
tttttatgga ctatttagta acattgtttc ttgctgggta gagtttaaga tgcttttaca    66960
aagcaagaaa attgtttaca aacagctggc ttccttttat tataattttt gtctttgagg    67020
gagttaatat actcttacaa aaattcttag aaagtcttta gtcacaaata tggaaatgtc    67080
acaatgctgg ggatagttac attcatatac attgtaacaa ggctgagtaa ctctttggaa    67140
aactataatt gtgttttccc aagtcagatg agggcatttt gaaatgactt cgaatgctgc    67200 ctcatttat tgttttcac attaaatgta acgacattta aagttctgta tttgtcctaa       67260
tcattccaga cttcttagaa gaactatttc tttctttttt ttttttttt tttttttttt     67320 tttgagatgg agtctcactc tgtcgcgcag gctggagtgc agtggcacaa tctcagctca    67380
ctgcaacctc cgcctcctgg gttcaagtga ttgtcctacc tcagcctcct gagtagctgg    67440
gactacagac ttacatcacc atgcccggct aattttgta ttttagtag agacagggt        67500 gcaccatgtt ggctaggctg gtctcgaact cctgacctca ggtgatccac ccgcctcagc    67560
ctcctaaagt gctgggatta caggcatgat caccatgcct ggcctggaat aacttttctc    67620
taaattttgt tcatttaaaa agaaacaata aatgagcaac aaaaaaggtg agtaaagcaa    67680
```

```
gtgcgctggt ttctcagtgg cccaggtctt taaatccact gtgtattacc ctcacagggc    67740
ttctttcggc gaacgattcg actcaagctg gtgtatgaca agtgcgaccg cagctgcaag    67800
atccagaaaa agaacagaaa caaatgccag tattgtcgat ttcacaagtg cctttctgtc    67860
gggatgtcac acaacggtag gtaaggtggc cctgcacatt ttcccagttc gttcctcagt    67920
tccccttcct tgctccaagg gaacagatca agctatggat gaatgtgctt caacatttca    67980
cacccaagtc attttgtaat cagagtggcc taagaaaata aaagtcgccc aggcgcggtg    68040
gttcacgcct gtaatcccag cactttggga ggctgaggtg ggtggatcac ctcaggtcag    68100
gagtttgaga ccagcctggc caatatggtg aaaccccgtc tctactaaga atgcaaaaat    68160
tagctgggtg tggtggcaca tgcctgtagt cccagctact cgggaggctg aggcagaaga    68220
atcgcttgaa cccgggaggc ggaggttgca gtgagctgag attgcgccac tgcactccag    68280
cctgggcgac agagggagat tccgtctcac aaaaaaaaaa aaagaaaaa gaaagaaaga    68340 aagaaaataa aagtctccca ggtgcggtgg ttcacacctg taatcccagc actttggagg    68400
ccgaggcggg tggatcactt gaggtcagga gtttgagacc agcctggcga acatggcaaa    68460
accccgtctc taataaaaat acaaaaatta gctgggcatg gtagtgcaca cctgtaatcc    68520
cagctacttg ggaggatgag acaggagaat agcttgaacc cgggaggcgg aggttgcagt    68580
gagctgagat cgcaccactg cactccagcc tgggcgacag agtgcgactc cgtctcaaaa    68640 aaaagaaaa aaaagaaaa agtctcaaat agctgagatt cagtggtgca ttggactcgc    68700
tgttagaaac ttcagtggta agactttgat acagaatcga aaaccaagt ggaaggcacc    68760 aaaatgacag aatgttcacc tcgtccatag gaagggtgta ccacctcaaa catctcacca    68820
cgttatgaat ttccttctag ccaatcattt aatagtttca gaacatgcta attgtgatgt    68880
gaatgtaagt cgttcataag agttgcatgt ctaccttctg gaaaagaag cagttattat    68940 ataaactcat cccgaagccc cgttcacctc cttcactcaa aggttgatga tgcacctgat    69000
agtggtgtgc accctactaa tgagacgaac gatggtgtca ccttcagcct gcacctgtta    69060
acgatggtgt caccttcagc ctgcacctgt ttaaacatct acagtgtatg gagtttgagt    69120
ttttcatctc tccatagtgg aaagccgaat agtaatgaag gatgggtctg aactgcctgt    69180
gaattttcat tcctggttta agtcctgggg ggagcccctc gtccagccct gtccgcgcag    69240
tcatgacctc actgctcatg cctgtgtttc cccctccaaa ccctagcgat tcgttttgga    69300
cgaatgccaa gatctgagaa agcaaaactg aaagcagaaa ttcttacctg tgaacatgac    69360
atagaagatt ctgaaactgc agatctcaaa tctctggcca agagaatcta cgaggcctac    69420
ttgaagaact tcaacatgaa caaggtcaaa gcccgggtca tcctctcagg aaaggccagt    69480
aacaatccag taggtgtttg cggctgttct gggttctctt ggcaacatgg aaccagtgtc    69540
gtagaggacg attaaggaca catgtgttga atgttgagaa aattatattt atcccacagt    69600
taagcaaagg acagcgaaga tggaaacagt tcattctgag actctgagct gtagcttaac    69660
aacaactcct ttcttcttgc ttggagccac ctcaaagctc ttagcaacta agttattata    69720
ctggctatgt aattaataca cttaaaaaaa accttaatag cttaccaagt actaagatga    69780
tttcttagga gcattttttc ttaaatagag ataggtcttt gctctgttgc ccaggctgga    69840
atgcagtggt gcaatcatag ttcactgcag ccttgaactc ctgggctcaa gcaatcctcc    69900
tgcctcagcc tcccaaggag ctgggactac aggtgtgcac caccacacct ggctatgttt    69960
gatgttgttg ttgttttgtt ttgttttgt tttttggtag agatgagatg tttcccagcc    70020
tggtctcaaa ctcctggcct caagtgatct tcccacctcg gcctcccaaa gcactggcat    70080
```

```
tacaggtgtg agtcatggca cccagcatta actggattta aaaaaaaaaa aactgaccag   70140
gcaagatggg tcatgcctgt aatcctggca ctctggggag gccaaggtgg gcagattgct   70200
tgagtccagg agtttgatac cagcctggcc aacatggaga acccccaact ctactaaaga   70260
tacaaaaatt agctgagcag ggtggcacac acctgtaatt ccagctactt gggtggctta   70320
ggcatgagaa ttgcttcaac ccgggaggca gaggttacag caagctgaga tcatgccact   70380
gcactccagc ctgggtgaca gatcgagacc ctatctcaaa aaaaaatag aataataaaa   70440 taaatcccta ctttgaggtg tattagtctg ctataaagaa atccctgaga cctggtaatt   70500
tataaagaaa agaggtttaa ttggctcgtg gcccacaagg ctgtacagga agcttctgct   70560
tctggggagg cctcagggaa tttgactcat agcagaaggt gaagtgggag taggcgtctt   70620
gcatggcagg agcaaaaaca agagacacac acttttcacc catcagatct tgtgagaacg   70680
ctatcactag agtagcacca agaggatggt gctaaaccat tcatgaagga tcaccccat   70740 gatccagtcc ctcccgccag gcctcacctc caccactggg gattacagtt caccatgaga   70800
tttgggtggg gacacagagc caaaccatat cataaggcta gaaaaggaaa ccacttactt   70860
cccactcaaa atgtgctctt ggtcctttct cctaaaacta ctccctccct ctcagacaaa   70920
catgcctaca ttcttttttcc gccttcagtg aaaagacagt gacatcttgg ggcttagaaa   70980
gggccacttg taagccaggc gtggtggctc acgcctgtca tcccagcact ttgggaggcc   71040
aagacaggcg gatcacgagg tcaggagatc aagaccatcc tggctaacat ggtgaaacac   71100
catctccact aaaaatacaa aaaattagcc gggcgtggtg gcgggcgcct gtagtctcag   71160
ctacttggga agctgaggca ggagaatggc gtgaacccag gaggcagagc ttgcagtgag   71220
ccgagatcgt gccactgcac ttccagcctg ggcgacaaag ccagctgtgt ctgggcgcgg   71280
tggctcatgt ctgtaatccc agcactttgg gaggctgagg tgggtggatc acttgaggtc   71340
aggagtttga gaccaccctg gccaacatgg tgaaacccca tctctattaa aaatacaaaa   71400
aattagctgg gcatggtagc ggttgcctgt aatcccagct acttgggagg ctgaggcagg   71460
agaattgctt gaacctggga gctggaggtt gcagtgagct gagatcgcac cactgcactc   71520
cagcttgggc aacagagtga gactctgtct caaaaaaaaa agaaaggaa aagaaggac   71580 cacttgttat agaaagcctg tcttttaagg tagctctgga ccttttcaga ggcagccaaa   71640
ttgcccctca tggttcgtcc cccacatccc cgcctgcctg gctaagtcc tccttccccc   71700 tccccaacag ttaaataagt ctttgtctcc attacaaaac aaatctcaga gctaccttca   71760
aagaagagcc agccctcagt tggtgaatga agatactttg acatttttcct atgagcatgg   71820 tgaaacaggt ttaatttgta ttaaatagct tgaagcaatc cttattggga attacaaggt   71880
ggaattttag tcacaggaaa ataaagcatt tcacaagcta cttactttca tgaacaaacc   71940
aaacctcttc tttactgagt cctttaattc ttcagtgaat tctccaatta aataggccga   72000
gacattttag aagtttccag cagacaccca cactaggcag ctccagaggc ttgtcccaat   72060
tagaactttc ctgattacg agagtgaaag aaaaggtaac ttttagcttc gagtctctat   72120
cctggatatg attagtacag cccaaaattg ggatggctaa aacttttgtt tgccagctta   72180
tatttctccc ttggatttca gaattgaaag caggctgggc acagtggctc acactgtaat   72240
cccagcactt tgggaggctg aggcgggagg atcacttgag gcaatccaag agtttgagac   72300
caggcaacac aaggagacct cgtctctaca aaaaatgatt tttttaaaaaa ctagctgggc   72360 atggtggcat gtgcctgtgg tcccaggtac ttgggaagct gagatgggag gatggcttga   72420
```

```
gcccaggagt tcaaaaccaa cctgggcaac atggcaagac cacatctcta caaaaaataa    72480
aaacattatc caggcatggt ggcacatgcc tatagtcccc gcgacttggg aggttgagga    72540
ggatgccttg aggccaggag ttcaaggctg cagcgagcca cgatcgcgcc actgcactcc    72600
agcctaggcg acaaagcgag actctctaaa aaaaattcga agcagagtta agttgtcttt    72660
cttcctaaca acctgccccc accatggggt gcgaatggga ctcctggagt cctcctgcac    72720
ctccccttgg agaccaccaa gctctaggaa ccccatcacc ctcagctgag gtcacatgc     72780
agcaactagc aggcgggaat ctgtttgcat tttggcctta agaaataaa taataggcca     72840
ggcgcggtgg ctcatgcctg taatcccagc actttgggag gctgaggcag gtggatcacc    72900
tgaggtcagg agttggagac cagcctgacc aatatggtga aaccccgtct ctactaaaaa    72960
tacaaaaatt agctaggcat ggtcgtgggc acctgtaatc ccaactaccc aggaggctga    73020
ggcaggagaa ttgcttgaac ctggaaggca gaggttgcag tgagccgaga tcacaccact    73080
gcactccagc ctgggtgaca gagcgagact ccatctcaaa aaaaaaaaa aaagagggcc     73140
aggcgtggtt gctcatgctt atgcctgtaa tcccagcact gtgggaggca gaggagggcg    73200
gattacctga gctcaggagt tcgagaccag cctgggcaac atggtaaaac cccatctcta    73260
ctaaaataca aaaattagc cgggcatggc agtgtgcgcc tgtagtccca tctattcggg      73320
aggctgaggc aggagaatgg cgtgaacctg ggaggtggag gttgcaggga gccgagatca    73380
caccggtgca ctccagcctg ggtgacagag tgagactcca tctcaaaaaa aaaaaaaag     73440
aaagaaatga tagatgaata gtttaggatt ggggttcaca atttggtttt ctgtagaaaa    73500
agagaaccgg gcactcttcc gagagtcaga tgccctcttc cacccacacc cacaaagcca    73560
gagcaccgca ggtaccagtt ttcaaggcaa cctccaacca tcatgtgact ctttgtgttt    73620
gatcacactg tttgctccaa gccagggttg cgtcccaccc catgtccttg tctgcgcacg    73680
ggacgctgga ggcacggccc cctcctccct gcctagcctg ctgacgggct ttccagagct    73740
ggctccttca ggtgcaggat accctctctg cttagtctgg gaaaaggccc cgttggcagg    73800
atgcccacca ccaggccaca ctgcctgaat ctattggcag agctctggtt ttgtggccaa    73860
ggtgggtagt ggaagaccat agcctgtgtc ccttacacat ctcagaaagc aaccccatct    73920
gtgggcaaga aatctgttag ggagaccaag cagcggcctg gaaacaccctt gatctctgcc   73980
cagtggccca catgcggtcg ccgtttcatc agtttccagc ctgggtgacc tcacagcccc    74040
agccacgccc cacagagcct caggaaggca cactgacctc agggccggcg gctgacttca    74100
tttctgtttg gggatgagag gcggcacagt aaactgtcca ggccagtaaa ctaatggatt    74160
catacgaacc gtaatgaacg tgggctgtgt gctggggaag gcaggctcgc ctcctccctg    74220
caggggctgc tggggtgaaa gcaaccctga aatgttcaaa gccttgatgg ggaagcacgg    74280
gggatggata gattttaatt tcaaagcagc cctctggttt gctataagcg ggggactgaa    74340
tttctctttg cagtggccaa tgcctttctt ctgtcaagat cagctcgtgg ccttcagatc    74400
agatgacgca aagcccatg gctgagctgg aacaggctag aatgctgggg ggggcctga     74460
aaccggtggg ggagttgtgg gaggcctaga atcagccagg aggcttgggt cggggttgga    74520
accgccagt gtgcacggag gaggctgtgg ggcaggggg aggccgctgc atggagccgc      74580
atagatgcca ttgcttgagg aaaggtgggc tttagctgag ggaaggagtg aggggtggat    74640
ggagaatgtc tgtgtccatc tggacactgg gactgtttga gccctgaga tttcagaacc     74700
gtgggccaga aaatggtcag ggcccttggt gatgggaag gcgcctctg gggaactcac      74760
tgccccttga tttgagggta acagggatgg aagcagagtc agggggctga gggaggcaat    74820
```

```
aaaaatgggt gcttttcaac agtgtctaaa aacataagat gttgacctgt caggggttga   74880
gaatgtcgtc agaagacttt ggaggaagca acagaaaatg agactgaggg gcttgggcag   74940
agtcagtgcc ttctgtgtga tgcacgctca tgcacaaatg cacgcacata cccacactca   75000
cacatccgtg cacacacggg tacacacaca tacacgtgca cccacatgca tgctcacaca   75060
catgcaccca cagtcacaca tccatgcatg catgtgtaca caaacacacc cacacataca   75120
catgcaccca cacgtgtaca cagatgcacc tccaccccca tacatgcaca tggacacaca   75180
catgcaccca cacgcacaca agcatccatg ctcacatggg tacacactca cacatccatg   75240
catgcacgtg taaacacaca caccccacaa catacacgtg cacccacaca tgcacacaga   75300
cgcacctcca cccccacaca cgcacacaca cacatgcacc cacacatgga tacacgcaca   75360
ctcacacatg tacccacacc tgtgtgtaca cacacacatg catgctcaca cacatgcacc   75420
caggcacaca caaatccaca ttcacccata cagtcacaca catgcataca cacacataca   75480
aacacatgca ttcacacaga tgcatacaca cacacactta caaactacac atgtgcttat   75540
acatgctcac atgcatgtat atgcacacac ataccctcac cttatgcaca catgtaccca   75600
cacacgtacc cacacatata caagcatgca cacatatata tatatacaca tgctcacacg   75660
catacccaca ctcacatgtg tgcacatatg ctcacacaca cgtgcacaca catgctcaca   75720
cacacactta ctgttgctca ggcttagctg ctttgggctt aagaagcaaa ctgcaccttc   75780
caaaaaatga gtgtggtgtt cagttaaaca accaaataat tctttagcac tgaatatgtg   75840
gactttagaa attcaaacta taaggtgata ataacgttgt cctgctactt tttaatctaa   75900
caaacatatc agaactgaca ctcagttcaa atgaagaaag taggaattgg gcgtgccgtg   75960
ttattttttc aaagattctc ctattgctcc aaattgttgg ggattatctt aaagtctttg   76020
aatagcttca gttatggaag attttaccct ctgagaatag aactgaattt tagacaaacc   76080
atgagtccat tgtagctaga ctggcatgca agttgggatt aaacagagta aaacgtcttg   76140
tttaaaaaaa taagaaaggc cggcttgggc aacatagtga gacctcctct atgaaaagtt   76200
agctgggcat ggtggtgtgc gcctgtggtt ccagccgctc aggaggccga ggcaggagga   76260
tggaggtcaa gactgcagtg gactgtggtt gcgccactgt actccagcct gggtgacaca   76320
gcaagacccc gtctcaaaaa agaaaacag aaaaaagaaa aaaaaagttg agcaaggaga   76380
ctaatttgtg acatgcagct gaacatggtt tttaagacca gttttgaaag aggaattcca   76440
acattattct taacatttca gaagcctggg cataagggtg acctccaggg tgccgtgtta   76500
taacaggact gctcctttca acagctatga ccttatacca tgtcttgggg tgttgcctgc   76560
cgtgtgacag tccaatatta tacctactac ttaagttttc tttagattaa aaaatgtgct   76620 tcatattta tgccatttct acaaatgtat agtaaaacat aaccaagaga gcttattaaa   76680
taatttcatc caaagcagtt ctaccagtgc ttcacattta ttttttattt atttatttat   76740
ttttgagact gagtctcact ctcttgccca ggctggagtg cagtggcgca atctcagctc   76800
actgcaacct cccccctcctg ggttcaagcg attctcctgc ctcagcctcc taagtagctg   76860
ggattacagg tgccagccac cacacccgac taattttgt attttagta gacacgggct   76920 tttgccatgt tggccgggct ggtctcgaaa tcctgacctc aggtcatcca cctaccttgg   76980
cctcccaaag tgctggcatt gcgggcatga gctactgcgc ctggtccaca tttaatttt   77040 tgcaaaaaga tgcagctgc taacagagat gaattctcat gagtgatatc attgagcttc   77100
gtaggccaca tgagtgtgtg ccgggaccag tgtggcagca agcggggcgt tctgctctcg   77160
```

```
gcatggagtg attggggaaa atctaggcag cttcctgcct cacgctgttt aaaacccttta    77220 taatgtgctt tatttcattt atttgaaatg actgcctgtc gtgtcagata tattcatagt    77280
caagcttgag tataaaaggc atattccaaa gttaaatata agctgctgca tagattttt     77340 tgtaaaatga tctcaccaag aatgtttatc cataaagttt agcgaatttg caagtgtgtt    77400
tttcaacagc atttctcttt agctttaata aacattggtt tcttcatggt accactcatt    77460
ttgaattcag tggtctccag ttctccctgc taaatgaggc ccactttcta aaaccaaagt    77520 gataattta taaaaatgaa atgagatatt tgttaccaca gaagtcctca tttacgagag     77580
tacatcccca tagaactagt ccacggtgag cctcaggggc atgcaagctg tttaacgatg    77640
cccccagcct agaaaggccc aggcttgggt gttcatgctc cgctgttgcc ttcttgaaat    77700
tcataatcat ctttgaacaa ggggtcccgc agtgtgtggt ggctcacgcc tgtaatccca    77760
acactctggg aggctgaagc gggtggatca cctgaggtcg ggagtttgag accagcctga    77820
ccaacatggt gaaaccccat ctctactaaa aatacagaaa ttaaccaggc gtggttggtg    77880
ggtgcctgta atcccagcta ctcaggaggc tgaggcagga gaatcactca aacctgggag    77940
gtggaggttg cagtgagtcg agatcacgcc actgcactcc agcctgggca acagagcgag    78000
actccgtctc aaaaagaaa aaccaagggg tcccacattt gcattttgc tctgggtcct     78060 gtaaattacg tagccaggcc tgcatttgtc ctgggagatg ctctaccaaa aaacaataaa    78120
taacaccaag cattctgtaa tcaaacactg taggaacccc tgcttatcct agcctcattc    78180
tcattctgga agactgcaca tttatcatgt taaagactca gctagggagg cccaacttca    78240
ttcaactcag tgtttcttat ttttttaaaa cagaactcat ttttaaaaa aattattggc     78300 tgggcgtggt ggctcacgcc tgtaatccca gcactttggg aggctgaggt gggcggatca    78360
cgaggtcagg agatcgagac catcctggct aacacggtga accccgtct ctactaaaaa     78420 tacaaaaaaa aatgagctgg gcatggtggc gggcgcctgt agtcccagct actggggagg    78480
ctgaggcagg agaatggcat gaacccggga ggcggagctt gctgtgagcc aagatcacgc    78540
cactgcactc cagcctgggc aacagagcga gactccatct caaaaaaaaa aaaaaattat    78600
ttaacacctt tatttctgct gaatgtactt tagaaagatt gagtgatttg aataaagtga    78660
cggtggccta agagtctatt ttctggaatt gagggaatac tgccatcgat ccttgaaaaa    78720
tatttattta gttcctccta gaggccgggc acagtggctc acgcatgtaa tcctggcctg    78780
cactttggaa ggctgaggtg gacagattgc ctgagctcag gagttcaaga ccagcctggg    78840
taacaaggtg aaacccgtct ctactaaaat acaaaaaatt agctgggcgt ggtgatgtgt    78900
gcttgtaatc ccagctactc gggaggctga ggcaggagaa ttgcttgaac tcaggaggcg    78960
gaggcagagg ttgcaatgag ctgggattgc accactgcac tccagcctgg gcaacagagc    79020
aagactctgt ctcaaaaaa aaaaaaaatt atctagcccc tcctagaaat gttaattcct     79080
taaatctgag cttcagcttt ctgtgaagca gaattatctc caaactttaa caaacaatgg    79140
tcagaactgt ttttaaggtc ttggagagag atcattttca gtctttatta atcggacttg    79200
agattattta gaaacttggc tctgaatatt gtattcagaa tgttttcact catttgtgag    79260
taatttttta aatatcccct ttcctcagat gcagaatcag ggcttttgt ccagcattat     79320 gttgcaagtc ctggttctgt tgaaacattc cataccatct gtgtgatggt tatcggcacc    79380
tccaccggtg ccctgaagac agttttgtgc tgtgagtcca gaaacaggaa acacttcagg    79440
ctgtgtgtca gaagcattgt cagtggttgt gttttgccca ctggcagggg gcattcttta    79500
aatcctggga tgcttctgcg ctttgggctc cactgttcca gcagtgatta gaaataacgc    79560
```

```
tgtaggccgg gcgcggtggc tcacccctgt aatcccagca ctttgggagg ctgaggtggg    79620
cagattacct gaggtcagga gtgcgacacc agcctgacca acatggtgta accccgtctc    79680
tactaaaaat acaaaattag ctgggcgtgg tggcgcatgc ctgtaatccc agctactcag    79740
aaggctgagg cgggagaatc gcttgaacct gggaggccga ggttgcagtg agccgagatt    79800
gtgccattgc actccagcct gggcaacaag agcaaaactc tgtctcaaaa aaaaagaaa     79860 taacaccttag ccccactgca ttattgacct gtgtctgcat gagctgtgga ccacattata    79920
atcagagaga tctctcagat gttgtcactt tcctgctcta cccgcagatg taaatttcag    79980
ccaacagcag tgtttgtgct cattttcccc ggctctccca cacatgtaat cccttctgag    80040
catgttggct tcaaataata tggccagcca cctcttccac cacgagatct tcaggaaatg    80100
gcaggccact gggtttacat gcagatggca tgggagcaca caaggcacgg ctgtggggag    80160
ttggcacttg ctccagaata tggagcaccg agtgaaggtt tcagtttcct gcactgagag    80220
aaacaagggc attccgaggc ttttccactt tatccctaaa gagtttcaca acgcttgttt    80280
gccgatttct acatagatgc cacctttctg agttgtatgt atttacatgc caaatgtatt    80340
cattgagcag cgttaaataa tggtgttcac ccctaaagtg catatactgg taaaattaag    80400
aatgatcgta attaagcctc ttgcaatagt cattagttca gagaatattt aagaatatta    80460
aaggtgcttt gctaatgtcc tcgttagttt tgttttgaca aaatcagtac ttcagtttct    80520
tgtttctttt ttttttgaga cggagtctta ctctcgctct gtcgcccaga ctggagactg    80580
gagtgcagtg gcacgatctt ggctcactgc aacgtccacc tcccaggttc aagcgattct    80640
cctgcctcag cctcccgagt agctggggtt acaggcacac actatgcctg gctaattttt    80700 ttttttttt tgagacggag tctcgctctg tcacccaggc tggagtgcag tggcgcaatg    80760
tcggctcact gcaagctctg cctcctgggt tcacgccatt ctcctgcctc agcctcccga    80820
gtagctggga ctacaggcgc ccgccaccac acccagctaa ttttttttgta tttttagtag    80880 agacggggtt tcaccatgct ggccaggctg gtctcgaact cttgacctca ggtaaaccac    80940
ccacctcagc ctcccaaagt tctgggatta caggcgtgag ccaccatgcc cagcccagta    81000
cttcagtttc ttagcgatga aatccaccca atgtcaggcg atgactatta ttatttact    81060 gatttatact gtttgttctc tattaatgtc ttattttccc caaccgattt tgaagttgag    81120
taaggactat gttccgcggg tatcttgagt cctctgaggc actgagcttg gtgatttgga    81180
cgcaggagct gctcattagt gagctgatag ctgggagcat agcgcatccc acatcacctg    81240
acttaccttg gtgtcctcct ttgtagcctt ttgtcataca tgatatggag acactgtgta    81300
tggctgagaa gacgctggtg gccaagctgg tggccaatgg catccagaac aaggaggcgg    81360
aggtccgcat ctttcactgc tgccagtgca cgtcagtgga gaccgtcacg gagctcacgg    81420
aattcgccaa ggccatccca ggcttcgcaa acttggacct gaacgatcaa gtgacattgc    81480
taaaatacgg agtttatgag gccatattcg ccatgctgtc ttctgtgatg aacaaagacg    81540
ggatgctggt agcgtatgga aatgggttta taactcgtga attcctaaaa agcctaagga    81600
aaccgttctg tgatatcatg gaacccaagt ttgattttgc catgaagttc aatgcactgg    81660
aactggatga cagtgatatc tccctttttg tggctgctat catttgctgt ggaggtgagt    81720
ggttgattta atctgctggt atcatgtcac tgacaggctc ctgtcttgaa aaatttgaca    81780
atgggaaatc cagtaccagc ctgagctgtt ccagtgagg ggacactcac atggtgggaa    81840
gacgtctgac ccccagtcac tgctgagaat tcagtgggaa ttataacaat attgtataat    81900
```

```
attatagtat atattgttat tatctataaa tacatattta atattatgta aatgtatgac   81960
attttaatca taatattagc caggtgtggg ggtgcacacc tttagtccca gctacttact   82020
cagtagactg aggcaaaagg atctcttgag cccaggagtt caggttgcaa tgagttatga   82080
atgcaccact gcactctagc ctgggcaaca gaacaagacc tatttcttta aaaaaaaatt   82140
atatattttg cacaaatata tatatagaga aaaagaggtc ggacatgggc ctgtaatccc   82200
agcccttggg gaggctgagg tgggtggatc acttgagccc aggaggttga gaccagcctg   82260
ggcaacatgg caagacccc g tctctacaaa aaaaaaaata gaaaaaatta gtcaagtatg   82320
gtggcatgta cctgtagtcc cagctacttg agaggctgag gtgggaggat cacttaagcc   82380
caggagacaa aggttgcagt gagccaaggt cacgccacca cactccagcc tgggcgacga   82440
agaatgaccc tgtctcaaaa aaaaaaaaaa aaaaattat acacacacac acacacacac   82500
atttcgttta tattatatct aatattataa acagatataa tttatatatt atgatattcc   82560
tgtatatatt ataatgat gttgtattca tattatagac aatattgtat gaagtgctat   82620
acagatgtca gtatagttgc tgtcacagtt ggttatgttg atgaaaagta tatttcctaa   82680
tgcaaaatat aatatcagtc agcagccaag tggcagtgac tgcaaggttt gctttgcccg   82740
aggaagcaga tcccagggaa ggccgatctg gtcctctctg tggaagctgg ctctgcagcc   82800
tccacatttt tggctcggtg tcacgttcct ttaaatagcc ccatctcagg tctaggaagg   82860
tcatccacct actgcaaact cggctgacct tacccagggt tggtggagac agatgggtc    82920 tcccacactg cctgcagcca tactgcgcct gggggattga ctcactgtca gcatggagct   82980
gactcagccc taccagccgt gcccgttact gtgtggctgg gcacaagtca gatgaaggaa   83040
gtccttgcgc tctggcataa agtgtacaaa gacaaagcag ttatgcataa tttgtccttt   83100
agtatggtca ggatgtagca ttgtgggtaa aatgcagttg cagaactatt tatatgtagc   83160
atgatcacag ttttataaag gaaattataa tcctatatca atcctatgta tatagaaaaa   83220
tgtccagtga gatatatgtt aaacctatta tggtgggatt aaaattatga ggggggattt   83280 ctattttca aaagattcct cctttttttt ttttttgaga cagagtctcc gtctgtcacc    83340
ctggctggag tgcagtggca cgatctcagg tcactgcaac ttccgcctcc tgggttcaag   83400
tgattcgcct gcctcagcct cctgagtagc tgagattaca ggaacatgcc agcacacctg   83460
gctaattttt gtatttttag taaagatggg gtttcaccat attggccagg ctggtctcaa   83520
actcctgacc ccgggtgacc cacccacctc ggcctcccaa agtgctggga ttacaggcat   83580
gagccactgc acccggcaat aattcctctc tttagagact taatagttat agccccagcc   83640
actctggagg ccgaggcagg aggattgctt gagcctagga gttccagtcc agcctaagca   83700
acagagcaag acccccatcac taaaacaata caaaaacaag aattttagaa ataaaaactt   83760
aataattaca tttacaacca aaaacaatga agatgtttaa atcctcatca ctagcaaccc   83820
tgttaagaat catagtaatg actgggtctg taagggagca ccgcctgctg aacatggctc   83880
agggcagtat tttctggacc aagaatcagg tctcatgctt tgagactgtc ccaggatgtc   83940
tagtgccagc taccccaggc aggtcatctg gtgtgaatgt tgactcttcc tgcaccaagt   84000
ctcagacctg ccccacccct ctccccactc tgggtctcct gatcttggct cactgcaatc   84060
tccgtctccc aggttcaagc gattctccca cctcagcctc ccgagtatct gggattacag   84120
gcgtgagcca ccgtgcctgg cctacaaaac ctagttctaa cacaatcact ccttaaatat   84180
ggtggaacac ttgaagcttg atatctagtt tggattcaaa agcttcattt cccatattat   84240
gcaaaactgg tggttgtgat ctccagaatg tactgttcct cctactagct ctaattttc    84300
```

```
tccctgacag gtggtcatca ggtaaatcac aagtgaaaag gccgcaccat aaggtgtact   84360
tagggcacta ttgccgccta gtagtatgaa tatttaggaa agagtactgg tcctgtctgt   84420
ccctacttca cctattgact ttggaaaaac ctatgtctat cttccagtca agttgacaat   84480
atctaaaggc agctcagttt ttttctaaga aaggccacat aaaataggca tgtttggttc   84540
ctgaaactga taagcagttc ttgggtgatt atcacactca aacctctctc tcttctttcg   84600
agactagatc gtcctggcct tctaaacgta ggacacattg aaaaaatgca ggagggtatt   84660
gtacatgtgc tcagactcca cctgcagagc aaccacccgg acgatatctt tctcttccca   84720
aaacttcttc aaaaaatggc agacctccgg cagctggtga cggagcatgc gcagctggtg   84780
cagatcatca agaagacgga gtcggatgct gcgctgcacc cgctactgca ggagatctac   84840
agggacatgt actgagttcc ttcagatcag ccacaccttt tccaggagtt ctgaagctga   84900
cagcactaca aaggagacgg gggagcagca cgattttgca caaatatcca ccactttaac   84960
cttagagctt ggacagtctg agctgtaggt aaccggcata ttattccata tctttgtttt   85020
aaccagtact tctaagagca tagaactcaa atgctggggg taggtggcta atctcaggac   85080
tgggaagatt acgcgaatt atgctcaatg gtctgatttt aactcacccg atgttaatca   85140
atgcacattg ctttagatca cattcgtgat ttaccattta attaactggt aacctcaaaa   85200
ttcgtggcct gtcttcccat tcaccccgct tttgactatt gtgctccttt ataattctga   85260
aaactaatca gcactttta acaatgttta taatcctata agtctagatg tatccaaagg   85320
tgaagtatgt aaaaagcagc aaaatattta tttcaaagac ttcacttctg tttcctgaat   85380
ctaaagaaag acaacatgct gctttttaat cataggatgg agaattttaa agaactgttt   85440
gggccaggca cagtcgctca tacttgtaat cccagcactt tgggaggccg aggcgggtgg   85500
atcacaaggt cagcagatcg agaccatcct ggccaacatg gtgaaaccct gtctctacta   85560
aaaatacaaa aattagccgg gtgtggtggc acatgcctgt aatcccagct actcgggaag   85620
ctgaggcagg agaattgctt gaaccaggga gttggaggtt gcagtgagct aagactgcac   85680
cactgcactc cagcctggtg acagaacgag actctgtctt aaaacaaac aaacaaaaaa   85740 aaaatctgtt agataagcta tcaaaatgca gctgttgttt tgttttggc tcactgtttt   85800 cgtggttgta actaatatgt ggaaaggccc atttccaggt ttgcgtagaa gagcccagaa   85860
aacagagtct caagaccccc gctctggact gtcataagct agcacccgtg gtaagcggga   85920
cgagacaagc tcccgaagcc cgccagcttc ctgctccact cagctccgtc cagtcaacct   85980
gaacccaccc agtccagctg tctgtgggaa tggtggtgtt cttagggaca gactgacacc   86040
ttacttgtca gtgttcctcc gggcccatt tggcagctcc cgtatctttt gttatgttgc   86100
ttttaaagat atgatgtttt attgttttaa ctcttggtga cagtagatgc tctctggagc   86160
gcagacgagg cacatgtgtc ttcatagcct gggctgggtg ggagccagtc accctgcgga   86220
tcgagagagg gggtagagtc ttcttcaaat ggcagtttta cttcaaatgg cagatttcac   86280
aagagttggt tattttttac aatggtttag gttgttaagt ctcctttgta tgtaaggtag   86340
ttttttcaac atctaaaatt tttgttttag ccttcaaaac caacttacca acctcagtcc   86400
agctgggaag gcagcgttga ttatggtagt ttgtcaagaa tatatggacc tggaaacact   86460
ttctctctct gtccacctgg tagataaatt gtcctgttga gaattttag atctggactg   86520 gaactgccag gaccaccgcc tccagggagt cgctgggcac ctggaggtat cgtcgatgcc   86580
tctcccccat ctttagaaaa tttggctctt ctgaggtcat tattatttta agaatgatta   86640
```

```
ggattgataa gggtcccatg accagcatta tgaaaatgcg agagtgggaa ggacacagtg    86700
tgagacttcc actagaaaaa agtgaaagtt agggttagga catccttttt taaaaattac    86760
aaatttagtc cgttttggtt tttgtaatca ggctaggcac agtggctcac acatggaatc    86820
ccagcacttt gggaggccga ggtgggagga tcacttgagc ccaggagttc gagaccagcc    86880
taggcaacat agcaagaccc tgtctgtaca caaaatttaa aaattagttc atcggggtgg    86940
cacacatcag tagtcccagc tactctgcag gctgaggtgg gaggattgct tgaacccagg    87000
aggtcgaggc tgcagtgagc tgtgatctca ccactgcatt ccagcctggg tgacagagtt    87060
agattccacc ctctcccacc ccggcaaaaa aaaaaaaaa agatgcaatc aaaggggctg    87120
ttggccagca atggcagcag cagcggcggg cagtctgccc aagtgtctta ggaaccaaaa    87180
gcaaataaaa gtgttttccat atatgccacc agccaagtgg ccatcctaat tcagaaagaa    87240
gctagccttt gagtgtctgt catggtgcat ccgtttcagt attatttcct aaaatgagaa    87300
gcccctgtgt caacaagatc caggggctgg agcccaatgc caagcctgtg ttgtccccag    87360
cgaccctgca gctgctcgct ctgatgtacc ctgtgccatt caaggagatg tggtccagga    87420
aagtgagcct catggttttc agagaagtca ttgttctgtt tacattttca taaaacctgt    87480
ttaaaatagc tccccgtctc aggctttcag cagtaacagt gagctgactg gcaagttcga    87540
tgttagctcc cgggacactc agcagcgatg gtgagcattt tggtttcctt aaggcccagc    87600
aagacttcca gggacatctc tggtgaagcc agaatggaga cacccgtgac ctcaggctga    87660
aagtcactcg acattggtct cttgtgttga tagggaagga aatcaggcat tcctatttct    87720
ttaaataaca aaaccactaa ttgccactca atgctggaat atttttgggtc acctaatcat    87780 agatttctca gggcatcaat actcaaatat aggctgatta tgccccagtt caaatgggaa    87840
ctattaacag agtgcatttc ttgccttgctg ggtttcaaca gacatcagcc aaaagaacaa    87900
aagagatgtc aggacagatt ccaggagtgt cggagcacat gtgtggcacc cgctccctct    87960
ggcagcgaat gtaggaagtc gccaaattta cccactcttc aacaagtcat tgtttaaaca    88020 cggttttca ttttctcaac ttttaatagc aaaaagtgcc aaagtcctca gagacctaac    88080
agccttggtc taccgtgctg accagggtga aggcacggcg agggactcct cccagacgtg    88140
cctcttgtgt gccagctggc tgtggctcgg gagcagacgc aggcctctcc attgtccagg    88200
ggagcctggc ggcgcatccc tcctctccca cctcctggca cttccagctg ggtgtcccac    88260
atgttggatt ccgtccccac cacacttcca gagaccggag aactgtgcag ggcctaaggc    88320
cgtttggatg aattgtcaaa acaagatgct tccagttaca gcggcaggag cgggactggg    88380
agcacgggct gacggctgct ggtgcctttc ttcccacctc gcttgcctgt ttccgcttga    88440
cccttcctcc agctccgatg agaagagtat aaagcatctt cctaacgggt gtgtttgcta    88500
tacgaacata atggacgtga agtggggcag aaacccagaa ctcagcattc aaggatgccc    88560
aggagagctg tccctgtttt aaagagctgt gttttgtttt gtttcgcatt tagagagcag    88620
acaaggcacc cttctgctgc gctgatacgt ttcttacact gggccatttt agaccccag    88680 ggaaacagcc ttcctggagc gttgtctgga ggttccaggg acagggcagc ctcccagagc    88740
cgagcaagag ctcaaggtac aaatgagaga tttgctatac cgtgagaagt caacaactta    88800
gccaccactt ccccgcaatg gaccatgtaa caaatacctc agcaggccct gcaaaaggcc    88860
atgctagagc tgaggcgcac agcctgtggc ctctgtagtt agggcaggtg ggatggagac    88920
tccttgagtg cacacacctg agcctgccca cacacagggg agcagcatct cgtatgcagt    88980
ctggaaggaa cttcggttgt gtaaagggag ccttgaagat acgtgcaaaa ggtgctaccc    89040
```

```
caatttggtg aaactgacat tgggcacgtc ttgggcttag gagaagcggc cgatggtccc    89100
ggcctgcagt gacaaacccc cctccccgca ccgcccccag cacccctct cctcttcacc    89160 tcttcctgct ggccacgagg aagccacttc ctcagagaga ccctaccaga tgcggatgga    89220
aacagatgca ccaaagcaag ccctgatgaa accgcgactt cctaaggtct gtctcctctg    89280
aacttgcacc tgggcctctc tgtgtttggt tccaagcact tcccacctca aactcccatt    89340
ttcaaaccac tgtatctctg cgcacatctg ctacttacca gccgcataca tgatggaggg    89400
ttttttggtc ctgatccagt ggccacacct gtctttgaaa tgtctcactg aactccagtt    89460
ttaaaataga ttcattgctt caacacagca agcccaatgc acccagctaa gactggcttg    89520
accgacagcc tggcctttgg tgggggctt cctggggcct ggggaaagct ggccaccttc    89580
aacagctggt acctcttcaa cagtgtggcc tttcaaaatg cagatgccac caggagaaca    89640
tgcccacagc tcaccaccta tggatgccat ggctctgggc agctttcaaa gcaggttcct    89700
gtggtctcct cagctgtttg aggggtaac agcaaatcag cctccatttt aaaatgaaaa    89760
caccagcctc cagatgtagg gcctgctggg tgttgctagc cgctggtccc caggcacggt    89820
gcactttctc cacctcctgc agcctccctg ttgtttctag actcttgcac ctggtgagtg    89880
caaggatagg tgacccaggg gcctgcagcc ttgtcctcag ctcccatctc ctggactgcc    89940
agcctcaccc tctgcagtta gcatggttgg cctgatgcag ggatcccgag ggattacttt    90000
ttagaccttc tttcacattc agaaaagtag tatagattca ggagaggcaa gaaaattatg    90060
ctgtccatag aagtcaccca tgaagactga tgccaccacc tgaaggctca tgattgttaa    90120
aaatgtccac gggaacctct cgtccacagg aggtttgtct caacacttcc cattttacg    90180 gcattggcat tgccaagcat ggggaagtat ctgctcttct catgttaaaa gtggcccagc    90240
ttttcttaac tcagtccaag ctgacttgtt tagctgcact ggaatttctt accaaccaaa    90300
tatttgcatc gagcaaaggg ggctgtgtgc acctccctaa tggcagcgat gatggctgct    90360
gtcattcaag cccatcttca gacgtcacag tctggaagtg aaatgtccac aaacatctgt    90420
ggcagaaaag gctatacgga ccacccagtt gtgctgcagc tttacagagc aaggaagggt    90480
tgtggcaaat aaatgattaa cctgcctcga ctgtgctgag ggcaacaaag gccatctcac    90540
caaaggatta ttcgatgcca ttaaatcatc ccgtgacctt cctgcttccg agtccatggc    90600
ctttgcccag ggcatgtact ccctgagag gccttctgcc tagaaagatc tatgactggg    90660
ttccaaagtt gaggcctagg ttttgctgg gatttagata ttttcaggca ccatttgac    90720 agcattcagg aaaacggtta ttgaccccat agactagggt aagaataaag gcaataaatt    90780
tggtctgact cagaatatag gagatccata tatttctctg gaaaccacag tgtacactaa    90840
aatgtgaaat tgaaggtttt gttaaaaaga aaaagataat gagcttcatg ctttgtttaa    90900
ttacataatg atttccatta cgctatttct gtgaaatgca gcaggttctt aaacgttatt    90960
tcagtggcat gggctggaag cttatcacaa aaagccatgt gtgtggcctt atcagaacag    91020
aaagagacag gctggtgccc aaggctgctg cctgctccac cttttgccag ctctggacat    91080
ctgaggacgt cccggcagat ctggaatggg gccctcaact gaccatttgc ttctcagaat    91140
ttcagtttga gacatgagag gtataatcag ttacttttct ccccccagag aaaccctttt    91200
gtgaggggag aggagctatg gtatgtggtt cagctgaaac acatacaact gcatcctttt    91260
ggagtccttt gccaacaaaa acagaccaac agaccagatg gtgtccatgt tcaatatcat    91320
gtcttgatgg acgcagctga tgacctcaaa tacttgagtg gtctcatggc tgttagatgg    91380
```
attatttgaa aaaaaaaaaa aaaaaagaga gaaaaaataa ttgattttta catcagagat 91440
agcaaactaa gacctgggga gggggtcag ctttttatttt attttatttt ttttaagttt 91500
gctagttggg tcaaatgtga ggaggaggga gtctacctgc cacctcttct cttgcccctc 91560
ttctgcccac acatccagca tccaaaatcc attcatttaa tgaattgata agtgccgtg 91620 caaactggtg cacaaacagg cccccagtcc acgcagcctg gctcctagga aaagtggtga 91680
ccgggcgtgg gggggcatgc cgcagccctg ggacacagtc gggcaccttc cccggacccc 91740
caggccttgg ctgtgcctca agtcagagag ggtcagcctt caggccccgg agacgagtga 91800
ctggccgatc atttcacaat aaaatcactc acttttggca acttcacttt ttttaaggca 91860
cagtcagttc ctttttctcat gtacctcaca aaagatgaag accatgtagt actctttttg 91920
gtaaagttac agtgttcatg ttaaatatca ctttttttcta cattgtgtgg taaaagaac 91980 tacgttaata gctatatctt aaatactgtg atttgacttt ttgaaaaata tcctaataca 92040
aatattttac taacttacaa tcactcattt aataagaaac atttggattc ttttgaaatc 92100
agtgttaatt gactcatatt cttaaaagcc tggctcttga ccctattgga aacacaaagg 92160
aagctgaaat caaacatcta aaatacactg cgtacacgtg tgcgtgcaca cacacacaca 92220
cacacacaca cacacagctc ttcatttctc ctgagccatg cagaatttac tttcaatgtg 92280
gaaatctgtt cccttaccca cactgtatat gcacagagca caagagaggc tatctctagt 92340
cacttccacc agcgaggcct tagactccgt attagaggcc accgatttca tacaacagtg 92400
tttcgctaaa gaccctttac tattcttgtt tagtaaatag ctgtctgctc ttcagggaac 92460
tgttacctat gggttattac caagaacgc tggcaattgg aaatgtcctg atggaaattc 92520
tttgcacgtg ccggttctct ggcatcctcc aggtggccca acccaaagca gaaagcagaa 92580
accacagacc ccgtgagtct ccccatacct tgtttccaat aacttggcaa aacttcttgg 92640
tgcatattgg ttacaccctc tgggattcat aatgccatta ggctaaaacc ctaagagaga 92700
gggttgacag aaacacacgc gagaatgagg cagatcccag agcaaggact gggcccagac 92760
tctccacatg tgctctacta gtgagtgcct tatactctca gtattttggg gcttacagct 92820
tcttatttgt gctaaaaagg tgcagttcca aagtaggaac tgccacacag gccccagcat 92880
cctctctcca acttcatacc tctctcctgg tggggggagc gggcatccag gacctccgga 92940
atcaaggatg tgcagagaag agcgaaagta attttctag tcacatgaac tgattggttc 93000
caggcaatta gaaaatggct ataaaataac cttaatttta aaaaaaatc ttgggtcttc 93060 gttttcctat taggagactg aactgaccac atgtattgat ttatatcctg aatatatggg 93120
aacttctgtg tttgggatgt cctactgtaa gactgatgaa tgtacagagt taatttcagg 93180
gtacagtttt gccttaatgg ttttaaaaaa taaactatttt tttaaaatttt t 93231

<210> SEQ ID NO 3
<211> LENGTH: 15496
<212> TYPE: DNA
<213> ORGANISM: Homo sapiens

<400> SEQUENCE: 3
ggctccaccc ccaagccagg cgaggcaggt tccgaggttg gaacacctgg cgagtcctcg 60
gtgtcggtgg ccggcagtca tctcgcggcc gttcaggtga gggggttgga ggagtggctc 120
atgagcgagg aagggggagc aggcgggctc ccacccggtg ctccgtgaga tcgaggggag 180
cgggttctgg gtgcgatgc acgcgctggg cgggacgctg gcagtggtac ccgagacggg 240
gcggaaggag actggagtga aggtgggcct aggctaaggt acgtgctaga aaggatgaaa 300

```
acggagtgaa attcttaagt gatggaacta ggctagggca tgtttcttgc cctttaaaat      360
gtgttgtctt cgggagacag gacgtagaag atagttgcag cacagggtga taggctggcg      420
aaagttatac aaaagcagga accactagaa ggaggtaaga tgtagtgtgc tttgggagta      480
gtggggttgg gaagggcgtc cgagaggagg ttactgaagg atgactagga gttgaatggg      540
aggacatcac ctgtaaggga acgatatttc cgtgggcaga gaggaatgaa gcagtagcaa      600
ccatgagtga tcagatactg caaaaatgtg aagtgtagga tggcgagaat gtaagaaatg      660
aagagtgaag aagtctggaa gggcctcgtg tgcatcaatc acagcggggc ttgatcttta      720
tgcttagggc aagcactccc ttgaactttg agtgttttaa ggaggttatc tctgatgttt      780
aaatttatat agatcgtggc attgcatctt agaaataagg tttaggaagg caagcttgg       840
aggcagggca agtccagaaa atgaaggagc tggtgaaatc cgtgttaaag tgccaaagga      900
cagagactgg ctgacagcta aacttcaagg tttctgagaa tccacaaata actaaattta      960
tctagtcaac ctgttccaga acaggcttcc agtcatttag gttgcccaag aatgagtaaa     1020
ggaaaaggaa attcaatttt ccaagacctt gtttcccctc tcctctttaa ttccttgttc     1080
ggttagcaac agtatatcca ttccctcgct cctttgtgaa aagtaaattc ctgaatgtta     1140
actaaaccaa gtgtttctaa attgggtaag agtttgaaga cttaaggcag cagaatggga     1200
gagacttaaa acgttatgtc tgagaattag gcattaaagg aggcctagta tttgggcggg     1260
ggttgtgagg agcacatact gaacctttgg acctgttgag tgagttcatg tgcctctgaa     1320
ctctctgact ggatatgacc agtaaacttg gataattaga tcctggagtt taggggagag     1380
ggctagagat agagatgatg gatgtcagca tattttaaa acagaaaata gttaagatca      1440
cccaagacaa tctggaatcg ttagaaggga gtaaggaagg cattattggg aaactttcca     1500
gcttcaattc tcatattttt tctaatctcc tggttgagtc tttggagttg ctgttctctc     1560
tatgcaaaac ccctcccttg accctctctc cctcactcta ttttttaatt tgtcacctcc     1620
ttctcctgtt ctaggtctca gtttagatag caccctttctc tagaagttca tagcactgtg    1680
tattcccccc tttattgttc ttatcacata attttgatg gtttggacac tagttgttat      1740
tcctcactaa attttatgtt ttatgaactc aggggtaagg gcaccagcta gcacaatgaa     1800
tgcacaatac ttgtcagagt gaatgcattt aagttccaag aaccaaggaa aggcggtatt     1860
tcaagaagag aagtatcaaa tcttccagat tagtcaaata aactccaaaa aaaaaaaaaa     1920
aggtttattg gatttggcag ctggagatcc atagcgattt tttttttttt tttttttttt     1980
ttttgagacg gagtctcact ctgtcgccca ggctggaatg cagtgtcgtg atctctgctc     2040
gctgcaacct cagcctcccg ggttcaagca attctcctgc ctcagcctcc ccagtaggtg     2100
gaattacagg catacgccac cacacccggc taatttttt gtatttttt ggtggagatg       2160
tttcaccata ttggccagac tggtctggaa ctcctgacct tgtgatccgc ccacctcagc     2220
ctcccaaagt gctgggatta ccagcgtaag ccaccacacc cagcctcctt agtgatttta    2280
gtaagagtaa gttcagtgca gtgatgacaa tagaatgcag attgcagttg ctagaatata     2340
aacaggaaat aagaagataa agacaactcg tggaatacct tttcatagag cttaggtaaa     2400
ctgtaggaat tattctcctt gtactctaat acttattatg ggttttattt ataattatag     2460
tgtaatataa tggatgagtg catgggcttc cccacttagc atttgttaag cattaactta     2520
acattaagca ttagactttg ggcaagttgc ttaatctttc taaacctcag ttatttttatc    2580
tataaaatgg tgataaaata atacctacct cacgaaggtg tggtaaggat taaagtgaaa     2640
```

```
atgtagagag caggtagcat gctttgaaca cagttcttgg cacagaaagt gcccaataat    2700
tgttagtttc ttgtagctat tacatgccag gtcctgtgct aactaagcgc tttatatgca    2760
ttgtctcttg gactcattgg aagacctact gttttaattt ttgctgctga taaaactgca    2820
tcacagagag gttacctaat ttgcccaagg tcacaggaca ggactagtaa gtggtcttgg    2880
ttcattattg tcaaatttac taatcacctt gagaaaaatt aagattggat ggttgcctta    2940
ttttacaact tagaagatga ttgaagacat tttggtgcag gtggggagcc agattgcaag    3000
tagctcagtg agttgtgtgg gtgagttaag caacctttttt tattcttttt ttttgagacg    3060
gagttttgct gttggtgccc aggctagagt gcagtcacag cttactgaaa cctccacctc    3120
ctcatttcaa gcgattcacc tgaactcctg accttaggtg atctgcccgc atcagcctcc    3180
ccaaggtgct gggattacag gcgtgagcca ccatgcccag ctgagttaag caatctttat    3240
gtagagctct cctttgagaa agaagttggt tggttcaaag aaagataaat gggacagtgg    3300
cttggaagag gtaatggagg ctaggaaggt gtttatcaac aaaggaagat gtaggctggg    3360
cgcagtggct cacacctata atccccacac tttgggaggc tgagatggga ggattacttg    3420
agcctaggag tttaagacca gtctgggcaa cataggtga  cccctgtctc cacaaaaaat    3480
taaaaaaatt agccaggcgt ggtggcatgt gcctgtggtc ccagctacga ggggctgagg    3540
tgggaggatt gcttgagcct gggaggtcga ggctgcaatg agccataatt gtgccactgc    3600
actccagctt gggtgacaga gtgagaccct gtctcaaaaa aaaagaaaaa aaaaagaaa    3660
agacgtgaat gtgttttag  acctgaagga atggattcca tgaagggaga aggatgaaag    3720
atgggaaagg ataagtgatg acaagttct  tgaggtaaga taagaacaca ggaagactag    3780
tcagtcttag aggaaagaat gaatgagcaa agaaatttta aggcctgtaa tgacacagga    3840
tggaacacta tagtcactgt ggtgtaagtc atttgagatg agtaggacag aaggaggacg    3900
gcctgaagtg aattcagatg cctggaggag ttggctaggt tctcaatatt ccttctgtag    3960
aatgggataa aaggtcagtt tgagaagtgt tggggaaggg acttttaaa  gcactattta    4020
gaatgcttct gaggctttaa aatactcatt tttaaaatgg tccaaaaat  tcataaatta    4080
gaagcagcag tggtgaacat ttttaggaaa gtgaccccttg agaagtttat tttttggtta    4140
gtgacctatt gagcttattt attaggtaag tagaacatgc tcatttaaaa agtttaaatt    4200
gtgcaaaaga catatgtcag atttttttt  ctgtcttcca taacactatt tcctaccccg    4260
ccgcgctctg tcttccgtaa cactctcccc taccccgtcg ccactctgtc ttccataaca    4320
ctgtcccccta ctccaccaca ctgtctccta ccccgccgag ctgtcttcca taacactctc    4380
ccctaccccg ccacgctgtc ttcattaaca ctatctcctg ccctgccaca caactctgtt    4440
ttcctagaag tcaccagtgt gaattttttcc ctttatccat atgtacattt tttgtttctg    4500
tgtgtctgtg tatatacata tgcataaaag tgcatagata aaatacatat ccttttcaaa    4560
aaatcttaag tggggctctt gctatgcata ctgttctgta acttgttact tggattaaca    4620
ctgtatctta gacatctttc tatgtagagc gtatagatct tccctgttct tttaaatggc    4680
tgtataattg tctatggaag gacttaattt atttaaccca taccttgttg atggcttatt    4740
tgtgttttgc ttttatttttt tcctctttgt ttttgctgct acaagcaatg cttccttcca    4800
tcttagcgga tctgtctttg taccccttgaa tgagaaagtt gctggatcaa aggatgtatt    4860
cattttgaat taggtgttgc taattttttcc tccaatgata cactgatgta tccccctgc    4920
ccacagtgtg tggtcatgcc tgttctctca cccctcttacc agtactggac attaataagc    4980
tttttaaagat ttgctactca ggctaaaagt gtctctttgt tttagggtgc atttcctcat    5040
```

```
ttaatgaagt gaagattctt ccttgtttag tgaccatttg cctttatttt tctgtgaact    5100
gcttgtgaat ggcatttgtc gttcttctgt tgtcttttta gtcttttttc taaagcacac    5160
tttgtagccc tttgttgtaa aatgttggaa atattttttcc cagtttgtca tttaatcttt    5220
gactttgtct ttctattccc cagtaggagg tacttaatttt ttatatactc atatttggca    5280 ggcttttttct ttataggttc ttttggcttt aagtgatact tttaaaccca gctattgctc    5340
atttaaatta gaacctttttc catgagaacc acactgacga tttctttaaa tatagcttga    5400 aaaaatttttt cccctattgt tctttttagct attgttcttg aaaataatgt gttttttaaa    5460
ggaatatcta caaatagaaa tggtgatgat atccagcaaa tgttttaaaa tggtgtaaaa    5520
ccatttgtac tcctttagta atttttttggt aaaaaattta tactccttta gtaattatca    5580
tttttaaaat gatcagagga tgcattttttt aactgttttta ttttttgaaa gctcattgtt    5640
taacttatta tatatgtatt catttctaca gaattataag gctgtctgca gagatttgaa    5700
aaatggcaac aaatgaaagt gtcagcatct ttagttcagc atccttggct gtggaatatg    5760
tagattcact tttacctgag aatcctctgc aagaaccatt taaaaatgct tggaactata    5820
tgttgaataa ttatacaaag ttccagattg caacatgggg atccctttata gttcatgaag    5880 ccctttatttt cttattctgt ttacctggat ttttatttca atttataccct tatatgaaaa    5940 aatacaaaat tcaaaaggtg agtataaggg actagaaata gaatattatc attaatgttg    6000 ctgaatatttt taaagtaca tagggcttttg ttttgtgagg ctaaagcagt gatatccaat    6060
agaaatatga agccacgtat gtaatttttaa attttctagt agaatacata gaaaaggtaa    6120
aaagaaataa ggaaattaat ttcataatgt gtatcattta gctcaataaa tgtaaactat    6180
cgctgggtgc agggtccatg cctgtaattc cagcactttg ggaggccaag gcaggaggat    6240
tgcttgaggc caggagttca agaccatcct gggaaacata gcaagaccct gtctctacaa    6300
aaaagataca aaaatacccca ggcatggtga tgtaagtcct agctacttat gaggctgaag    6360
cagaaagatt gcagcactat actctagcat aggcgacaga gtgagacctt gtctcaaaaa    6420
aaataagaaa taaatgtaaa ttattatttc aatcagtaat caaattctaa aaaatactta    6480
atgagatatt taataagtct ttgcaattcc gtgtgtatttt tacattaatt ttagtctatc    6540
tcaatttaga ctagccatgt ttaaagtgtt tggaagccac atgttactag ttgctcctga    6600
attgagcaac acagtcctag gtcattattg ataacatttc aagaatactt tgttaaatgg    6660
ggctttaagt agatgtgatg gttatctaac ttaagtttat gaattttaat gtttaagcta    6720
gctgaaaagg aaaggtgtgg tgatttgcgc atattttgca gttcacccca actctatgtt    6780
ccagtaaatc taagggactg ttaatacact acgaccttga tcagggctat tcaagttttt    6840
tttccctaaa tatatggtag gtagtctgc agcattcgta tcatcccaaa taaggaggtg    6900
atgctcctcg tttctggata tttgcttcat tgcactaaat gttgagaggt cgctatgtac    6960
atgacaaggt gaaatctcat atgtagcctg tgagcttgac gtgagaattt ggagtagctt    7020
attagaaaga tgaattattt gttagaattt gtaagctgat gatagtttct agtgtttgct    7080
gtttactttt cataaaaagt cattccaaac taaaactcag gggcacacag tcttggtaga    7140
aagtagacca ttgagagtat tcatctatgg aaagtaattt acattcactt agtacaattg    7200
gccctccata tccatggggtt gttgtatcca tggatccaac caactgcaga tcagaaatat    7260 tcagggggaaa aaaattgtgt ctacactgaa catgtacagt cttttttttc cttgtcatta    7320
ttcaaaatga caactatttta tagagcattt gcattttatt aagtattata agtgctgtag    7380
```

```
agatgattta aagtatacga gaggattcgt gtaggttatg tcaaatacta tgtcatttta    7440
tatcaggcac ttgagcatct tcagatcttg gtatttgcag aaagtcccag aaccaatcct    7500
caaaagatac caaaggacaa ctgtatatat tttggatggc agtctgtaca cattctctgt    7560
tatcattctg ttagtttcac agcctctccc agagtctcac tttaagcagg tattaatatt    7620
agtcctctct ggggataatg cagggtcag atgactgtgg actccaggcc aaaggagaaa     7680
agagcaaagg gtaaaggcga aggaaataaa aaataggagg gccaaaggag agtactctgt    7740
gaccctcaat taaggtcaca gaagctccaa agtgcttttt aggaaagcag ctgctttgaa    7800
aggcagaatt aagtttggac gtctaagttc taatgcacct ttagggtgat gtggctgcc     7860
gtgtttcacc cagtgattta tttataggc ttattcattg taattcattg tatggctggc     7920
caggcaaaag catcctttt ctccttcact gcagtttgta actgactcac tggttagaag     7980
tagtaacctt tgcagagaga caaaggactt tctcaggcaa gggtatatga gcagctttaa    8040
aatataatgt ggcaaaggaa agaataagct gtagtctagt tggtcagagc tagttgttta    8100
tgaacagatt gtaaggctgg ataatttgac ttcaagtctg tactcagcaa gtctttatgt    8160
ttcataacca ttaaagtcca tgctttgagc attttttgata aaaaatgtga ttttaaacca   8220
ggactagttt tcacaagtta aaggagtttt aaaagaaacc aaaatattgg tacaaattaa    8280
ttacaggttt atgcatttcg aaggcagata ccctgattaa cattgagggt atcaattgtt    8340
taagataaaa tatttgagaa ttatatttaa catatgcaat aaatgttttt attcttaaaa    8400
ttgtcgaaaa gaatagaaga agttggtggt ggtgatgaaa tagtactaaa gactttctgc    8460
tttcaaacag aacagacaac tggagagcta atgcacatcc ttgctagtta ggcgaaaatt    8520
tcacaggaat gaaaagtaa agcagacttt gcaggatcta tttctttaaa aaaaaaaaa     8580
acatacatct tagtaattct ccaaaaattt tcctcaaaga taaatgtact aaaaatatta    8640
tttctgaagt ttgtggccct tgtaaaggta ttcctttata ttaagtacag ttatgcataa    8700
agaaagtaaa atatggtaaa ctttcatatt gcactaggta tgaatttgta ttgctaactg    8760
tctttgtaac taatttatgt atactgtaaa tggtatagca tgtgatttta ttatagttga    8820
ttaactttgt aatttctgta actgcatcga tatcccagtc tacctggaaa attaagtcta    8880
ttaaccatag ttgctgtagg agacagtact attgccaact gaagcctgaa tccttcattt    8940
attttgtccc caattacaga gtggaggttt agaggagtgg ggttagataa tgctcagatt    9000
agaaatacaa aggcagctgt cagatcctcc cattttattg ttgaagaaac tgagttgtaa    9060
acatcacaag agctagttaa ctggtgagta gcagccctgg tattagagca caagtctctg    9120
gattgattct tagttcagtg cttttcctat ttttgtcagg aagataaccc ttaaagaatt    9180
tcaagaacag agctggatct ggagacctag attttagtta gtccaacttc tgctaataac    9240
tgcgtgtgtg accctgccca agctggttga cctctttggg cttctgctga tgcgcagtag    9300
ttcccgtact ttggatatcg tggttcaatt aaaagagttt tgttggcgga tacctgaatt    9360
tttcagcagt gacatttaaa acaaagcaat aactgatatt tattgtcacc atcgttttgt    9420
taagcccaaa gcactttttt aagtgcagtc ctataaattg aatacattta gttagtgttt    9480
gttttgtttt gctttgtttt ttataatgac ttgctaagca aatgggtatc ctgatgaggt    9540
cttaacgaac atcccatgtt gatctaactt ttctcatttt gacttgaatc tgtgaactcc    9600
ataatcagga catatctgtg tacttctcaa ctcagagagt ttataattct gtcattggat    9660
ttgaacaaaa gtgcatttat ttgttggaat gaataccact gagtgcctgg aagcatcgac    9720
ttactgtgta aaaggcttcc aatgcttcgt atacaacttc ttcaattgtg gacacccaac    9780
```

```
agtaatctta gcatattata tttcttcttc tctgaaactt ctggtaaaag aagtgaagtg   9840
aatgatctgt ggcagcaaag actggagaat tattcattcc atagtgtttc ttagtttgtt   9900
tgagatcatc atggctaggc gcatctgtta acagtttctt cacctgaagt agtgatagta   9960
gttgtcaaga atttagaagg caaagattcc tgagtcttag ttatataaag ttaacataac  10020
tgacgtagaa ttaaggtcca acataaacag agaacaaatt aggtcaagtt aaactctgat  10080
agcagagact aatattagat attgtgattt ttcttcgtag gataagccag agacatggga  10140
aaaccaatgg aagtgtttca aagttcttct ctttaatcac ttctgtatcc agctgccttt  10200
gatttgtgga acctattatt ttacagagta tttcaatatt ccttatgatt gggaaagaat  10260
gccaagatgg tacgtagata aaaatttggc ttttacaccc aattgtggct tattcagtta  10320
agttatactt aatgtttacc cgttttctta attttagtta atgtttgttc taaactttgg  10380
aagtaaataa atagtagaaa agtaaaccac agtaaaatct aaaatgtttt ccatttttac  10440
atcttttaaa tatttttattg gaaggtgagc ttcagtatc agaagtttcc ataacgtctt  10500
ttgtatgttt atatacatgt ataagtgctt atgttgacaa aaatatatta cattttaatt  10560
ttaaaatgaa tgaaatatat gagaatcatt tatgaggttt atagaaattg tgtttacatg  10620
aacaaaaata tgtatgtgta tatatatata tatatatata tacacacata tatatataca  10680
cacacatata tatactcatg cgtcacttaa cggatatctc ttgagaaaag tgtcatgagg  10740
caagttgtgt gaacattgta atgaaatgaa attggtctaa tgggcagtct ctttaacctt  10800
atatcaagtt atgtagctgt atctggtggt tttgagaatt tatttatgaa tatatccaat  10860
taggtcaacc tggtaagtgg gtgggtggtt ttatgtaatg tctcaagcag tgatcccaac  10920
taaaagtctg gatagtttaa gtaaaaatta tttcttacac attacaacat ttttatctta  10980
aaggtatttt cttttggcaa gatgctttgg ttgtgcagtc attgaagata cttggcacta  11040
ttttctgcat agactcttac accacaaaag aatatacaag tatattcata aagttcatca  11100
tgagtttcag gtatgtgaga gttatattta attctttctg ttagaggcaa aatgtctatt  11160
ttaattgcct gagcattttt ctaaaattgt tggtgacgtt tttatttct tttcctttgg  11220 catgattatt aagaacaata cacacacata caaacaagcc atttctacac attgttttca  11280
ttatttaaat ttcatggtaa attgagatct gaaagaaaaa tattatatga aagttcggac  11340
ttccatcctt gtggacagtg ctacactggc acagctagat cctcacattg ctaactccca  11400
caaaaacagt aacttctatg agcactgctt tttttttttt ttttttttttt tttgagatag  11460 agttttgctc ttgttgccca ggctggactg caatggcatg atctcagctc actgcaacct  11520
tcacctcctg ggttcaagca attctcctgc ctcagccttt caggtagctg ggattacagg  11580
catgcgtcac cacgcgtggc taattttgta ttttagtag agacaggatt tcactatgtt  11640
ggtcaggctg gtctcgaact cctgacctca ggtgatccac ccgccttgga ctcgcaaagt  11700
gctgggatta caggcgtgag ccaccatgcc cggccaatta gaattgcttt gatgtagctt  11760
tgtcaactgg ttatgtgagt atgttttgca ttgaccgtga ttacatggtg tgccaaatca  11820
agcctctctt tattagaaga acaaatataa atacttaagt caaaattaga gttcaagtca  11880
attatttaat gcctttatct taaaccatca aagcagcaa gattttatat ccctagactt  11940
ttgatgtgga gtaaggtatt tttattgaga attgctagta ttatttataa gtgtatgact  12000 agataaaatca tcactacata tagaatcaat ataactttgt aaaactttat gcataaatag  12060
gatatatata ttagtgaagt ctccagtgaa gcagaatcat tggggtatat atatgcagag  12120
```

```
agagatttat tttaaggaat cagctcatgc aagtgtgcgg ctgtcaagtc tgaaatctgt   12180
aaagcaggct acagactaga aatccaggta agaattgttg cagccttggg tccaaattcc   12240
atggagcagc aagttggaaa ctcaggcagg gtttcagtgt tgcagtctcg agaatccttc   12300
ttcaggaaac ctcagccttt tatcctgaag gccttcaaat gattggatga agcccaccct   12360
cattatgaag ggtaatcacc tttactcagt ctactgattt aaatgttaac aacatctaaa   12420
aaataccttc acaacaacat ctagactggt atttaatcaa acagttggat atcatagcct   12480
agccaagttg acacataaaa ttgaccatca caatagctaa gaaattaaga atttcttatc   12540
tgtttgtctt aggctccatt tggaatggaa gctgaatatg cacatccttt ggagactcta   12600
attcttggaa ctggattttt cattggaatc gtgcttttgt gtgatcatgt aattcttctt   12660
tgggcatggg tgaccattcg tttattagaa actattgatg tccataggtg agtattaatt   12720
tctgttcagg tataaagcat aatgaaatat atttattttc atggccataa gattatcata   12780
tttctaagga gactaatagg agaagttaat cttcttaatg ttatattaag aaaacataac   12840
tgttggataa aagtttaaat aatagatgtt tttacattct agcctatgct gttataattt   12900
ttatagtgat aatgtgttat tagggcaagt atatattcag gaccagcaat ttccttatcc   12960
ttctgtaata aacctaaact taactcatat ttgaaaaaaa tatcaaagca ttcagccttc   13020
cttgaataag actttctaat ctctactgtt cagcactgat aaaggcactt gcaagatgaa   13080
actactactt gtaacacata catatttcaa atgcatcctt tctgttgatt ggaagacatt   13140
ttgtggtaaa ttatttatat tgaatgcctt cttaaatgct tatcctaatt gttcattatt   13200
ttttaattat atgttcattg cattttgact tgggacatac ttctgtactc atgaatgcag   13260
aatatcaaat tctaagaatt atttttaaag tgctaaagta gcaaaattaa tgcttctagt   13320
cctaggcaga gaatattctt ctgtagaaaa attgtaattg acatttcttt ctttttttt   13380 tctatccatt gtttctttct gccttccttc ctctaagctc ctcaaaggaa gagagggtta   13440
gagtgattca aataagtata actggatgtc tgattgtaga tatgtagttg gaaataaagg   13500
agcatacttt aaatgggact cttttttgaa gccatttgtc ttctgccaac tatagaaaag   13560
tacactggta ttttgattaa ttgtggtaca tttgattcca acttgtcatt gcctaaaaaa   13620
gtaaatgaag ttgctataca gggattcatg ggcctgccct ttttaatact tgatactaat   13680
tttatgtgac ttttcctaaa aaacatattt agtattttgg gctttattta caactgttat   13740
acatgatggt gagaaagctt cctctaaaac ataaagaaa attaattctt aaaaatctgt   13800
gtctaaagat tcattactat aatccgtctc ttccatcatt catatatttt atcataaaat   13860
aaatgatttt cttagttttt ttaaggattt ttttttcttag agtggtttct agaatataca   13920
ccattttctg tgtttgctgt ttgtgaacac ttagaaataa agtggtctag gcaaagtggc   13980
atgttatcta aattggttaa tgtgaacaca tgattattaa taaaaacaac aatcatttga   14040
gatgtattta ttccttaata atctttatca tttttgtttc agtggttatg atattcctct   14100
caacccttta aatctgatcc cttttctatgc tggttctcgg catcatgatt tccaccacat   14160
gaacttcatt ggaaactatg cttcaacatt tacatggtgg gatcgaattt ttggaacaga   14220
ctctcagtat aatgcctata atgaaaagag gaagaagttt gagaaaaaga ctgaataaat   14280
atctcacgta aaccttcctg aaagataaac gttttcctga attcagaaac tagtagctaa   14340
cattgcttct ggagagcaga aataagcatg tcttctggct actaagtgat aaaaagaaca   14400
ttaacaacct ttaattacct tcctagtggg aacttttttct actttaccta caagttctat   14460
atatgtagaa atgaataaat atatatttaa gtacagtttt catgaggaag ttttaaaaga   14520
```

```
ccatgttcct aagcttccaa gaaggttttg gatactagaa gtattaatct atggcttttc    14580
tcccagtaaa accataggcc tgaagttcac attgggtctt taaatctttt agatatatac    14640
tggtcatttc agaaaattct tcatagtggt attggcctta tatttaactt ttttttttatt    14700 ttttttttga gacaaagcca cactctgtct ccttggctgg agtgtggtgg cacagtctca    14760
gctcactgca acctctgcct cccagttcaa gcaattcttc tgcctcagcc tcccaagtag    14820
ctgggattac aggcacccgc caccacgccc agctaatttt tgtattttttg tagagatggg    14880 gtttcacgat gttggccagg ctggtctcaa acttctgacc tcaagtgatc tgcccacctt    14940
ggcctcccaa agtgctggga ttacaggtgt aagccactgc gcccggcctt tttaacttta    15000
aacatgtttt agaattcacc taaagatcaa aatatcatgg attgaacctc atcaattgat    15060
agcagtgagt gactgaagct tccaaatcaa gaaaagccgg caccaagaac ttccattcta    15120
atctagagct gaccagtttg agctgattct ctctttgaag agtccttctt gattgcagtg    15180
cagtactggc atttctgaat ggatgtaagt ggagtatttt agtctaaagg cttttcaaat    15240
tacttgaatt tttttaaaaa ttgaggagct ttatttctat ttaccttcc atttttgtat     15300 atcaaatttc cattgtcatt aaaaactgta tcttgaaact ttgtgaactg acttgctgta    15360
tttgcacttt gagctcttga aataaatgtg attttttgtgt gattatctgg tttccagttt   15420
taaacattaa ctgtcacctt ttattcttaa acttgaaagt acagaaatca ttaaattatt    15480
aagttgtaca ataaaa                                                    15496
```